(12) United States Patent
Heins et al.

(10) Patent No.: US 8,951,792 B2
(45) Date of Patent: Feb. 10, 2015

(54) METHODS FOR MAKING DEFINITIVE ENDODERM HEPATOCYTE (DE-HEP) PROGENITOR CELLS

(75) Inventors: Nico Heins, Västra Frölunda (SE); Gabriella Brolén, Gothenburg (SE); Barbara Küppers-Munther, Gothenburg (SE)

(73) Assignee: Cellartis AB, Gothenburg (SE)

( * ) Notice: Subject to any disclaimer, the term of this patent is extended or adjusted under 35 U.S.C. 154(b) by 963 days.

(21) Appl. No.: 12/219,298

(22) Filed: Jul. 18, 2008

(65) Prior Publication Data

US 2009/0123432 A1 May 14, 2009

Related U.S. Application Data

(60) Provisional application No. 60/935,003, filed on Jul. 20, 2007, provisional application No. 61/071,215, filed on Apr. 17, 2008.

(51) Int. Cl.
*C12N 5/00* (2006.01)
*C12N 15/00* (2006.01)

(52) U.S. Cl.
USPC .......................................... 435/325; 435/455

(58) Field of Classification Search
USPC ................................................ 435/455, 325
See application file for complete search history.

(56) References Cited

FOREIGN PATENT DOCUMENTS

| JP | 2002-534974 | 10/2002 | | |
|---|---|---|---|---|
| JP | 2003-520596 | 7/2003 | | |
| JP | 2004-510432 | 4/2004 | | |
| JP | 2004-510434 | 4/2004 | | |
| JP | 2004-531270 | 10/2004 | | |
| WO | WO03/055992 A2 | 7/2003 | | |
| WO | WO2004/098285 A2 | 11/2004 | | |
| WO | WO2004/099394 A2 | 11/2004 | | |
| WO | WO2005/063971 A | 7/2005 | | |
| WO | WO 2006/034873 | * | 4/2006 | ............... C12N 5/08 |
| WO | WO 2007/059501 | 5/2007 | | |

OTHER PUBLICATIONS

Cai (Hepatology, May 2007, vol. 45, No. 5, p. 1229-1239).*
Zhou (International J. of Biochem. & Cell Biology, May 2007, vol. 39, No. 9, p. 1714-1721).*
Hay (Cloning and Stem Cells, Apr. 2007, vol. 9, No. 1, p. 51-62).*
Corning catalog, 2011.*
CD 117 description on Wikipedia, 2013.*
Standard European Search Report from European Patent Office, transmitted on Oct. 23, 2007.
Sjögren-Jansson et al., "Large-Scale Propagation of Four Undifferentiated Human Embryonic Stem Cell Lines in a Feeder-Free Culture System", Developmental Dynamics, 233:1304-1314, 2005 Wiley-Liss, Inc.
D'Amour et al., "Efficient differentiation of human embryonic stem cells to definitive endoderm", Nature Biotechnology, vol. 23, No. 12, pp. 1534-1541, Dec. 2005.
Cai et al., "Directed Differentiation of Human Embryonic Stem Cells into Functional Hepatic Cells", Hepatology, May 2007, pp. 1229-1239.
Noaksson et al., "Monitoring Differentiation of Human Embryonic Stem Cells Using Real-Time PCR", Stem Cells 2005; 23:1460-1467.
Heins et al., "Derivation, Characterization, and Differentiation of Human Embryonic Stem Cells", Stem Cells 2004; 22:367-376.
D'Amour et al., "Production of pancreatic hormone-expressing endocrine cells from human embryonic stem cells", Nature Biotechnology, vol. 24, No. 11, pp. 1392-1401, Nov. 2006.
Söderdahl et al., "Glutathione transferases in hepatocyte-like cells derived from human embryonic stem cells", ScienceDirect, 2007 Elsevier Ltd., pp. 929-937.
Zhou et al., "In vitro differentiation of embryonic stem cells into hepatocytes induced by fibroblast growth factors and bone morphological protein-4", ScienceDirect, 2007 Elsevier Ltd., pp. 1714-1721.
Hay et al., "Direct Differentiation of Human Embryonic Stem Cells to Hepatocyte-like Cells Exhibiting Functional Activities", Cloning and Stem Cells, vol. 9, No. 1, 2007. pp. 51-62.

* cited by examiner

*Primary Examiner* — Michael C. Wilson
(74) *Attorney, Agent, or Firm* — Buchanan Ingersoll & Rooney PC

(57) ABSTRACT

The present invention relates to a novel hepatocyte-like cell progenitor and/or a novel hepatocyte-like cell derived via definitive endoderm from human blastocyst-derived stem (hBS) cells, to a method for the preparation of such cells and to the potential use of such cells in e.g. pharmaceutical drug discovery and development, toxicity testing, cell therapy and medical treatment.
In particular is presented a definitive endoderm derived hepatocyte-like cell with important liver-expressed marker genes and important metabolizing enzymes, as well as drug transporters.

18 Claims, 51 Drawing Sheets

Basic DE-hep differentiation strategy

Figure 1C:
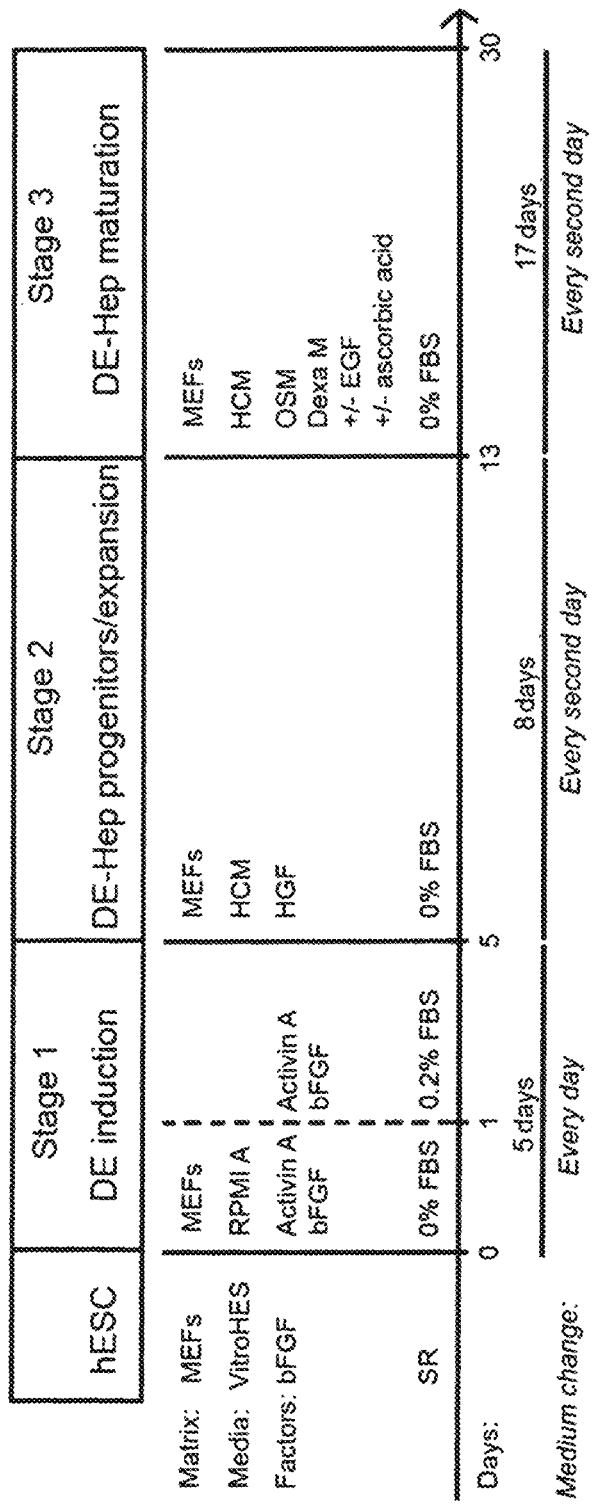

|  | Stage I:<br>Definitive<br>endoderm | Stage: II<br>Liver progenitor<br>phase | Stage: III<br>Hepatocyte<br>maturation |
|---|---|---|---|
| *Basic protocol* | Activin A | BMP4 + FGF2 | HCM medium |
| *Variations of the basic protocol* | FGF2<br>Wnt3a | FGF1<br>FGF4<br>BMP2<br>HGF<br>EGF | HGF<br>Dexamethasone<br>Oncostatin M<br>EGF<br>Insulin<br>Transferrin |

Fig. 1A

Protocol 1.

| | Stage 1 | Stage 2 | | Stage 3 |
|---|---|---|---|---|
| hESC | DE induction | DE-Hep progenitors/expansion | | DE-Hep maturation |
| Matrix: MEFs | MEFs | MEFs | | MEFs |
| Media: VitroHES | RPMI A | RPMI A | | HCM |
| Factors: bFGF | Activin A / Activin A / bFGF / bFGF | aFGF / bFGF / BMP2 / BMP4 | aFGF / bFGF / BMP2 / BMP4 | bFGF / BMP4 / HGF | HGF |
| SR | 0% FBS / 0.2% FBS | 0.2% FBS | 0.2% FBS | 0.2% FBS | 0% FBS |
| Days: 0 | 1  4 | 4  6 | 8 | 18  30 |
| | 4 days | 14 days | | 12 days |
| Medium change: | Every day | Every second day | | Every second day |

Specific embodiment of the invention

Fig. 1B

Protocol 3.

| hESC | Stage 1<br>DE induction | Stage 2<br>DE-Hep progenitors/expansion | | Stage 3<br>DE-Hep maturation |
|---|---|---|---|---|
| Matrix: MEFs<br>Media: VitroHES<br>Factors: bFGF | MEFs<br>RPMI A<br>Activin A \| Activin A<br>bFGF \| bFGF | MEFs<br>HCM<br>FGF4<br>BMP2 | HCM<br>HGF | MEFs<br>HCM<br>OSM<br>Dexa M<br>+/- EGF<br>+/- ascorbic acid |
| SR | 0% FBS \| 0.2% FBS | 0% FBS | 0% FBS | 0% FBS |

Days: 0 ——— 1 ——— 5 ——— 10 ——— 16 ——— 30

5 days | 11 days | 14 days

Medium change: *Every day* | *Every second day* | *Every second day*

Fig. 1D

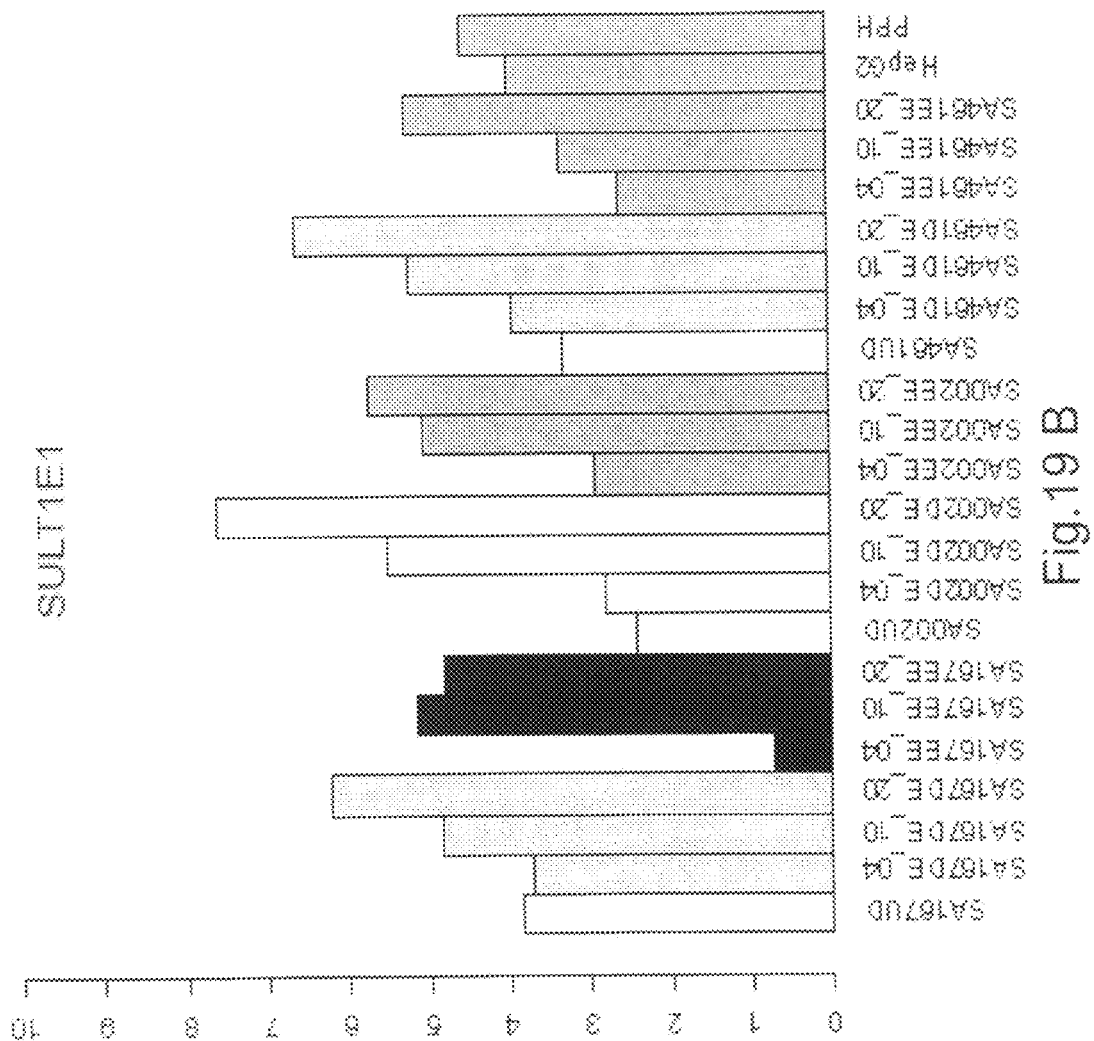

Control isotype

A)

… … …

METHODS FOR MAKING DEFINITIVE ENDODERM HEPATOCYTE (DE-HEP) PROGENITOR CELLS

The benefit is claimed under 35 U.S.C. §119(e) of U.S. Provisional Patent Application No. 60/935,003, filed Jul. 20, 2007, and U.S. Provisional Patent Application No. 61/071,215, filed Apr. 17, 2008.

FIELD OF THE INVENTION

The present invention relates to a novel hepatoctye-like cell population derived via definitive endoderm from human blastocyst-derived stem (hBS) cells, to a method for the preparation of such cells and to the potential use of such cells in e.g. pharmaceutical drug discovery and development, toxicity testing, cell therapy and medical treatment. The cells are denoted DE-hep cells herein.

Furthermore, the DE-Hep cells exhibits properties of functional human hepatocytes which make them attractive for use in in vitro studies of hepatogenesis such as early liver development processes or liver-regenerative disorders or malformations.

BACKGROUND OF THE INVENTION

Pluripotent human stem cells are expected to revolutionize the accessibility to a variety of human cell types. The possibility to propagate pluripotent human blastocyst-derived stem (hBS) cells and subsequently differentiate them into the desired target cell types will provide a stable and virtually unlimited supply of cells for a range of applications in vivo and in vitro.

Liver failure and end-stage liver diseases are responsible for a huge amount of deaths around the world and is a major burden on the health care system. Liver transplantation remains the most successful treatment. However, the efficacy of this procedure is limited and connected to many complications such as infection or rejection. Liver transplantation also suffers from shortage of available donor organs and the treated patients will very often be referred to lifelong immunosuppression. By reducing the need for organs, cell-based treatments will be of great importance to both society and to the individuals suffering from these severe diseases.

Furthermore, the liver is the centre of metabolism and detoxification in the human body, and therefore huge efforts have been undertaken in order to identify a reliable source of functional cell types for in vitro testing. Unfortunately, the complexity and function of the liver is not mirrored by any cell type available today. The availability of primary human liver cells is very limited and the cells are also known to rapidly loose their normal phenotype and functional properties (i.e. within 24 hours) when used for in vitro applications. One often used alternative to primary cells are hepatic cell lines which in turn contain very low levels of metabolising enzymes and have distributions of other important proteins substantially different from the native hepatocyte in vivo. Thus, many tests are still performed using animal material, even though liver metabolism is known to be species specific and thereby generating difficulties in predicting liver metabolism and toxicity in another species than the one tested.

In pharmaceutical development adverse liver reactions remain the most prominent side effect. Therefore early prediction of human liver toxicity liabilities is of paramount importance when selecting compounds to enter clinical trials. Efforts to improve capabilities in this area must address both the availability question and development of models, which provide greater coverage for the complex biological processes which coincide to induce adverse liver injury in human. In both areas the use of differentiated cells derived from hBS cells provide promising opportunities.

Accordingly there is an urgent need for a model system that mimics human liver cells and that is able to predict effects of candidate molecules in the development of new drugs or chemicals. Regarding both availability and physiological relevance human pluripotent stem cells may serve as an ideal renewable source of functional human hepatocytes. When hBS cells have been placed in a proper environment certain hepatic characteristics have been observed after 2-4 weeks of differentiation.

The present invention is based on the fact that definitive endoderm (DE) cells give rise to endodermal organs and thus hepatic cell types. Early endoderm development is not well understood. Directed studies of cultured mouse embryos (Lawson et al., 1986, 1991; Lawson and Pedersen, 1987) have revealed that DE begins to form at the embryonic days 6-6.5 (E6-6.5) and that by the end of gastrulation (E7.5), some labelled cells only give rise to endodermal derivatives. It is not known whether the initial DE cells are multipotent. Fate mapping studies (Lawson et al., 1991; Tremblay and Zaret, 2005) suggest that the first endoderm cells that migrate through the primitive streak (PS) at E6.5 are fated to become liver, ventral pancreas, lungs and stomach. Co-culture experiments show that the endoderm at this state is not fully committed at the early state of development (Wells and Melton, 2000).

A complication in the study of endoderm is that mammals possess extraembryonic endoderm. Extraembryonic endoderm arises at the blastocyst stage and eventually forms two subpopulations: visceral endoderm and parietal endoderm. Extraembryonic endoderm cells share the expression of many genes with DE (cells that give rise to the endodermal organs), including the often analyzed transcription factors Sox17 (Kanai-Azuma et al., 2002), FoxA1 and HNF3b (Belo et al., 1997; Sasaki and Hogan, 1993). D'Amour et al. have developed a protocol for deriving definitive endoderm from hBS cells (D'Amour et al., 2005; D'Amour et al., 2006).

In the present invention is presented a hBS cell derived hepatocyte-like cell population for use in drug discovery and regenerative medicine with a stable expression of important liver-expressed marker genes such as Albumin, CYP3A4 and UGT2B7 for at least 24 hours and of important metabolizing enzymes as well as drug transporters.

BRIEF DESCRIPTION OF THE INVENTION

The present invention relates to hepatoblast-like cells and hepatocyte-like cells derived from definitive endoderm, DE-Hep progenitors, and DE-Hep cells.

Figure 1E:
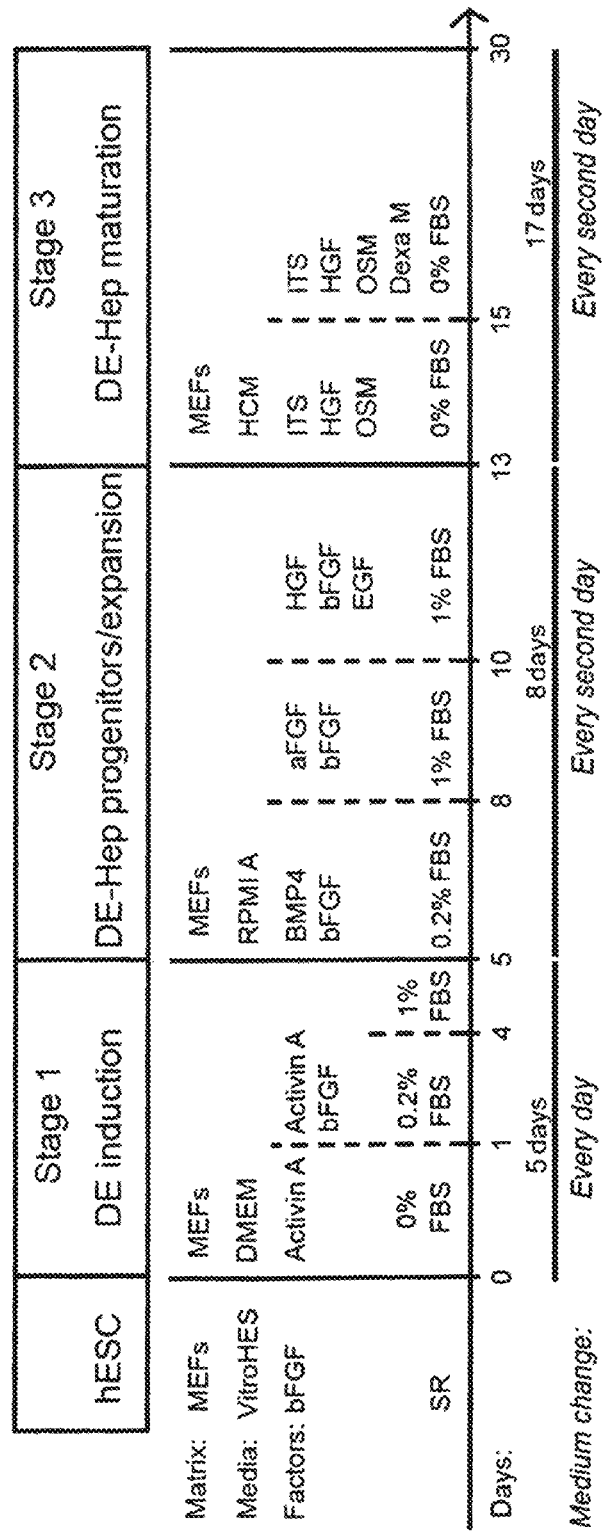
Figure 1F:
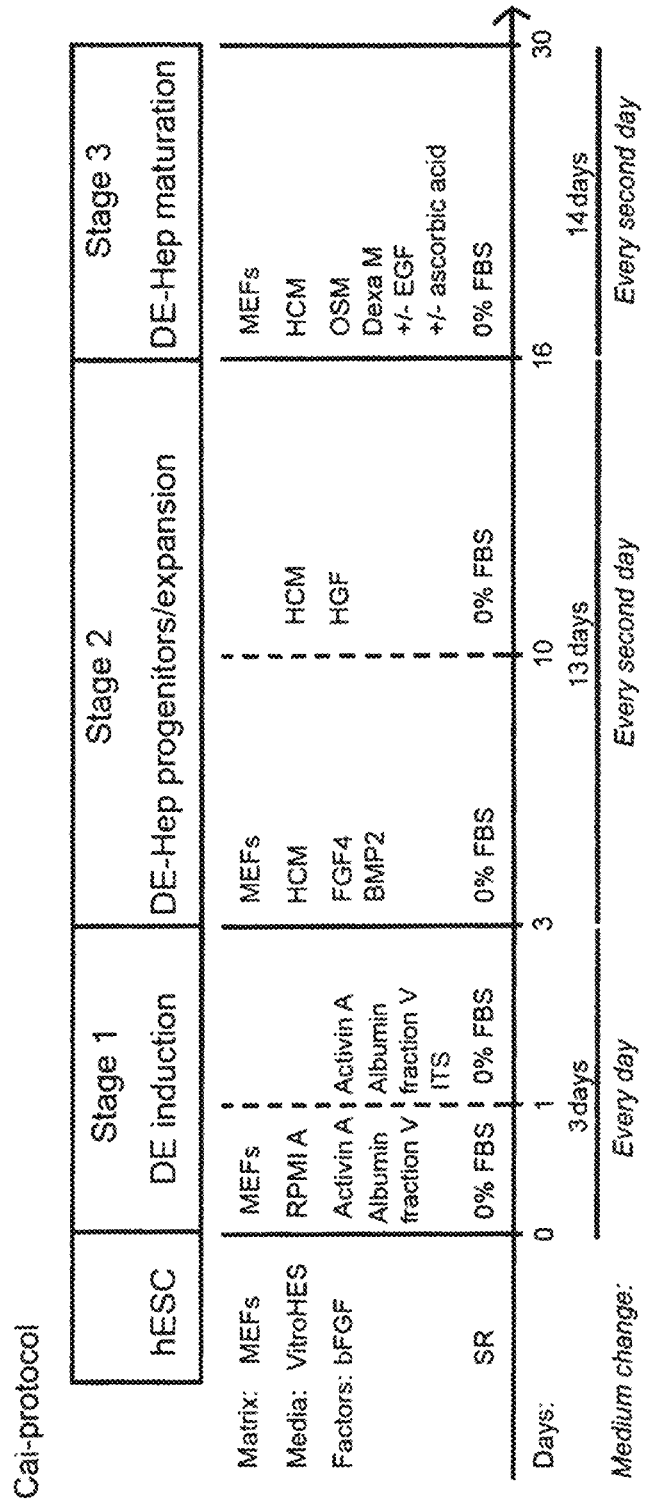

As it will appear from the below description, the present invention also relates to a stage-divided method for the preparation of these cells, i) DE-Hep progenitors and ii) DE-Hep cells. This method, as depicted in FIG. 1 A and B, involves the formation of DE cells by culturing hBS cells (stage I), thereafter obtaining DE-hep progenitor cells from the DE cells (stage II), and finally the formation of DE-Hep cells (stage II) from the DE-hep progenitor cells.

One aspect of the invention concerns a method for the preparation of DE-Hep cells derived from human blastocyst-derived stem (hBS) cells via definitive endoderm, the method comprising subjecting hBS cells to culturing conditions comprising i) a stage I, wherein the hBS cells are induced to develop into definitive endodermal cells, stage I comprising 2-6 days of culturing of the hBS cells in a first stage I culturing medium comprising activin, wherein the medium after one day of culturing is replaced by a second stage I culturing medium comprising activin, one or more growth factors and, optionally, serum, ii) a stage II, wherein the cells obtained from stage I are propagated, and stage II comprising culturing the cells from stage I in a stage II culturing medium comprising one or more of a growth factor and optionally a bone morphogenic protein, iii) a stage III, wherein the cells obtained from stage II are matured into hepatocyte-like cells (DE-Hep cells), stage III comprising culturing the cells from stage II in a stage III culturing medium comprising one or more of a maturation factor and optionally a differentiation inducer.

Another aspect of the invention relates to DE-hep progenitor cells obtained by the above method. The cells obtained from stage II exhibit protein and/or gene expression of one or more of HNF1, HNF3b, HNF4a, EpCAM, AFP, Desmin, CD133, ICAM1 (CD54), CK8, CK18 and CK19. The DE-hep progenitor cells exhibit gene expression of CK8, CK18 and CK19, ICAM. As demonstrated in the examples herein, the DE-hep progenitors cells normally also exhibit protein and/or gene expression of EpCAM and one or more of HNF1, HNF3b, HNF4a, preferably all. A cell population comprising DE-hep progenitor cells and obtained according to the invention normally contains at least 25% of DE-hep progenitor cells, preferably 50% of the cells are DE-hep progenitor cells. Dependent on the percentage of DE-hep progenitor cells in the cell population, a certain percentage of the cells may exhibit the desired protein and/or gene expression. Accordingly, the percentage is very much dependent on the "purity" (i.e. the same identity of cells) of the cell population. However, a cell population having a low percentage of DE-hep progenitor cells can be subjected to selection of the cells and proliferation of such cells and this will in turn lead to a higher percentage. Notably, the DE-hep progenitors cells exhibit protein and/or gene expression of CK8, CK18 and CK19 (normally at least 50% or the cells in a DE-hep progenitor cell population obtained as described herein exhibit protein and/or gene expression of CK8, CK18 and/or CK19).

The present invention relates to a DE-hep progenitor cell having the above-mentioned characteristics as well as to a cell population comprising DE-hep progenitor cells.

A further aspect of the invention relates to DE-hep cells obtainable by the method described herein. DE-hep cells exhibit protein and/or gene expression of one of more marker for drug transport, notably BSEP, MRP2, OATP-2 (=OATP-C, OATP1B1), OATP-8 (OATP1B3), OATP-A (=OATP1A2), NTCP, MDR1, MDR3, OCT-1. Notably, the DE-hep cells exhibit protein and/or gene expression of the following markers for drug transport: MRP2, OATP-2 (=OATP-C, OATP1B1), OATP-A (=OATP1A2), NTCP, and OCT-1. Moreover, in at least some of the protocols described herein, the DE-hep cells obtained also exhibit protein and/or gene expression of the following markers for drug transport: MDR1 and/or MDR3.

A further aspect of the invention relates to DE-hep cells obtainable by the method described herein. DE-hep cells exhibit protein and/or gene expression of one of more marker for drug metabolism enzymes, notably GST A1-1, GSTM1-1, CYPs (CYP1A1, CYP1A2, CYP1B1, CYP2A6, CYP2B6, CYP2C8, CYP2C9, CYP2C19, CYP2D6, CYP2E1, CYP3A4, CYP3A7, CYP7A1, UGT1A6, UGT1A and/or UGT2B7. Notably, the DE-hep cells exhibit protein and/or gene expression of the following drug metabolism enzymes CYP2C9, CYP2C19, CYP2D6. Moreover, as demonstrated in the examples herein DE-hep cells also exhibit protein and/or gene expression of CYP1A1, CYP1A2, CYP1B1, CYP2A6, CYP2B6, CYP2C8, CYP2E1, CYP3A4, CYP3A7, CYP7A1 as well as of UGT1A6, UGT1A, UGT2B7.

A further aspect of the invention relates to DE-hep cells obtainable by the method described herein. DE-hep cells exhibit protein and/or gene expression of one of more marker for transcription factors, notably FXR, RXRα, RXRβ, RXRγ, HNF1α, HNF3α, HNF3β, HNF4α, HNF6, C/EBP A, C/EBP B. Notably, the DE-hep cells exhibit protein and/or gene expression of the following marker for transcription factors: RXRγ. Moreover, as demonstrated in the examples herein, DE-hep cells also exhibit protein and/or gene expression of FXR, RXRα, RXRβ, HNF1α, HNF3α, HNF3β, HNF4α, HNF6, C/EBP A, C/EBP B.

In a specific embodiments, the DE-hep cells exhibit protein and/or gene expression of one of more marker for drug transporters and drug metabolism enzymes, the DE-hep cells exhibit protein and/or gene expression of one of more marker for drug transporters and transcription factors, the DE-hep cells exhibit protein and/or gene expression of one of more marker for drug metabolism enzymes and transcription factors, and the DE-hep cells exhibit protein and/or gene expression of one of more marker for drug transporters, drug metabolism enzymes and transcription factors (cf. the specifically mentioned markers in the paragraphs above).

Moreover, DE-hep cells obtained by the above method, may exhibit increased protein and/or gene expression of the following: albumin, UGT2B7, CYP3A4 compared to using the same kind of cells but subjecting the cells to intrinsic differentiation. As shown in the examples herein the expression of albumin based on DE-hep cells according to the present invention is increased with a factor of at least 5, but can be as high as about 140 using a specific protocol (protocol 2 or 4). On average, the expression of albumin is increased with a factor of about 80 or 90. As shown in the examples herein the expression of UGT2B7 based on DE-hep cells according to the present invention is increased with a factor of at least 3, but can be as high as about 85 using a specific protocol (protocol 2). On average, the expression of UGT2B7 is increased with a factor of about 30 or 40. As shown in the examples herein the expression of CYP3A4 based on DE-hep cells according to the present invention is increased with a factor of at least 20, but can be as high as about 200 using a specific protocol (protocol 3). On average, the expression of albumin is increased with a factor of about 100 or 110.

The DE-hep cells of the present invention are especially well suited for use in drug discovery and toxicity testing, because they express drug transporters and/or metabolizing enzymes. Furthermore, the DE-hep cells obtained by the present invention exhibit expression of important marker genes for mature liver cells such as Albumin, CYP3A4 and UGT2B7.

A cell population comprising DE-hep cells and obtained according to the invention normally contains at least 25% of DE-hep cells, preferably 50% of the cells are DE-hep cells. Dependent on the percentage of DE-hep cells in the cell population, a certain percentage of the cells may exhibit the desired protein and/or gene expression. Accordingly, the percentage is very much dependent on the "purity" (i.e. the same identity of cells) of the cell population. However, a cell population having a low percentage of DE-hep cells can be subjected to selection of the cells and proliferation of such cells and this will in turn lead to a higher percentage.

The present invention relates to a DE-hep cell having the above-mentioned characteristics as well as to a cell population comprising DE-hep cells.

In one aspect of the invention, the DE-hep cells or cell nuclei exhibit at least one such as e.g. at least four, at least six, at least eight, at least ten or all of the following characteristics; glucose 6 phosphatase, apolipoprotein E, CYP7A1 (cholesterol 7a hydroxylase), alcohol dehydrogenase 1, cytochrome P450 reductase, HNF4a, alpha-1-antitrypsin, CK18, HNF3b (HNF3B), albumin or Liver-Fatty-Acid-Binding-Protein and at least two, such as e.g. at least four, at least six, at least eight, at least ten or all of the following eleven characteristics A. Drug Transporters
  i) at least 1% of the cells or, if relevant, cell nuclei exhibit protein and/or gene expression of BSEP,
  ii) at least 1% of the cells or, if relevant, cell nuclei exhibit protein and/or gene expression of MRP2,
  iii) at least 1% of the cells or, if relevant, cell nuclei exhibit protein and/or gene expression OATP-2 (=OATP-C, OATP1B1) and/or OATP-8 (OATP1B3), iv) at least 1% of the cells or, if relevant, cell nuclei exhibit protein and/or gene expression OATP-A (=OATP1A2)
  v) at least 1% of the cells or, if relevant, cell nuclei exhibit protein and/or gene expression NTCP,
  vi) at least 1% of the cells or, if relevant, cell nuclei exhibit protein and/or gene expression MDR1,
  vii) at least 1% of the cells or, if relevant, cell nuclei exhibit protein and/or gene expression MDR3,
  viii) at least 1% of the cells or, if relevant, cell nuclei exhibit protein and/or gene expression OCT-1

B. Drug Metabolising Enzymes
  ix) at least 20% of the cells or, if relevant, cell nuclei exhibit protein and/or gene expression of GST A1-1 and/or GSTM1-1,
  x) at least 5% of the cells or, if relevant, cell nuclei exhibit protein and/or gene expression of at least 2 of the following CYPs-1 A1, -1A2, -1B1, -2A6, -2B6, -2C8, -2C9, -2C19, -2D6, -2E1, -3A4, -3A7 and -7A1,
  xi) at least 5% of the cells or, if relevant, cell nuclei exhibit protein and/or gene expression of UGT1A6 and/or UGT2B7.

In particular, the invention relates to DE-hep cells exhibiting all of the following characteristics; glucose 6 phosphatase, apolipoprotein E, CYP7A1 (cholesterol 7α hydroxylase), alcohol dehydrogenase 1, cytochrome P450 reductase, HNF4a, alpha-1-antitrypsin, CK18, HNF3b (HNF3B), albumin or Liver-Fatty-Acid-Binding-Protein. These characteristics indicate that the cells are liver cells.

Moreover, as mentioned above, the DE-hep cells have characteristic with respect to drug transport and drug metabolism. Accordingly, a cell population comprising DE-hep cells normally has the following characteristics at least 20% of the cells exhibit protein expression of OATP-2, CYP1A2, CYP2C9, CYP2C19, CYP2D6, CYP3A4.

A cell population comprising DE-hep cells is normally a population, wherein at least 20% of the cells exhibit protein and/or gene expression of at least 5, preferably 7, even more preferred all of the following markers for drug transport: BSEP, MRP2, OATP-2 (=OATP-C, OATP1B1), OATP-8 (OATP1B3), OATP-A (=OATP1A2), NTCP, MDR1, MDR3, OCT-1, and at least 20% of the cells exhibit protein and/or gene expression of GST A1-1 and/or GSTM1-1, and at least 20% of the cells exhibit protein and/or gene expression of at least 7, preferably 9, even more preferred all of the following CYPs-1A1, -1A2, -1B1, -2A6, -2B6, -2C8, -2C9, -2C19, -2D6, -2E1, -3A4, -3A7 and -7A1, at least 5% of the cells exhibit protein and/or gene expression of UGT1A6 and/or UGT2B7.

Human blastocysts-derived stem cells (hBS cells) are pluripotent and can give rise to cells of all three embryonic germ layers; endoderm, ectoderm and mesoderm, and further on to all somatic and germ cells. Thus, in the future, differentiated cells derived from hBS cells with functional characteristics of hepatic cells do not only have the potential of being used for transplantation or in bioreactors for extra corporal liver support in patients with liver failure, but also as a test system for studying drug targets, hepatic metabolism of xenobiotics, and hepatotoxicity. hBS derived hepatocytes can potentially provide an unlimited source of functional human hepatocytes, from the same genetic donor if desired, and thereby improve the predictability of in vitro testing such as toxicity tests and reduce the need for animal experimentation. However, the toxicity of xenobiotics is often dependent on their biotransformation into toxic and reactive metabolites and, therefore, the presence and distribution of biotransforming systems are required. At present, primary human hepatocytes constitute a model for in vitro drug metabolism and toxicity testing. Nevertheless, the activity of drug metabolizing enzymes and many transporter functions are rapidly lost and/or changed when primary hepatocytes are cultured. Moreover, many of the hepatoma cell lines, e.g. HepG2, which are used for in vitro studies, lack expression of many important drug metabolizing enzymes.

Cytochrome P450s (CYPs) are mixed function mono-oxygenases and the major enzymes in phase I metabolism of xenobiotics. This oxidative metabolism results in, depending on the nature of the xenobiotic, inactivation and facilitated elimination, activation of pro-drugs or metabolic activation. The major site of CYP expression is the liver and CYP3A4 is the most abundant CYP isozyme in human adult liver. The enzymes of greatest importance for drug metabolism belong to the families 1-3, responsible for 70-80% of all phase I dependent metabolism of clinically used drugs. CYP expression and activity present large inter-individual variations due to polymorphisms. Moreover, CYPs can be induced several fold or inhibited by specific drugs, resulting in additional, although transient, variability of metabolic activity. Notably, the composition of the three major CYP families (1-3) basal CYP-activity within a hepatocyte is of great importance for drug metabolism. In the examples herein is described hBS cell derived DE-Hep cells in which mRNA from all tested CYP enzymes including CYP1A2 (an adult liver-specific enzyme), CYP2C9 and CYP3A4 were detected. Basal CYP activity of the major CYP families, more precisely CYP1A2, CYP2C9 and CYP3A4, were detected and in addition the inter-individual composition of the activity of the three mentioned CYPs was similar to that of human primary hepatocytes. Besides CYP1A2 also another adult liver-specific enzyme, namely CYP7A1 (cholesterol 7α hydroxylase), is expressed in DE-Hep cells confirming their adult hepatic phenotype. Accordingly, the present invention provides methods for the preparation of DE-Hep cells that express functional drug metabolising enzymes.

Besides phase I enzymes like CYPs, hepatic cells express phase II enzymes like UGTs. Accordingly, the present invention provides methods for the preparation of DE-Hep cells that express phase II enzymes. In a further aspect of the invention the DE-hep cells expresses both phase I enzymes and phase II enzymes, especially CYP2C9, CYP2C19, CYP2D6 together with UGT1A6, and/or UGT1A.

Furthermore, hepatic cells express Cytochrome P reductase which is an important redox-partner for CYPs and therefore essential for CYP functionality. Accordingly, the present invention provides methods for the preparation of DE-Hep cells that express Cytochrome P reductase.

Functional drug transporters such as BSEP, MRP2, OATPs (such as OATP-2), MDR1 and 3, NTCP and OCT-1 in hepatocytes are essential when analysing drug metabolism and toxicity of the liver. Accordingly, the present invention provides methods for the preparation of DE-Hep cells that express functional transporters.

Thus, the DE-hep may in one embodiment express phase I enzymes, phase II enzymes, and drug transports selected from the group comprising CYP2C9, CYP2C19, CYP2D6, UGT1A6, UGT1A, OATP-2, MRD3, and/or BSEP, together with other liver-markers such as e.g. alcohol dehydrogenase I a (ADH1A), and/or Albumin.

Expression of liver-related transcription factors like HNF1α, 3α, 3β, 4α, and 6, PXR, CAR, FXR, RXR, C/EBP A and B is essential for obtaining an adult hepatic phenotype. Accordingly, the present invention provides methods for the preparation of DE-Hep cells that express such transcription factors.

Thus, the present invention relates to a method for the preparation of DE-Hep progenitor cells from human blastocyst-derived stem (hBS) cells via definitive endoderm. The invention also relates to DE-Hep progenitor cells as such and the DE-Hep cells as such.

DE-Hep progenitor cells according to the present invention exhibit gene expression of one or more of EpCAM, HNF1, HNF3b, HNF4a, AFP, Desmin, CD133, c-kit, Notch2, ICAM1 (=CD54), CK7, CK8, CK18 and CK19 (see Example 8, Table 2, and Example 9).

DETAILED DESCRIPTION OF THE INVENTION

Definitions and Abbreviations

As used herein, the term "blastocyst-derived stem cell" is denoted BS cell, and the human form is termed "hBS cells". In literature the cells are often referred to as embryonic stem cells, and more specifically human embryonic stem cells.

As used herein;

The product of stage I: Definitive endoderm (DE) cells,

The product of stage II: DE-Hep progenitors, e.g. hepatoblast-like cells derived via definitive endoderm.

The product of stage III: DE-Hep cells, e.g. functional hepatocyte-like cells derived via definitive endoderm.

By the term "at least xx % of the cells or, if relevant, cell nuclei exhibit protein and/or gene expression of yy" is intended to mean that "at least xx % of the cells exhibit protein and/or gene expression of yy or "at least xx % of the cell nuclei exhibit gene expression of yy"

By the term "intrinsic differentiation" is intended to mean hepatocyte-like cells derived form hBS cells that have been cultured on MEFs in VitroHES™ without specific supplements (such as Activin A) but bFGF added to the culture medium and sparse medium changes (cf patent application WO2007/140968A1).

By the term "functional hepatic cells" is intended to mean a cell type which is expressing mature hepatic markers such as Albumin, CYP3A4, UGT2B7, OATP-2, ADH1A, UGT1A6, CYP2C9, CYP2C19 and CYP2D6 amongst others.

The metabolism of xenobiotics in the liver is often divided into three phases: modification (phase I), conjugation (phase II), and excretion (phase II). These reactions act in concert to detoxify xenobiotics and remove them from cells.

In phase I, a variety of enzymes acts to introduce reactive and polar groups into their substrates. One of the most common modifications is hydroxylation catalysed by the cytochrome P-450-dependent mixed-function oxidase system.

As used herein "CYP" is intended to mean Cytochrome P, and more specifically Cytochrome P 450, the major phase I metabolizing enzyme of the liver constituting of many different isoenzymes, such as CYP1A1, CYP1A2, CYP1B1, CYP2A6/2A7/2A13, CYP2B6, CYP2C8, CYP2C9, CYP2C19, CYP2D6, CYP2E1, CYP3A4, CYP3A5, CYP3A7 and CYP7A1.

The phase II reactions in the liver are catalysed by a large group of broad-specificity transferases, which in combination can metabolise almost any hydrophobic compound that contains nucleophilic or electrophilic groups. One of the most important of these groups are the glutathione S-transferases (GSTs), and uridine diphosphoglucuronosyltransferase (UGTs).

As used herein, the term "GST" is intended to mean glutathione transferase, and examples of subtypes thereof are GST A1-1, GST M1-1, and GST P1-1.

As used herein the term "UGT" is intended to mean uridine diphosphoglucuronosyltransferase, which is a group of liver enzymes catalyzing glucuronidation activities After phase II reactions the liver may further metabolise products from the phase II reactions. Conjugates and their metabolites can be excreted from cells in phase III of their metabolism, with the anionic groups acting as affinity tags for a variety of membrane transporters of the multidrug resistance protein (MRP) family. These proteins are members of the family of ATP-binding cassette transporters and can catalyse the ATP-dependent transport of a huge variety of hydrophobic anions, and thus act to remove phase II products to the extracellular medium, where they may be further metabolised or excreted.

As used herein the term "OATP" is intended to mean Organic Anion Transporting polypeptide, that mediate the sodium (Na+)-independent transport of organic anions, such as sulfobromophthalein (BSP) and conjugated (taurocholate) and unconjugated (cholate) bile acids (by similarity) in the liver. Three important members of the OATP family are OATP-2 (sometimes referred to as OATP-C or OATP1B1), OATP-8 (sometimes referred to as OATP1B3) and OATP-A (sometimes referred to as OATP1A2).

As used herein, the term "Cytochrome P450 reductase" (also known as CPR) is intended to mean a protein which physiological function is the reduction of Cytochrome P450 enzymes by electron transfer and which is therefore required for Cytochrome P450 enzyme-mediated reactions.

By the term "functional drug metabolising enzymes" is intended to mean functional enzymes belonging to the phase I and phase II enzymes that perform chemical modifications of xenobiotics and drugs, so called drug or xenobiotic metabolism.

As used herein, the term "functional activity" means effective measurable hepatic cell function, such as a measurable transportation of drugs for drug transporters and a measurable metabolism of enzymes for the Cytochrome P450s (CYPs), commonly detected in primary human hepatocytes.

As used herein, the term "extraembryonic endoderm (ExE)" is intended to mean the differentiated endodermal cells that, as to the opposite of the definitive endoderm, will constitute the compartments outside the embryo in the human development, such as the yolk sac.

As used herein, the term "AAT" is intended to mean the liver marker alpha-anti-trypsin.

As used herein, the term "Apolipoprotein E" is intended to mean a type of lipoprotein which carries cholesterol and other fats through the bloodstream as small vesicles. and are essential for the normal breakdown of these molecules. Apolipoprotein E is a major component of specific lipoproteins called very low-density lipoproteins which have the major function to remove excess cholesterol from the blood and carry it to the liver for processing.

As used herein, the term "Alcohol dehydrogenase 1" is intended to mean a type of dehydrogenase enzyme that facilitate the interconversion between alcohols and aldehydes or ketones with the reduction of $NAD^+$ to NADH. Alcohol dehydrogenase 1 serves to break down alcohols which could otherwise be toxic.

As used herein, the term "AFP" is intended to mean the liver marker alpha-fetoprotein.

As used herein, the term "BSEP" is intended to mean the bile transporter bile salt export pump.

As used herein, the term "CK" is intended to mean the liver marker cytokeratin (used interchangeably), with different subtypes such as Cytokeratin 18 (CK18), Cytokeratin 19 (CK19), Cytokeratin 8 (CK8) and Cytokeratin 7 (CK7).

As used herein, the term "c-Met" is intended to mean hepatocyte growth factor and/or scatter factor receptor.

As used herein, the term "Glucose 6 phosphatase" is intended to mean an enzyme in the gluconeogenesis pathway that dephosphorylates glucose 6-phosphate so that the free glucose can be exported from the cell via glucose transporter membrane proteins. Glucose 6-phosphatase is found in the liver and kidney and is involved in the organs' role in glucose homeostasis.

As used herein, the term "ICAM-1" is intended to mean intercellular adhesion molecule 1 (sometimes referred to as CD54).

As used herein, the term "LFABP" means Liver-Fatty-Acid-Binding-Protein (used interchangeably).

As used herein, the term "EpCAM" means Epithelial Cell Adhesion Molecule (used interchangeably).

As used herein, the term "FGF" means fibroblast growth factor, preferably of human and/or recombinant origin, and subtypes belonging thereto are e.g. "bFGF" (means basic fibroblast growth factor, sometimes also referred to as FGF2) and FGF4. "aFGF" means acidic fibroblast growth factor (sometimes also referred to as FGF1).

As used herein, the term "BMP" means Bone Morphogenic Protein, preferably of human and/or recombinant origin, and subtypes belonging thereto are e.g. BMP4 and BMP2.

As used herein, the term "HGF" means Hepatocyte Growth Factor, preferably of human and/or recombinant origin.

As used herein, the term "Dex" means Dexamethasone.

As used herein, the term "OSM" means Oncostatin M.

As used herein, the term "ITS mixture" means insulin-transferrin-selenium mixture e.g. Insulin-Transferrin-Selenium-A Supplement (100×) from Invitrogen (Catalog Number-51300-044).

As used herein, the term "DMSO" means dimethylsulfoxide.

As used herein the "HNF3beta", and/or "HNF3b", used interchangeably are intended to mean hepatocyte nuclear factor 3, a transcription factor regulating gene expression in endodermal derived tissue, e.g. the liver, pancreatic islets, and adipocytes. HNF3beta may sometimes also be referred to as HNF3b or Fox2A the latter name originating from the transcription factor being a member of Forkhead box transcription factors family.

As used herein the "HNF4alpha", and/or "HNF4a", used interchangeably are intended to mean hepatocyte nuclear factor 4 alpha, a transcription factor which is critical for liver development, hepatocyte-specific gene expression and the regulation of pancreatic beta-cell gene expression.

As used herein the term "NTCP" is intended to mean sodium taurocholate co-transporting polypeptide and is a transporter taking up bile acids from the portal circulation into hepatocytes. This uptake of bile acids is an important component of the entero-hepatic recirculation of bile acids and thus critical for adequate bile flow and normal liver function.

As used herein the term "OCT-1" is intended to mean organic cation transporter 1. OCT-1 is a major hepatic transporter that mediates the uptake of many organic cations from the blood into the liver where the compounds may be metabolized or secreted into the bile.

As used herein the term "MDR" is intended to mean multidrug resistance transporter. MDR 1 and 3 are members of the ATP-binding cassette (ABC) family of transporters and both are drug efflux transporters. MDR 1 is important in regulating the traffic of drugs, peptides and xenobiotics into the body and in protecting the body against xenobiotic insults and drug toxicity, while MDR 3 is essential for phospholipid secretion into bile.

As used herein the term "Wnt3a" is intended to mean wingless-related MMTV integration site 3A.

As used herein the term "Activin" is intended to mean TGF-beta family members that exhibiting a wide range of biological activities including regulation of cellular proliferation and differentiation such as "Activin A" or "Activin B". Activin belongs to the common TGF-beta superfamily of ligands.

As used herein the term "xeno-free" is intended to mean complete circumvention of direct or in-direct exposure to non-human animal components.

As used herein the term "differentiation inducer" is intended to mean any type of factor inducing cell differentiation, including but not limited to chemicals, biologicals and components in the physical microenvironment surrounding the cells; notably the term is used for extrinsic factors, i.e. factors supplied to the culture.

As used herein, the term "intrinsic factor protocol" indicates that the differentiation is induced by exposure to intrinsic factors secreted to the culture medium. The following protocol can be employed: hBS cells are grown of mEF cell layers in IVF culture dishes (Falcon) and subjected to differentiation under 37° C., 5% CO2, and 95% humidity for up to 40 days to obtain hepatocyte-like cells. The culture medium used (VitroHES™ [Vitrolife AB] with 4 ng/ml of human recombinant bFGF [Invitrogen] added) is changed between every 7 and 21 days, normally every 14 days by discarding approximately 1 to 2 ml of old medium and adding 1 to 2 ml of fresh medium.

Feeder Cells

As used herein feeder cells are intended to mean supporting cell types used alone or in combination. The cell type may further be of human or other species origin. The tissue from which the feeder cells may be derived include embryonic, fetal, neonatal, juvenile or adult tissue, and it further includes tissue derived from skin, including foreskin, umbilical chord, muscle, lung, epithelium, placenta, fallopian tube, glandula, stroma or breast. The feeder cells may be derived from cell types pertaining to the group consisting of human fibroblasts, fibrocytes, myocytes, keratinocytes, endothelial cells and epithelial cells. Examples of specific cell types that may be used for deriving feeder cells include embryonic fibroblasts, extraembryonic endoderm cells, extraembryonic mesoderm cells, fetal fibroblasts and/or fibrocytes, fetal muscle cells, fetal skin cells, fetal lung cells, fetal endothelial cells, fetal epithelial cells, umbilical chord mesenchymal cells, placental fibroblasts and/or fibrocytes, placental endothelial cells, post-natal foreskin fibroblasts and/or fibrocytes, post-natal muscle cells, post-natal skin cells, post-natal endothelial cells, adult skin fibroblasts and/or fibrocytes, adult muscle cells, adult fallopian tube endothelial cells, adult glandular endometrial cells, adult stromal endometrial cells, adult breast cancer parenchymal cells, adult endothelial cells, adult epithelial cells or adult keratinocytes. When feeder cells are derived from hBS cells, the cells may be fibroblasts.

In the methods according to the invention (i.e. any of Stage I-III) feeder cells such as human or mouse feeder cells may be used or the method may be without any use of feeder cells. In a specific embodiment the culturing is xeno-free. In another specific embodiment (e.g. when the DE-Hep cells are used for therapeutic purposes, the cells may be autologous cells, i.e. derived from the subject who is treated).

As used herein, the term "MEF cells" is intended to mean mouse embryonic fibroblasts.

In the present invention cell culture medias specifically considered to support hepatocyte growth are used in the present invention, such as HCM (Hepatocyte Culture Medium) medium, Williams E medium and RPMI Advanced medium.

As it appears from the examples herein, the present invention relates to a stage-divided method for the preparation of i) DE-Hep progenitors (result of stage II) and ii) DE-Hep cells (mature DE-Hep progenitors and result of stage III, see also FIG. 1 A and B).

DE-Hep Progenitors

The DE-Hep progenitors and DE-Hep cells according to the present invention can advantageously be used for treatment and/or prevention of several hepatic diseases and disorders. Accordingly, the DE-Hep progenitors and the DE-Hep cells according to the present invention can be used in a medicament.

The DE-Hep progenitor cells are the progenitor cells of DE-Hep cells, and accordingly, they are suitably used e.g. for obtaining metabolically competent hepatocyte-like cells derived from definitive endoderm, or for studying the maturation towards hepatocyte-like cells.

As it will appear from the below description, the present invention also relates to a stage-divided method for the preparation of i) DE-Hep progenitors and ii) DE-Hep cells, which are mature DE-Hep cells. This method, as illustrated in FIG. 1, involves the formation of DE cells by culturing hBS cells (stage I), thereafter obtaining DE-hep progenitor cells from the DE cells (stage II), and finally the formation of mature DE-Hep cells (stage III) from the progenitor DE-hep cells.

Stage I

The DE cells are normally obtained by culturing hBS cells in a culture medium comprising Activin A and optionally one or more growth factors, such as FGF2 and serum, notably FCS. Other suitable substances, such as Wnt3a, may also be included.

The method comprises subjecting hBS cells to culturing conditions, wherein the hBS cells are induced to develop into definitive endodermal cells. Stage I comprises 2-6 days of culturing of the hBS cells in a first stage I culture medium comprising activin, wherein the medium after 1-2 days of culturing is replaced by a second stage I culture medium comprising activin, one or more growth factors and, in a preferred embodiment, serum. Activin A can in some circumstances be replaced by similar substances such as Activin B or Follistatin.

Both the first and/or second stage I culture medium may be RPMI advanced medium or DMEM medium. This first and/or second stage I culture medium may further be supplemented with one or more growth factors, notably FGF2 and/or Wnt3a, and serum, notably fetal bovine serum (abbreviated as FBS or FCS used interchangeably herein), as shown in protocol 1, Example 2 of the present invention.

As shown in Example 2 (protocol 1-4) the hBS cells may be cultured according to one of the following schemes:

Day 1: The first stage I culture medium contains Activin (e.g. Protocol 1),
Day 1: The first stage I culture medium contains Activin and a growth factor, notably FGF2 (e.g. Protocol 2 and 3),
Day 1: The first stage I culture medium contains Activin (e.g. Protocol 4).
Day 2: The second culture medium contains Activin and serum (e.g. Protocol 1), and optionally FGF2.
Day 2: The second culture medium contains Activin, serum and a growth factor, notably FGF2 (e.g. Protocol 2, 3 and 4).
Days 3 and 4: The second culture medium contains Activin, FGF2 and serum (e.g. Protocol 1).
Days 3 and 4: The second culture medium contains Activin, serum and a growth factor, notably FGF2 (e.g. Protocol 2, 3 and 4).

The concentration of Activin supplied to the hBS cells at any given above-mentioned culture media may be in the range of about 80-120 ng/ml, such e.g. 90-110 ng/ml, 95-105 ng/ml or 100 ng/ml. The concentration of Wnt3A will preferably be at about 20 ng/ml, such as e.g. 25 ng/ml, 30 ng/ml. Most preferred is a concentration of 25 ng/ml.

The concentration serum, such as FBS, may be in the rage of about 0% to 10%, such as e.g. 0.1-5%, or 0.2-3%. As shown in FIG. 1B the concentration of serum may be varied during stage 1, e.g. by having 0% serum the first stage I culture medium, for example followed by a 0.2% serum concentration in the second stage I culture medium, and in some circumstances even further increased to e.g. 1% FBS as shown for protocol 4 in FIG. 1 B.

Stage II—DE-Hep Progenitors

The present invention relates to a method for the preparation of DE-Hep progenitor cells derived from human blastocyst-derived stem (hBS) cells via definitive endoderm.

At stage II, the cells obtained from stage I are propagated, and stage II comprises culturing the cells from stage I in a stage II culture medium comprising one or more of a growth factor and optionally a bone morphogenic protein, and optionally harvesting the thus obtained DE-hep progenitor cells.

Normally, the culturing is performed in a culture medium such as RPMI advanced medium or DMEM medium, HCM medium, William E based medium or VitroHES® or the like. The culture medium is normally supplemented with various factors such as growth factors. FGF2, PEST, and/or GlutaMAX are examples of substances that suitably are included in a culture medium.

The medium is suitably changed such as, e.g., every day or every second day.

Moreover, the medium may comprise one or more of a growth factor, notably aFGF, and a bone morphogenic protein, notably BMP2.

In a specific embodiment, the medium further comprises serum replacement or serum such as, e.g., FBS and in another specific embodiment the medium may further comprises HGF.

In specific embodiments, the DE-Hep progenitors are obtained by the following method, wherein the DE cells are obtained by the method described above, are cultivated according to the following scheme, as shown in Example 2 (protocol 1-4):

Days 1 to day 4 of stage II: the stage II culture medium contains FGF2, BMP4, one or more further bone morphogenetic proteins, notably BMP2, serum, notably FBS, PEST, and GlutaMAX and, optionally, one or more further growth factors, notably aFGF (e.g. Protocol 1), Days 1 to 8 of stage II: the stage II culture medium contains HGF (e.g. Protocol 2), Days 1 to 5 of stage II: the stage II culture medium contains FGF4, BMP2, (e.g. Protocol 3), Days 1 to 3 of stage II: the stage II culture medium contains FGF2, BMP4, serum, notably FBS, (e.g. Protocol 4), Days 4 to 10 of stage II: the stage II culture medium contains FGF2, BMP4, serum, notably FBS, and HGF (e.g. Protocol 1), Days 6 to 10 of stage II: HGF (e.g. Protocol 3), Days 4 to 8 of stage II: the stage II culture medium contains HGF, FGF2, EGF and serum e.g. FBS (Protocol 4)

The cells in stage II preferably cultivated for 8 days, the concentration of serum e.g. FBS is increased at day 6 and a supplement of a growth factor, notably EGF, is given at day 6 and the medium was changed every day from day 6 to day 8.

As shown in Examples the concentration and the preferred embodiments may include:

Protocol 1

RPMI advanced medium or DMEM medium supplemented with 1% PEST, 1% Glutamax and additionally with;

Day 5: aFGF, bFGF, BMP2, BMP4 (100 ng/ml, 5 ng/ml, 50 ng/ml, 200 ng/ml, respectively) 0.2% FCS.

Day 6: aFGF, bFGF, BMP2, BMP4 (100 ng/ml, 5 ng/ml, 50 ng/ml, 200 ng/ml, respectively) 0.2% FCS.

Day 7: bFGF, BMP4, HGF (50 ng/ml, 200 ng/ml, 50 ng/ml, respectively) 0.2% FCS.

Day 8: bFGF, BMP4, HGF (50 ng/ml, 200 ng/ml, 50 ng/ml, respectively) 0.2% FCS.

Day 9: bFGF, BMP4, HGF (50 ng/ml, 200 ng/ml, 50 ng/ml, respectively) 0.2% FCS.

A relatively high HGF concentration (100-200 ng/ml) may be used for the first days.

Optionally day 6-13 may be;

Day 6: BMP4 (50 ng/ml), FGF2 (4 ng/ml), 0.2% FCS,

Day 7: BMP4 (50 ng/ml), FGF2 (4 ng/ml), 0.2% FCS

Day 8-9: FGF1 (50 ng/ml), FGF2 (4 ng/ml), 1% FCS

Day 10: HGF, FGF2 (50 ng/ml, 4 ng/ml, respectively), 1% FCS

Day 11-13: HGF, FGF2, EGF (50 ng/ml, 4 ng/ml, 10 ng/ml, respectively), 1% FCS

Wherein a higher FCS concentration and a supplement of EGF (10 ng/ml) at day 11 to 13 may be given.

Alternatively BMP4, FGF2 (50 ng/ml, 4 ng/ml, respectively) 0.2% FCS may be used for days 6-7, followed by aFGF, FGF2 (50 ng/ml, 4 ng/ml, respectively) 1% FCS at days 8-9 and HGF, FGF2, EGF (50 ng/ml, 2 ng/ml, 10 ng/ml, respectively) 1% FCS at days 9-10.

In another embodiment HCM medium or a Williams E based medium supplemented with 1% PEST, 1% Glutamax and additionally with HGF (20 ng/ml) and 0% FCS may be used, wherein the concentration of HGF is about 20 ng/ml at day 6-12. Alternatively, day 6-15 may be varied by (protocol 3) using FGF4, BMP2 (30 ng/ml, 20 ng/ml, respectively) 0% FCS at day 6-9, and HGF (20 ng/ml) 0% FCS at day 10-15.

From the above, it is seen that the concentration of aFGF is in the range of from about 50 to about 200 ng/ml, bFGF is from about 2-50 ng/ml), BMP2 is from about 25-100 ng/ml, BMP4 is from 25-300 ng/ml (in general, higher concentrations are employed in the beginning of the Stage than later on), HGF is from about 25-300 ng/ml), FGF2 is from about 1 to about 10 ng/ml, FGF1 is from about 25 to about 100 ng/ml, EGF is from about 5-50 ng/ml), FCS is from about 0.1%-5%, when present.

Another embodiment of protocol 1 may include

Day 1: Activin A, bFGF (100 ng/ml, 5 ng/ml).

Day 2-5: Activin A, bFGF (100 ng/ml, 5 ng/ml), 0.2% FCS.

Day 5-7: no medium change.

Day 8-14: aFGF, bFGF, BMP2, BMP4 (100 ng/ml, 5 ng/ml, 50 ng/ml, 200 ng/ml), 0.2% FCS.

Day 15-21: WME+SQ supplemented with bFGF, HGF (2 ng/ml, 20 ng/ml).

Wherein WME+SQ supplemented with Dex, OSM bFGF, HGF (100 nM, 10 ng/ml, 2 ng/ml, 2 ng/ml).

Wherein Williams medium E, and SQ is SingleQuots containing glutamic acid, ascorbic acid, bovine serum albumin, hydrocortisone, transferrin, insulin.

Characterisation of DE-Hep Progenitors

As shown in the examples herein the DE-Hep progenitor cells obtained exhibit gene expression of one or more, such as e.g. two or more, four or more, six or more, eight or more, ten or more, twelve or more or all of EpCAM, HNF1, HNF3b, HNF4a, Desmin, CD133, c-kit, CAM1 (=CD54), CK8, CK18 and CK19 (see Example 7, Table 2, and Example 8).

More details with respect to the characterisation of DE-hep progenitors appear from the paragraph "Brief description of the invention", the Examples herein and the appended figures.

Stage III

As described herein before, a method of the present invention also provides DE-Hep cells, i.e. hepatocytes-like cells derived from DE cells via hBS cells. In order to obtain such cells, a further stage is included in the methods described above, namely a stage III. Stage III relates to culturing the DE-Hep progenitor cells obtained as described in Stage II (and optionally Stage I) in a culture medium like e.g. a Williams E based medium, Leibovitz L-15 medium or HCM Cambrex medium or a comparable medium optionally supplemented with a differentiation and/or CYP inducer such as, e.g., DMSO, dexamethazone, omeprazole, rifampicin, desoxyphenobarbital, ethanol, isoniazide, alone or in combination;

an ITS mixture;

a BMP and/or TGFP, an OSM and/or EGF, notably BMP4 and/or HGF.

In Stage III the culturing is normally carried out for 10-25 days or more.

The culture medium is normally changed every day up to day 15 and, if relevant, changed every second day for the remaining culture period.

A method for preparation of DE-hep progenitors, and DE-hep cells, includes the appropriate stages described above.

For all embodiments, the starting material, as described in Example 1 herein, may suitably be undifferentiated human blastocyst-derived stem cells, obtained in the following four different ways, described in detail in the following patent applications;

1. hBS cell line establishment and LOT preparation (WO03055992)

2. hBS cells transferred to a feeder-free culture system (WO2004099394)

3. Xeno-free preparation (WO2007042225)

4. Enzymatically passaged hBS cells (WO07107303)

The xeno-free preparation is especially important when the DE-hep cells are used for therapeutic purposes.

In particular, the hBS cells or cell lines recommended as starting material have the following characteristics: positive for alkaline phosphatase, SSEA-3, SSEA-4, TRA 1-60, TRA 1-81, Oct-4, negative for SSEA-1, telomerase activity, and pluripotency in vitro and in vivo (the latter shown by teratoma formation in immuno-deficient mice).

The undifferentiated hBS cells, as described above, may thus be used in any of the mentioned embodiments of the invention, which further includes the following specific five embodiments:

Embodiment 1

| Days | Stage | Media |
|---|---|---|
| 1 | I | RPMI advanced medium, DMEM medium, HCM or HBM medium, William E based medium or VitroHes ® supplemented with<br>FGF2, 2-6 ng/ml, notably 4 or 5 ng/ml,<br>Activin A, Wnt3A (90-110 ng/ml (preferably 100 ng/ml)), 25 ng/ml) 0% FCS |
| 2-4 | I | RPMI advanced medium, DMEM medium, HCM or HBM medium, William E based medium or VitroHes ® supplemented with<br>FGF2 2-6, ng/ml, notably 4 or 5 ng/ml,<br>Activin A (90-110 ng/ml (preferably 100 ng/ml)) 0.1-0.5% FCS (preferably 0.2%) |
| 5-6 | II | RPMI advanced medium, DMEM medium, HCM or HBM medium, William E based medium or VitroHes ® supplemented with<br>aFGF, bFGF, BMP2, BMP4 (90-110 ng/ml, 2-6 ng/ml, 40-60 ng/ml, 190-210 ng/ml, respectively; preferably 100 ng/ml, 4 ng/ml, 50 ng/ml, 200 ng/ml, respectively) 0.1-0.5% FCS (preferably 0.2%) |
| 7-9 | II | RPMI advanced medium, DMEM medium, HCM or HBM medium, William E based medium or VitroHes ® supplemented with<br>bFGF, BMP4, HGF (40-60 ng/ml, 190-210 ng/ml, 40-60 ng/ml, respectively; preferably 50 ng/ml, 200 ng/ml, 50 ng/ml, respectively) 0.1-0.5% FCS (preferably 0.2%) |
| 10-20 (or optionally 9-25 or 9-18) | II | RPMI advanced medium, DMEM medium, HCM or HBM medium, William E based medium or VitroHes ® supplemented with<br>bFGF, BMP4, HGF (40-60 ng/ml, 190-210 ng/ml, 40-60 ng/ml, respectively; preferably 50 ng/ml, 200 ng/ml, 50 ng/ml, respectively) 0.1-0.5% FCS (preferably 0.2%)<br>Optionally haversting of DE-progenitors |
| Day 1-4 after stage II | III | Williams E based medium or HCM or HBM medium supplemented with<br>OSM, Dex, ITS mixture, BMP4, HGF (8-12 ng/ml, $0.1-1 \times 10^{-7}$ M, 0.5-2x, 190-210 ng/ml, 40-60 ng/ml, respectively; preferably 10 ng/ml, $10^{-7}$ M, 1x, 200 ng/ml, 50 ng/ml, respectively), 0% FCS. |
| Optionally, day 6-11 after stage II | III | Williams E based medium supplemented with Sodium Butyrate, HGF (1-3 mM, 1-3 ng/ml, respectively; preferably 2.5 mM, 2.5 ng/ml, respectively) and 0% FBS,<br>HGF concentration (100-200 ng/ml) and Dexamethasone (Dex) (100 µM) |

Embodiment 2

| Days | Stage | Media |
|---|---|---|
| 1 | I | RPMI advanced medium, DMEM medium, HCM or HBM medium, William E based medium or VitroHes ® supplemented with<br>FGF2, 2-6 ng/ml, notably 4 or 5 ng/ml,<br>Activin A, Wnt3A (90-110 ng/ml (preferably 100 ng/ml)), 25 ng/ml) 0% FCS |
| 2-4 | I | RPMI advanced medium, DMEM medium, HCM or HBM medium, William E based medium or VitroHes ® supplemented with<br>FGF2 2-6, ng/ml, notably 4 or 5 ng/ml,<br>Activin A (90-110 ng/ml (preferably 100 ng/ml)) 0.1-0.5% FCS (preferably 0.2%) |
| 5 | II | RPMI advanced medium, DMEM medium, HCM or HBM medium, William E based medium or VitroHes ® supplemented with<br>aFGF, bFGF, BMP2, BMP4 (90-110 ng/ml, 2-6 ng/ml, 40-60 ng/ml, 190-210 ng/ml, respectively; preferably 100 ng/ml, 4 ng/ml, 50 ng/ml, 200 ng/ml, respectively) 0.1-0.5% FCS (preferably 0.2%) |
| 6-7 | II | RPMI advanced medium, DMEM medium, HCM or HBM medium, William E based medium or VitroHes ® supplemented with<br>BMP4 (40-60 ng/ml, preferably 50 ng/ml), FGF2 (2-6 ng/ml, preferably 4 ng/ml), 0.1-0.5% FCS, preferably 0.2% FCS |

Embodiment 2

| Days | Stage | Media |
|---|---|---|
| 8-9 | II | RPMI advanced medium, DMEM medium, HCM or HBM medium, William E based medium or VitroHes ® supplemented with FGF1 (40-60 ng/ml, preferably 50 ng/ml), FGF2 (2-6 ng/ml, preferably 4 ng/ml), 0.5-2% FCS, preferably 1% FCS |
| 10 | II | RPMI advanced medium, DMEM medium, HCM or HBM medium, William E based medium or VitroHes ® supplemented with HGF, FGF2 (40-60 ng/ml, 2-6 ng/ml, respectively; preferably 50 ng/ml, 4 ng/ml, respectively), 0.5-2% FCS, preferably 1% FCS |
| 11-13 | II | RPMI advanced medium, DMEM medium, HCM or HBM medium, William E based medium or VitroHes ® supplemented with HGF, FGF2, EGF (40-60 ng/ml, 2-6 ng/ml, 5-15 ng/ml, respectively; preferably 50 ng/ml, 4 ng/ml, 10 ng/ml, respectively), 0.5-2% FCS, preferably 1% FCS Optionally harvesting of DE-progenitors |
| Day 1-4 after stage II | III | Williams E based medium or HCM or HBM medium supplemented with OSM, Dex, ITS mixture, BMP4, HGF (8-12 ng/ml, $0.1-1 \times 10^{-7}$ M, 0.5-2x, 190-210 ng/ml, 40-60 ng/ml, respectively; preferably 10 ng/ml, $10^{-7}$ M, 1x, 200 ng/ml, 50 ng/ml, respectively), 0% FCS. |
| Optionally, day 6-11 after stage II | III | Williams E based medium supplemented with Sodium Butyrate, HGF (1-3 mM, 1-3 ng/ml, respectively; preferably 2.5 mM, 2.5 ng/ml, respectively) and 0% FBS, HGF concentration (100-200 ng/ml) and Dexamethasone (Dex) (100 μM) |

Embodiment 3

| Days | Stage | Media |
|---|---|---|
| 1 | I | RPMI advanced medium, DMEM medium, HCM or HBM medium, William E based medium or VitroHes ® supplemented with FGF2, 2-6 ng/ml, notably 4 or 5 ng/ml, Activin A (90-110 ng/ml (preferably 100 ng/ml)), 0% FCS |
| 2-3 | I | RPMI advanced medium, DMEM medium, HCM or HBM medium, William E based medium or VitroHes ® supplemented with FGF2 2-6, ng/ml, notably 4 or 5 ng/ml, Activin A (90-110 ng/ml (preferably 100 ng/ml)) 0.1-0.5% FCS (preferably 0.2%) |
| 4-5 | I | Additionally culturing the cell (in the medium used in day 2-3) without medium change |
| 6-12 | II | RPMI advanced medium, DMEM medium, HCM or HBM medium, William E based medium or VitroHes ® supplemented with HGF, 10-30 ng/ml, preferably 20 ng/ml, 0% FCS (medium change every 2-3 days) Optionally harvesting of DE-progenitors |
| Day 1-22 (up to 35-40 days) after stage II | III | 1. Williams E based medium or HCM or HBM medium supplemented with OSM, Dex, (8-12 ng/ml, $0.1-1 \times 10^{-7}$ M, respectively; preferably 10 ng/ml, $10^{-7}$ M, respectively), 0% FCS. Medium change every 2-3 days. OR 2. Williams E based medium or HCM or HBM medium supplemented with OSM, Dex, (8-12 ng/ml, $0.1-1 \times 10^{-7}$ M, respectively; preferably 10 ng/ml, $10^{-7}$ M, respectively), 0% FCS. Medium change every 2-3 days. Wherein EGF and ascorbic added are omitted. |

Embodiment 4

| Days | Stage | Media |
|---|---|---|
| 1 | I | RPMI advanced medium, DMEM medium, HCM or HBM medium, William E based medium or VitroHes ® supplemented with FGF2, 2-6 ng/ml, notably 4 or 5 ng/ml, Activin A (90-110 ng/ml (preferably 100 ng/ml)), 0% FCS |
| 2-3 | I | RPMI advanced medium, DMEM medium, HCM or HBM medium, William E based medium or VitroHes ® supplemented with FGF2 2-6, ng/ml, notably 4 or 5 ng/ml, Activin A (90-110 ng/ml (preferably 100 ng/ml)) 0.1-0.5% FCS (preferably 0.2%) |
| 4-5 | I | Additionally culturing the cells (in the medium used in day 2-3) without medium change |
| 6-9 | II | RPMI advanced medium, DMEM medium, HCM or HBM medium, William E based medium or VitroHes ® supplemented with FGF4, BMP2 (20-40 ng/ml, 10-30 ng/ml, respectively; preferably 30 ng/ml, 20 ng/ml, respectively) 0% FCS. Medium change every 2-3 days. |
| 10-15 | II | RPMI advanced medium, DMEM medium, HCM or HBM medium, William E based medium or VitroHes ® supplemented with HGF (10-30 ng/ml, preferably 20 ng/ml) 0% FCS. Medium change every 2-3 days. Optionally harvesting of DE-progenitors |
| Day 1-22 (up to 35-40 days) after stage II | III | 1. Williams E based medium or HCM or HBM medium supplemented with OSM, Dex, (8-12 ng/ml, $0.1-1 \times 10^{-7}$ M, respectively; preferably 10 ng/ml, $10^{-7}$ M, respectively), 0% FCS. Medium change every 2-3 days. OR 2. Williams E based medium or HCM or HBM medium supplemented with OSM, Dex, (8-12 ng/ml, $0.1-1 \times 10^{-7}$ M, respectively; preferably 10 ng/ml, $10^{-7}$ M, respectively), 0% FCS. Medium change every 2-3 days. Wherein EGF and ascorbic added are omitted. |

Embodiment 5

| Days | Stage | Media |
|---|---|---|
| 1 | I | RPMI advanced medium, DMEM medium, HCM or HBM medium, William E based medium or VitroHes ® supplemented with Activin A (90-110 ng/ml (preferably 100 ng/ml)), 0% FCS |
| 2-3 | I | RPMI advanced medium, DMEM medium, HCM or HBM medium, William E based medium or VitroHes ® supplemented with FGF2 2-6 ng/ml, notably 4 or 5 ng/ml, Activin A (90-110 ng/ml (preferably 100 ng/ml)) 0.1-0.5% FCS (preferably 0.2%) 50-100% of the medium changed every day |
| 4-5 | I | RPMI advanced medium, DMEM medium, HCM or HBM medium, William E based medium or VitroHes ® supplemented with FGF2 2-6 ng/ml, notably 4 or 5 ng/ml, Activin A (90-110 ng/ml (preferably 100 ng/ml)) 0.5-2% FCS (preferably 1%) 50-100% of the medium changed every day |
| 6-7 | II | RPMI advanced medium, DMEM medium, HCM or HBM medium, William E based medium or VitroHes ® supplemented with BMP4, FGF2 (40-60-40 ng/ml, 2-6 ng/ml, respectively; preferably 50 ng/ml, 4 ng/ml, respectively) 0.1-0.5% FCS (preferably 0.2%) 50-100% of the medium changed every day |
| 8-9 | II | RPMI advanced medium, DMEM medium, HCM or HBM medium, William E based medium or VitroHes ® supplemented with aFGF, FGF2 (40-60-40 ng/ml, 2-6 ng/ml, respectively; preferably 50 ng/ml, 4 ng/ml, respectively) 0.5-2% FCS (preferably 1%) 50-100% of the medium changed every day |
| 10-12 | II | RPMI advanced medium, DMEM medium, HCM or HBM medium, William E based medium or VitroHes ® supplemented with HGF, FGF2, EGF (40-60 ng/ml, 2-6 ng/ml, 5-15 ng/ml respectively; preferably 50 ng/ml, 4 ng/ml, 10 ng/ml, respectively) 0.5-2% FCS (preferably 1%)Medium change every 2-3 days. 50-100% of the medium changed every day Optionally harvesting of DE-progenitors |
| 13-14 | III | 1. Williams E based medium or HCM or HBM medium supplemented with OSM, ITS mixture, HGF (5-15 ng/ml, 0.5-2x, 40-60 ng/ml respectively; preferably 10 ng/ml, 1x, 50 ng/ml, respectively), 0% FCS 50 or 100% medium was change every 1-3 days OR 2. Williams E based medium or HCM or HBM medium supplemented with OSM, ITS mixture, HGF (5-15 ng/ml, 0.5-2x, 40-60 ng/ml respectively; preferably 10 ng/ml, 1x, 50 ng/ml, respectively), 0% FCS 50 or 100% medium was change every 1-3 days Wherein EGF and ascorbic added are omitted. |
| 15-30, preferably 15-26 | | Williams E based medium or HCM or HBM medium supplemented with OSM, ITS mixture, HGF, Dex (5-15 ng/ml, 0.5-2x, 40-60 ng/ml, 0.5-2x $10^{-7}$ M respectively; preferably 10 ng/ml, 1x, 50 ng/ml, $10^{-7}$ M respectively $10^{-7}$ M, respectively), 0% FCS 50 or 100% medium was change every 1-3 days |

The above-mentioned specific embodiments are illustrative of the present invention. It is contemplated that the individual ingredients may be replaced with other substance having the same functionality and that the deviation from the stated concentration ranges is possible and still obtain the desired result.

Characterisation of DE-Hep Cells Obtained from Stage III

The present invention also relates to DE-Hep cells obtained by the above-described Stage III, which exhibit increased protein and/or gene expression of albumin, UGT2B7, CYP3A4, ADH1A, OATP-2, UGT1A6, CYP2C9, CYP2C19 and CYP2D6 compared to cells prepared using the same kind of cells but subjecting the cells to intrinsic differentiation here we need a detailed description of the protocol used for the control experiments.

The present invention further relates to DE-hep cells wherein the increase in protein and/or gene expression of albumin and/or UGT2B7 and/or CYP3A4 is at least 2 fold such as, e.g., at least 5 fold, at least 10 fold, at least 20 fold, at least 30 fold, at least 40 fold or more compared to intrinsically differentiated cells.

The present invention further relates to DE-hep cells wherein the increase in protein and/or gene expression of ADH1A and/or OATP-2 and/or UGT1A6 and/or CYP2C9 and/or CYP2C19 and/or CYP2D6 is at least 2 fold such as, e.g., at least 5 fold, at least 10 fold, at least 20 fold, at least 30 fold, at least 40 fold or more compared to intrinsically differentiated cells.

In a specific embodiment the present invention relates to DE-hep cells wherein the increase in protein and/or gene expression of albumin is at least 5 fold, such as e.g. at least 10 fold, at least 15 fold, at least 20 fold or more and of UGT2B7 is at least 3, such as e.g. at least 5 fold, at least 10 fold, at least 15 fold or more compared to intrinsically differentiated cells.

More details with respect to the characterisation of DE-hep cells appear from the paragraph "Brief description of the invention", the Examples herein and the appended figures.

In a specific embodiment the present invention relates to DE-hep cells, wherein at least 20% of the cells or the cell nuclei in a cell population obtained exhibit at least one such as e.g. at least four, at least six, at least eight, at least ten or all of the following characteristics glucose 6 phosphatase, apolipoprotein E, CYP7A1 (cholesterol 7a hydroxylase), alcohol dehydrogenase 1, cytochrome P450 reductase, HNF4a, alpha-1-antitrypsin, CK18, HNF3b, albumin or Liver-Fatty-Acid-Binding-Protein and at least two, such as e.g. at least four, at least six, at least eight, at least ten or all of the following eleven characteristics A. Drug Transporters
  i) at least 1% of the cells or, if relevant, cell nuclei exhibit protein and/or gene expression of BSEP,
  ii) at least 1% of the cells or, if relevant, cell nuclei exhibit protein and/or gene expression of MRP2,
  iii) at least 1% of the cells or, if relevant, cell nuclei exhibit protein and/or gene expression OATP-2 (=OATP-C, OATP1B1) and/or OATP-8 (OATP1B3),
  iv) at least 1% of the cells or, if relevant, cell nuclei exhibit protein and/or gene expression OATP-A (=OATP1A2)
  v) at least 1% of the cells or, if relevant, cell nuclei exhibit protein and/or gene expression NTCP,
  vi) at least 1% of the cells or, if relevant, cell nuclei exhibit protein and/or gene expression MDR1,
  vii) at least 1% of the cells or, if relevant, cell nuclei exhibit protein and/or gene expression MDR3,
  viii) at least 1% of the cells or, if relevant, cell nuclei exhibit protein and/or gene expression OCT-1

B. Drug Metabolising Enzymes
  ix) at least 20% of the cells or, if relevant, cell nuclei exhibit protein and/or gene expression of GST A1-1 and/or GSTM1-1,
  x) at least 5% of the cells or, if relevant, cell nuclei exhibit protein and/or gene expression of at least 2 of the following CYPs-1 A1, -1A2, -1B1, -2A6, -2B6, -2C8, -2C9, -2C19, -2D6, -2E1, -3A4, -3A7 and -7A1,
  xi) at least 5% of the cells or, if relevant, cell nuclei exhibit protein and/or gene expression of UGT1A6 and/or UGT2B7.

In one embodiment of the invention, the DE-Hep cells can metabolize drugs via the phase I Cytochrome P450 enzymes. In particular, CYP1A2, CYP2C9 and CYP3A4 can metabolize drugs in the absence of inducers. Substances that can be use in a assay to investigate DE-hep cells ability to metabolize drug substances are e.g. Phenacetin, Diclofenac and Midazolam and the metabolites can be analyzed by LC-MS. It is important to note that the DE-Hep cells constitutively express drug-metabolising enzymes and are thus capable of metabolizing drugs without the influence of inducers.

In a further embodiment, the DE-Hep cells have a composition of CYP-activity similar to the CYP activity composition in human primary hepatocyte cultures. Specifically, the composition of CYP1A2, CYP3A4 and CYP2C9 in the hepatocyte-like cells are comparable to the composition in human primary hepatocyte cultures. The CYP-activity composition between CYP1A2, CYP3A4 and CYP2C9 can differ from 30%, 50%, 75% and 100% compared to the composition in human primary hepatocyte cultures.

In one embodiment of the invention, the DE-Hep cells express functional drug transporters. In particular, expression of OATP-2 is measured by uptake and release of an ICG dye which is an indication of the presence of functional drug transporters within the cells. In addition, protein and/or gene expression of other drug transporters as OATP-8, OATP-A, MRP2, OCT-1, MDR1, MDR3 and NTCP may be found in the DE-Hep cells.

Moreover, a percentage of the DE-Hep cells and DE-Hep progenitors may be positive for Notch-2. The Notch signaling pathways are widely used in embryonic development as well as in adults and maintenance of homeostasis. It is also one of the key pathways constituting the stem cell signaling network. In mammals, four Notch receptors (Notch1-Notch4) and five structurally similar Notch ligands (Delta-like1 [also called Delta1], Delta-like3, Delta-like4, Jagged1, and Jagged2) have so far been identified. Notch ligands are single-pass transmembrane proteins. By binding with ligands expressed on adjacent cells Notch receptors are activated, which leads to proteolytic release and nuclear translocation of the intracellular domain of Notch which in turn regulates differentiation. Notch-2 is widely expressed during embryonic development and has a critical role in many organs. In the liver Notch-2 is involved in the formation and differentiation of intrahepatic ducts (Ader et al., 2005, Kodama at al., 2006). Since liver-like cells are generated by stem cells it is important to understand the role of notch signaling in those cell types.

In addition, DE-Hep cells may express further phase II enzymes besides UGTs and GSTs such as Sulfotransferases.

DE-Hep cells display a morphology typical for hepatocytes, i.e. they have a polygonal cell shape, a large cell diameter (about 25-50 μM), and are often bi-nucleated. DE-Hep are also suborganising in islet-like clusters in culture.

Glucose 6 phosphatase, apolipoprotein E, CYP7A1 (cholesterol 7a hydroxylase), alcohol dehydrogenase 1, cytochrome P450 reductase, HNF4a, alpha-1-antitrypsin, CK18, HNF3b, albumin and Liver-Fatty-Acid-Binding-Protein are all liver-related markers, and as such their expression is indicative of hepatocytes. However, not all of these liver-related markers are necessarily expressed in all cells of a cell population according to the present invention. Even cells that express only one of these markers may behave similar to liver cells and thereby be useful for the above-mentioned purposes depending on what they are supposed to be used for. To study for instance metabolism by the cells CYPs, GSTs and UGTs are desired. To study uptake, OATPs are important and furthermore for excretion studies of e.g. BSEP or MRP-2 may be desired. The more in vivo-like the study to be performed the more of those characteristics are needed. Even better is to potentially have the hepatocyte-like cells together with other liver cell types, such as macrophages and Kupffer cells providing liver environment also with cell-cell interactions. This type of culture system could be in shape of a sandwich into which one or more cell types are embedded. This 3D-like and more in vivo mimicking situation could potentially further make the hepatocyte-like cells show polarity, i.e. showing one cell side towards the blood and one cell side towards the bile. For toxicity studies phase I and II metabolising enzymes are both desired due to their interaction. In addition it is desirable that the cell population is reactive to known drug inducers, whereby e.g. phase I and/or phase II metabolising enzymes are inducible.

In one embodiment of the present invention, at least about 30%, such as, e.g., at least about 40%, at least about 50%, at least about 60%, at least about 70%, at least about 80%, at least about 90%, or at least about 95% of the cells in the cell population having at least three of the above-mentioned characteristics i)-xi). In a specific embodiment, at least one, such as e.g. two, four, six or all, of the characteristics pertaining to the drug transporter group (i.e. characteristics i)-viii)) and/or at least one, such as e.g. two, three or four of the characteristics pertaining to the group of drug metabolizing enzymes (i.e. characteristics ix)-xi)).

Characteristic i) relates to the percentage of cells in the cell population comprising DE-Hep cells, which exhibit protein and/or gene expression of the drug transporter BSEP in the cell population according to the invention. BSEP stands for bile salt export pump and is an ATP-binding cassette (ABC) transporter that catalyses transport of molecules across extra- and intracellular membranes using the energy of ATP hydrolysis and therefore e.g. can export drugs out into the bile (often situated in vivo on what is referred to as the apical side of the hepatocyte). In one embodiment of the present invention, at least 5%, such as, e.g., at least 10%, at least 15%, at least 20%, at least 30%, at least 40%, or at least 50%, at least 60%, at least 70%, at least 80%, at least 90% or at least 95% of the cells in the cell population comprising DE-Hep cells exhibit protein and/or gene expression of BSEP.

Characteristic ii) relates to the percentage of cells in the cell population comprising DE-Hep cells that exhibit protein and/or gene expression of the drug transporter MRP2 in the cell population according to the invention. MRP2 stands for multi-drug resistance protein 2 and is also a member of the ABC transporter family and exports drug metabolites into the bile. In one embodiment of the present invention, at least 5%, such as, e.g., at least 10%, at least 20%, at least 30%, at least 40%, at least 50%, at least 60%, at least 70%, or at least 80%, at least 90% or at least 95% of the cells in the cell population comprising DE-Hep cells exhibit protein and/or gene expression of MRP2.

Characteristic iii) relates to the percentage of cells in the cell population comprising DE-Hep cells that exhibit protein and/or gene expression of the drug transporters OATP-2 and/or OATP-8 in the cell population according to the invention. OATP-2 and OATP-8 stands for organic anion transporters 2 and 8. Both are members of the OATP family, known for instance to take up toxic endogenous metabolites and xenobiotic substances from the blood. The OATPs are in vivo situated on the basolateral side of hepatocytes towards the blood. In one embodiment of the present invention at least 5% such as, e.g., at least 10%, at least 20%, at least 30%, at least 40%, at least 50%, at least 60%, at least 70%, or at least 80%, at least 90% or at least 95% of the cells in the cell population comprising DE-Hep cells exhibit protein and/or gene expression of OATP-2 and/or OATP-8.

Characteristic iv) relates to the percentage of cells in the cell population comprising DE-Hep cells that exhibit protein and/or gene expression of the drug transporter OATP-A in the cell population according to the invention. OATP-A stands for organic anion transporter A and is a member of the OATP family, known for instance to take up toxic endogenous metabolites and xenobiotic substances from the blood. The OATPs are in vivo situated on the basolateral side of hepatocytes towards the blood. In one embodiment of the present invention at least 5% such as, e.g., at least 10%, at least 20%, at least 30%, at least 40%, at least 50%, at least 60%, at least 70%, or at least 80% at least 90% or at least 95% of the cells in the cell population comprising DE-Hep cells exhibit protein and/or gene expression of OATP-A.

Characteristic v) relates to the percentage of cells in the cell population comprising DE-Hep cells that exhibit protein and/or gene expression of the drug transporter NTCP in the cell population according to the invention. NTCP stands for sodium taurocholate co-transporting polypeptide and is a transporter taking up of bile acids from the portal circulation into hepatocytes, This uptake of bile acids is an important component of the entero-hepatic recirculation of bile acids and thus critical for adequate bile flow and normal liver function. NTCP is in vivo situated on the basolateral side of hepatocytes towards the blood. In one embodiment of the present invention at least 5% such as, e.g., at least 10%, at least 20%, at least 30%, at least 40%, at least 50%, at least 60%, at least 70%, or at least 80% at least 90% or at least 95% of the cells in the cell population comprising DE-Hep cells exhibit protein and/or gene expression of NTCP.

Characteristic vi) relates to the percentage of cells in the cell population comprising DE-Hep cells that exhibit protein and/or gene expression of the drug transporter MDR1 in the cell population according to the invention. MDR1 stands for multi-drug resistance transporter 1 and is a member of the ATP-binding cassette (ABC) family of transporters. MDR 1 is important in regulating the traffic of drugs, peptides and xenobiotics into the body and in protecting the body against xenobiotic insults and drug toxicity. MDR 1 is in vivo situated on the apical side of hepatocytes towards the bile canaliculus. In one embodiment of the present invention at least 5% such as, e.g., at least 10%, at least 20%, at least 30%, at least 40%, at least 50%, at least 60%, at least 70%, or at least 80% at least 90% or at least 95% of the cells in the cell population comprising DE-Hep cells exhibit protein and/or gene expression of MDR1.

Characteristic vii) relates to the percentage of cells in the cell population comprising DE-Hep cells that exhibit protein and/or gene expression of the drug transporter MDR3 in the cell population according to the invention. MDR3 stands for multi-drug resistance transporter 3 and is a member of the ATP-binding cassette (ABC) family of transporters. MDR 3 is essential for phospholipid secretion into bile. MDR 3 is in vivo situated on the apical side of hepatocytes towards the bile canaliculus. In one embodiment of the present invention at least 5% such as, e.g., at least 10%, at least 20%, at least 30%, at least 40%, at least 50%, at least 60%, at least 70%, or at least 80%, at least 90% or at least 95% of the cells in the cell population comprising DE-Hep cells exhibit protein and/or gene expression of MDR3.

Characteristic viii) relates to the percentage of cells in the cell population comprising DE-Hep cells that exhibit protein and/or gene expression of the drug transporter OCT-1 in the cell population according to the invention. OCT-1 stands for organic cation transporter 1. OCT-1 is a major hepatic transporter that mediates the uptake of many organic cations from the blood into the liver where the compounds may be metabolized or secreted into the bile. OCT-1 is in vivo situated on the basolateral side of hepatocytes towards the blood. In one embodiment of the present invention at least 5% such as, e.g., at least 10%, at least 20%, at least 30%, at least 40%, at least 50%, at least 60%, at least 70%, or at least 80%, at least 90% or at least 95% of the cells in the cell population comprising DE-Hep cells exhibit protein and/or gene expression of OCT-1.

Characteristic ix) relates to the percentage of cells in the cell population comprising DE-Hep cells that exhibit protein and/or gene expression of the drug metabolising enzymes GST A1-1 and/or GST M1-1 in the cell population according to the invention. Glutathione transferases (GSTs) catalyse the conjugation of xenobiotics with glutathione and are a vital part of the phase II detoxifying system. There are furthermore among 17 different human cytosolic GST subunits divided into seven classes designated e.g. A, M, P, and S. GST A1-1 is the most abundant subunit in the adult human liver in vivo. GST M1-1 is also expressed in the adult human liver, while GST P1-1 is expressed to a higher degree in fetal liver. In one embodiment of the present invention, at least 20%, such as, e.g., at least 30%, at least 40%, at least 50%, at least 60%, at least 70%, or at least 80%, at least 90% or at least 95% of the cells in the cell population comprising hepatocyte-like cells exhibit protein and/or gene expression of GST A1-1 and/or GST M1-1. Further, the expression of GST A1-1- and/or GST M1-1 may also under certain circumstances be induced by an inducer, thus the present invention also relates a cell population wherein at least 20%, such as e.g. 30%, 40%, 50% or more, of the cells obtained expresses GST A1-1 and/or GST M1-1 proteins upon addition of an inducer.

Furthermore, the cell population may be shown to exhibit GST enzymatic activity, which may be at least 0.01 μmol/min/mg, such as, e.g., at least 0.03 μmol/min/mg, at least 0.05 μmol/min/mg, at least 1.0 μmol/min/mg, at least 0.07 μmol/min/mg, at least 0.09 μmol/min/mg, at least 0.11 μmol/min/mg, at least 0.13 μmol/min/mg or at least 0.15 μmol/min/mg of protein in a lysate of the cell population. In another embodiment, the invention relates to a cell population wherein the GST enzymatic activity is at least 0.4 μmol/min/mg, such as, e.g., at least 0.6 μmol/min/mg, at least 0.8 μmol/min/mg, at least 1.0 μmol/min/mg, at least 1.2 μmol/min/mg, at least 1.4 μmol/min/mg, or at least 1.6 μmol/min/mg of protein in a lysate of the cell population.

Characteristic x) relates to the percentage of cells in the cell population comprising DE-Hep cells that exhibit protein and/or gene expression of at least two, such as e.g. at least four, at least six, at least eight, at least ten, at least twelve or all, of the drug metabolising enzymes selected from the group consisting of CYP450s-1A1, -1A2, -1B1, -2A6, -2B6, -2C8, -2C9, -2C19, -2D6, -2E1, -3A4, -3A7 and -7A1 in the cell population according to the invention. In the present invention at least 5%, such as e.g. at least 10%, at least 20%, at least 30%, at least 40%, at least 50%, at least 60%, at least 70%, at least 80%, at least 90% or at least 95% of the obtained cells exhibit activity of the above-referred one or more CYP proteins. Further, in a specific embodiment at last 20%, such as at least 30%, at least 40% or more of the cells obtained expresses at least one of the above-mentioned CYP proteins are inducible upon addition of an inducer.

CYP stands for Cytochrome P450 and is a group of enzymes that are located in the endoplasmatic reticulum of the liver. Their role is metabolism and detoxification of endogenous compounds and xenobiotics. High concentrations of these enzymes can be found in the liver and small intestine, but many CYPs are also found in other tissues. CYPs can be altered by a number of mechanisms including inhibition and induction and can vary from person to person. The CYP system is important for understanding drug metabolism, drug interactions and drug-induced hepatotoxicity.

Characteristic xi) relates to the percentage of cells in the cell population comprising DE-Hep cells that exhibit protein and/or gene expression of at least one of the drug metabolising enzymes UGT1A6 and UGT2B7 in the cell population according to the invention. UGT stands for Uridine diphospho glucuronosyltransferase and is a group of phase II liver enzymes catalyzing glucuronidation activities. In one embodiment of the present invention at least 5% such as, e.g., at least 10%, at least 20%, at least 30%, at least 40%, at least 50%, at least 60%, at least 70%, or at least 80%, at least 90% or at least 95% of the cells in the cell population comprising DE-Hep cells exhibit protein and/or gene expression of UGT1A6 and/or UGT2B7. UGT may also be induced by contacting the cell with an inducer, and thus the invention also relates to a composition of cells, as described above, wherein the expression of UGT protein is inducible upon addition of an inducer.

In one embodiment of the present invention, at least 10%, such as, e.g., at least 20%, at least 30%, at least 40%, at least 50%, at least 60%, at least 70%, or at least 80% at least 90% or at least 95% of the cells in the cell population comprising DE-Hep cells exhibit protein and/or gene expression of at least two such as e.g. at least four, at least six, at least eight, at least ten, at least twelve or all of the following CYP450s-1A1, -1A2, -1B1, -2A6, -2B6, -2C8, -2C9, -2C19, -2D6, -2E1, -3A4, -3A7 and -7A1.

In a specific embodiment at least 20% of the cells in a cell population obtained has at least one of said drug transporter characteristics i-viii), and at least one of said drug metabolism characteristics ix-xi) or at least 20% of the cells of a cell population obtained has at least four, such as, e.g. at least five, at least six, at least seven, at least eight, or at least nine or all of said characteristics.

In specific embodiments of the present invention, the cell composition comprises cells co-expressing CK18 and one or more CYP drug metabolizing enzymes mentioned above, a combination of CYP2C8, CYP2C9 and CYP2Cl$_9$, or a combination of CYP3A4 and CYP3A7, and/or CYP7A1. In a specific embodiment at least about 5%, such as e.g. 10%, 15%, 20% or more of the cells obtained co-express CK18 and CYP3A4 and/or CYP3A7.

As mentioned in the above, the present invention provides improved DE-Hep cells and DE-Hep progenitor cells derived from hBS cells. The improved DE-Hep cells express drug transporters and/or metabolizing enzymes, ensuring similar drug uptake, secretion and metabolism as liver cells in vivo using the same drug transporters and metabolizing enzymes. Thus, expression of all of these features are desirable features for cells to be used in drug discovery and toxicity testing, as their reaction towards drugs and chemicals are expected to resemble the liver cells in vivo.

Accordingly, the DE-Hep cells and DE-Hep progenitor cells disclosed in the present invention are advantageously used for a multitude of investigative purposes, such as, e.g., in a drug discovery process, in in vitro models for studying drug transporters, in in vitro models for studying drug metabolizing enzymes, in in vitro models for studying hepatogenesis, such as, e.g., early hepatogenesis, in in vitro models for studying human hepato-regenerative disorders, for in vitro hepatotoxicity testing.

Other Aspects

Due to the expression of drug transporters and drug metabolizing enzymes, both the DE-Hep cells and DE-Hep progenitor cells of the present invention are well suited for use in a medicinal product. Accordingly, a cell population described in this invention can be used for the manufacture of medicinal products for the prevention and/or treatment of pathologies and/or diseases caused by tissue degeneration, such as, e.g., the degeneration of liver tissue, liver disorders, such as, e.g., liver disorders selected from the group consisting of autoimmune disorders including primary biliary cirrhosis; metabolic disorders including dyslipidemia; liver disorders caused by e.g. alcohol abuse; diseases caused by viruses such as, e.g., hepatitis B, hepatitis C, and hepatitis A; liver necrosis caused by acute toxic reactions to e.g. pharmaceutical drugs; and tumor removal in patients suffering from e.g. hepatocellular carcinoma, and metabolic pathologies and/or diseases.

Furthermore, the DE-Hep cells and DE-Hep progenitor cells according to the present invention are suitably used for screening purposes. For example the cells may be used in a method for screening a compound for hepatocellular toxicity, comprising exposing cells from a cell population according to the present invention to the compound, and determine whether the compound is toxic to the cell. The cells may also be used in a method for screening a compound for its ability to modulate hepatocellular function, comprising exposing cells from a cell population according to the present invention to the compound, determining any phenotypic or metabolic changes in the cells that result from contact with the compound, and correlating the change with an ability to modulate hepatocellular function.

For use in regenerative medicine the hBS cells must have been derived from xeno-free hBS cells (see example 1) and furthermore during differentiation, dissociation and potential subculture never been exposed to non-human animal derived components neither directly nor indirectly. This can be achieved by using exclusively human derived components such as recombinant culture media and additives.

The invention is further illustrated in the following non-limiting examples and figures.

Figure Legends

Method Overview

FIG. 1 a). Schematic overview of the differentiation procedure into DE-Hep cells. The differentiation protocol is divided into 3 main stages. The starting material for the basic protocol consists of undifferentiated hBS cells cultured on mouse embryonic feeders (mEFs). In stage I, starting with the Activin A addition on day 0, the hBS cells are induced into definitive endoderm (DE) via mesendoderm (MesEnd). In stage II the DE is induced via primitive gut into early liver endoderm or liver progenitor cells (DE-Hep progenitors). During stage III the DE-Hep progenitors are maturated into functional hepatocyte-like cells derived from definitive endoderm (DE-Hep cells). b) Schematic overview of the differentiation procedure into functional DE-Hep cells as a specific embodiment of the invention referring to example 2 (named protocol 1). Protocols 2 to 4 are alternative protocols embodied in the present invention referring to example 2. Variations of the starting material and/or variations during the culture procedure into DE-Hep cells are described in examples 1 and 2.

Definitive Endoderm (DE)

Figure 2:
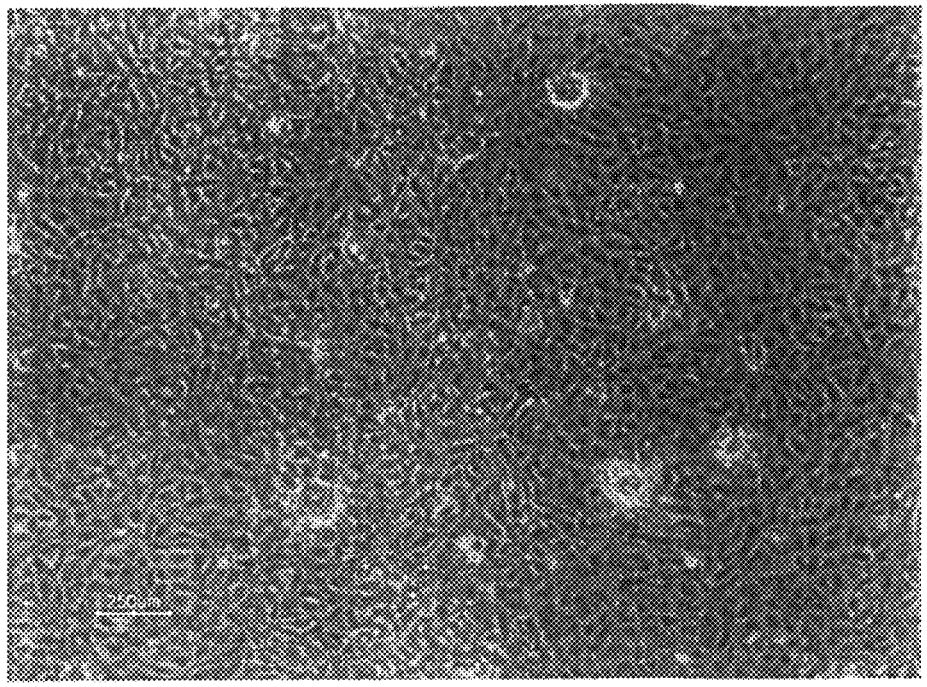

FIG. 2. Morphology of definitive endoderm (DE); Phase-contrast image of Activin A treated hBS cells for derivation of DE at day 5 of culture, stage I.

Figure 3:

FIG. 3. Immunostainings confirming definitive endoderm; Sox17 immuno-fluorescence analysis of a hBS cell culture induced to definitive endoderm by Activin A. After 4 days with Activin A the vast majority of the cells are Sox17 positive and Sox7 negative.

Figure 4:
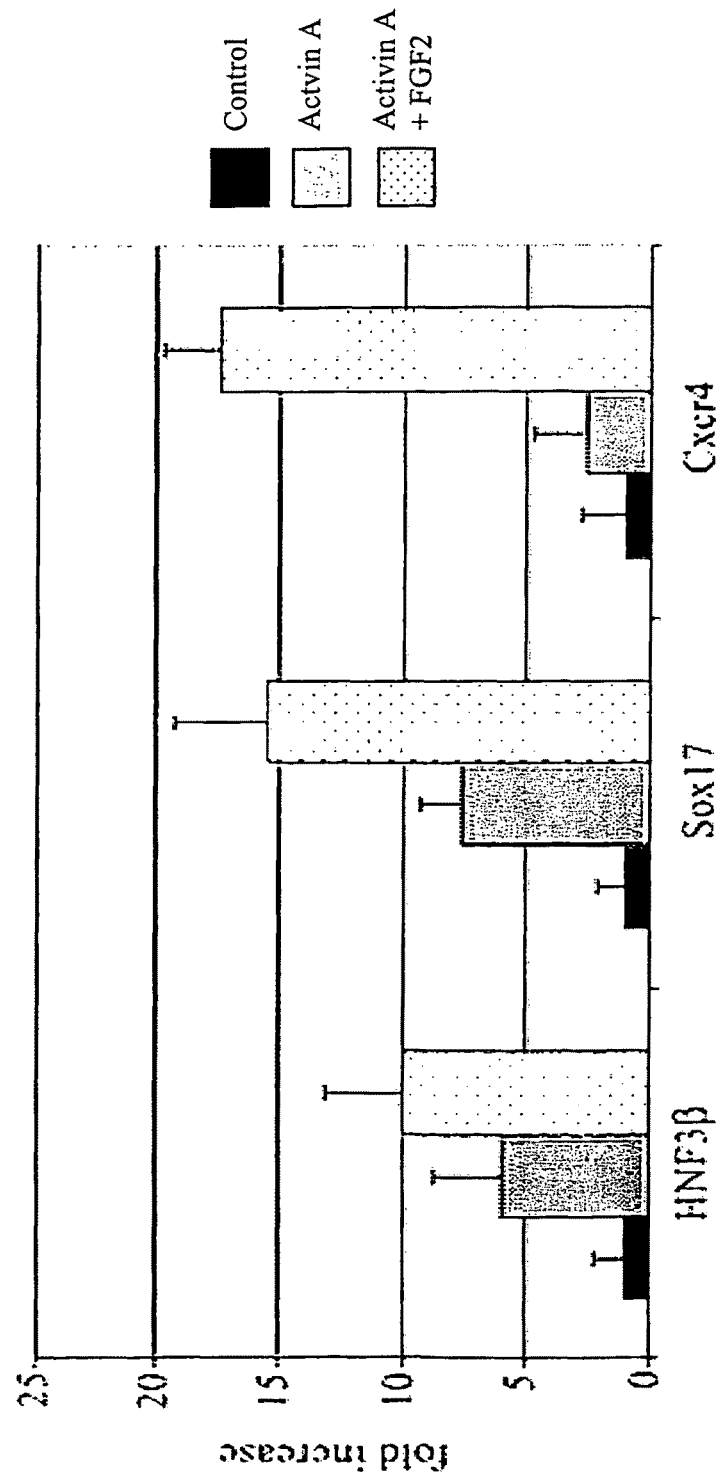

FIG. 4. Diagram showing a representative figure of the relative gene expression levels of HNF3b, Sox17, Cxcr4 analyzed by Q-PCR of DE cultures cultured in the present of growth factors according to stage I (see Example 2), and control cultures (intrinsically differentiated cultures without Activin A) at day 5. Cultures supplemented with; Activin A and FGF2 (grey bars), compared to cultures with Activin A (black bars), and with control cultures derived without supplements (white bars).

Figure 5:
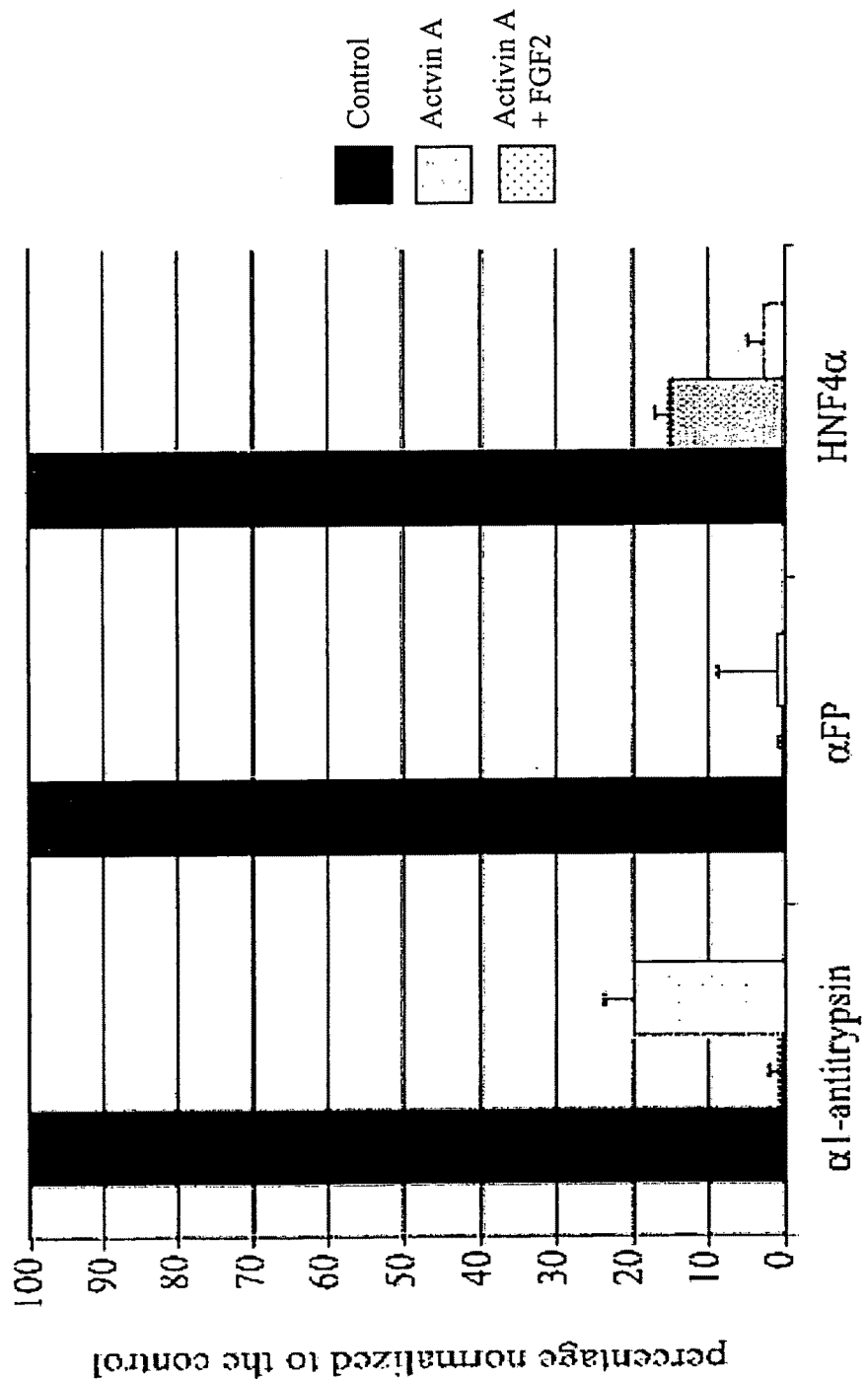

FIG. 5. Diagram showing a representative figure of the relative gene expression levels of HNF4a, alpha-1-antitrypsin and AFP analyzed by Q-PCR of DE cultures cultured according to stage I (see Example 2), and control cultures (intrinsically differentiated cultures without Activin A) at day 5. Cultures supplemented with; Activin A and FGF2 (grey bars), compared to cultures with Activin A (white bars), and with control cultures derived without supplements (black bars).

Figure 6:
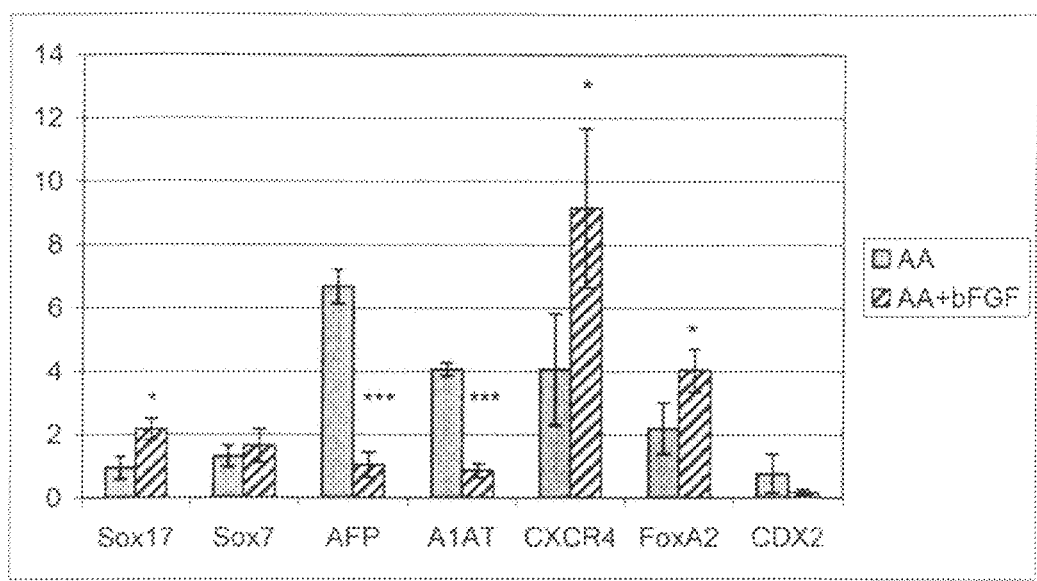

FIG. 6. Representative figure of QPCR analysis of gene expression in A) Activin A comparison to B) Activin A+bFGF treated hESC cultures (SA002 p70 n=7) as described in Example 2, stage I. The relative gene expression levels of SOX17, SOX7, AFP, A1AT, CXCR4, FOXA2 and CDX2 was analyzed by QPCR of DE cultures cultured in the present of Activin and bFGF for 5 days. Cultures supplemented with; Activin A and bFGF/FGF2 (striped bars), compared to cultures with Activin A (grey bars). Comparable results was also generated with SA002 p29 n=5.

Figure 7:
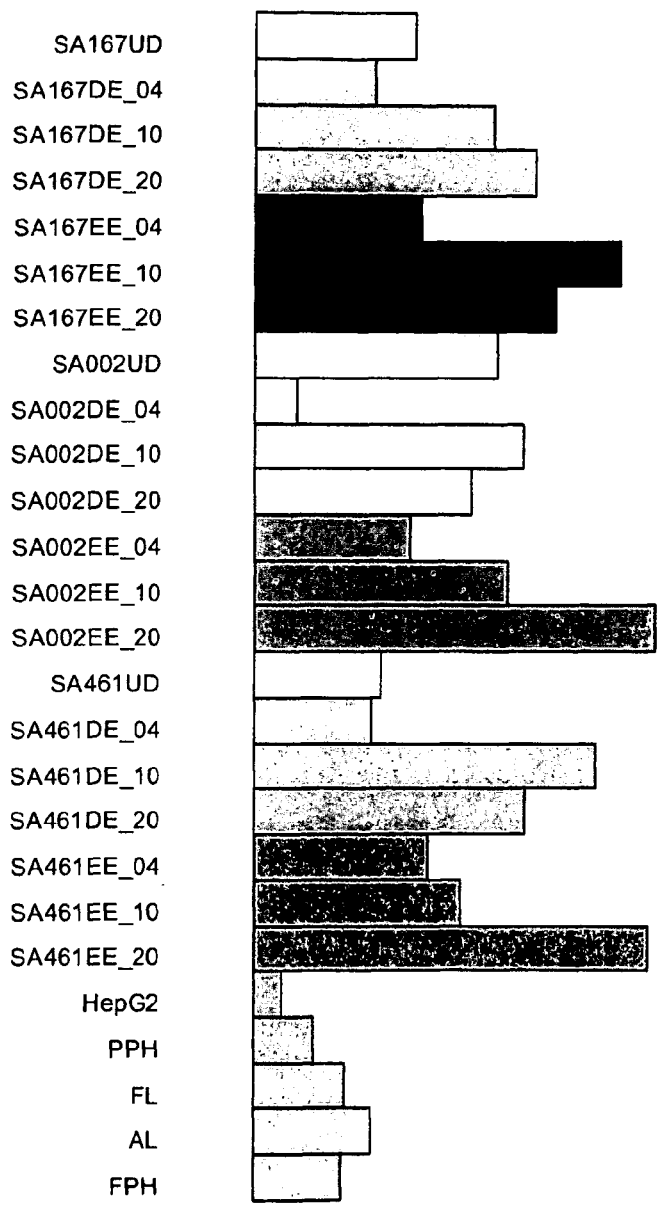
Figure 7A:
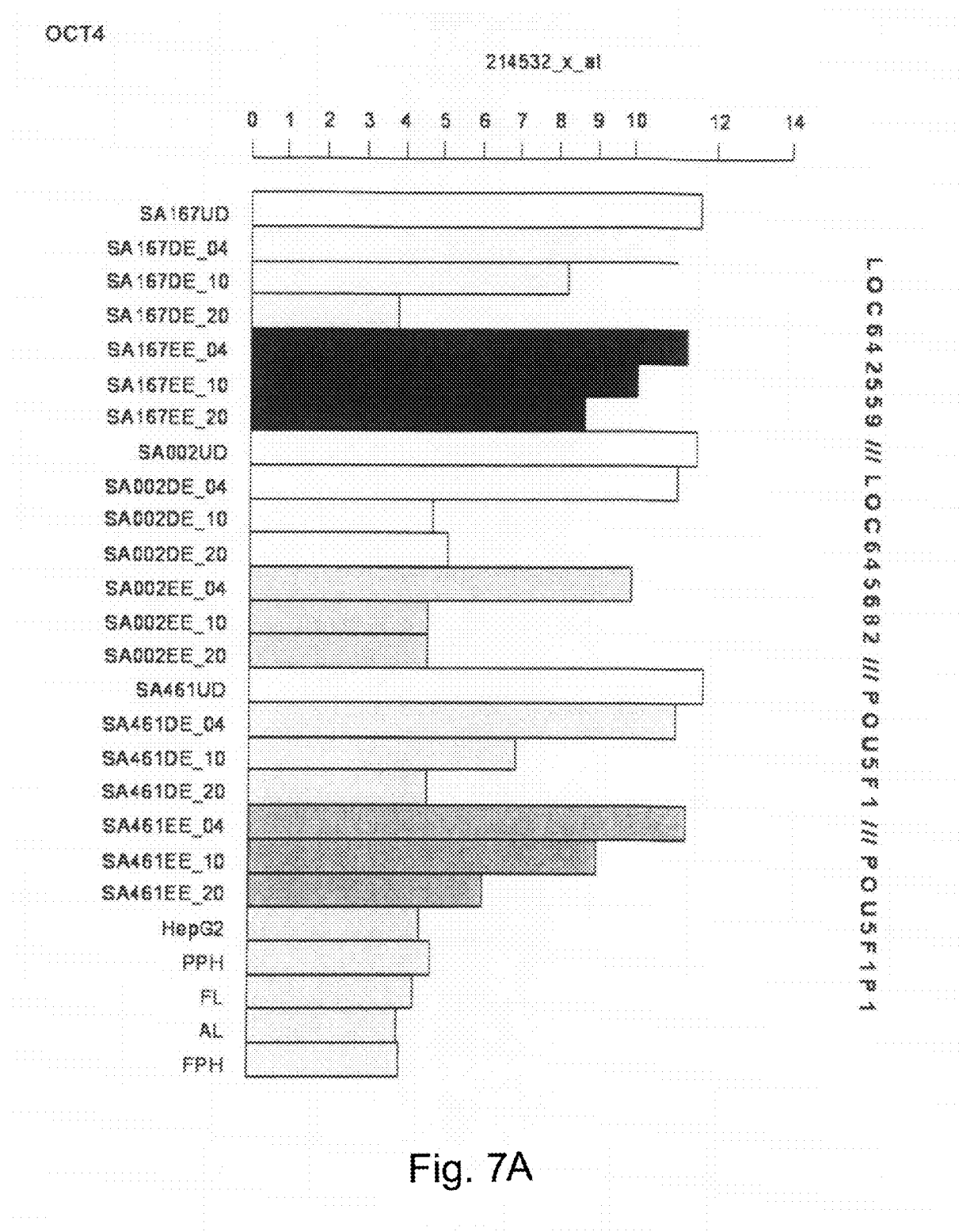
Figure 7B:
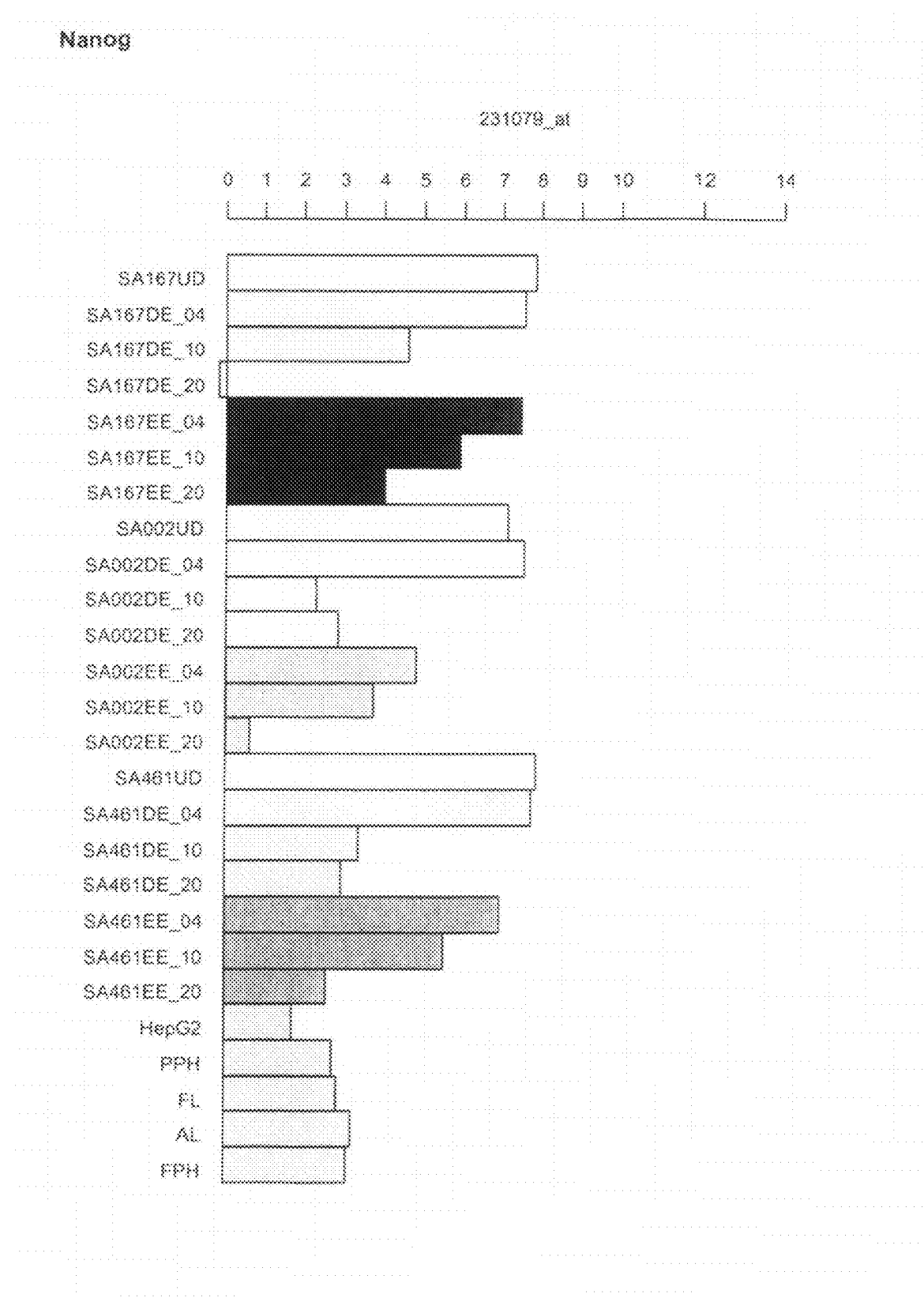
Figure 7C:
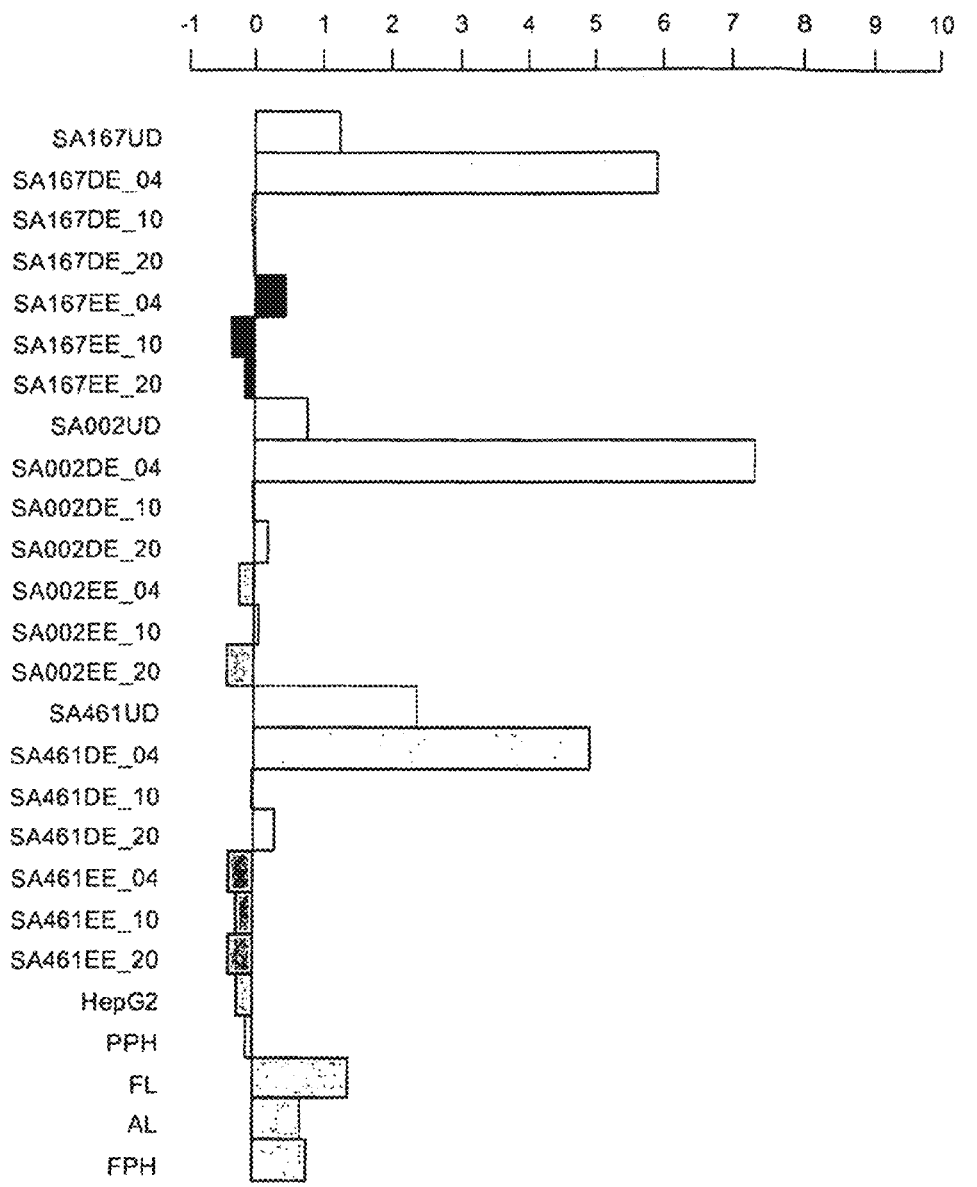
Figure 7D:
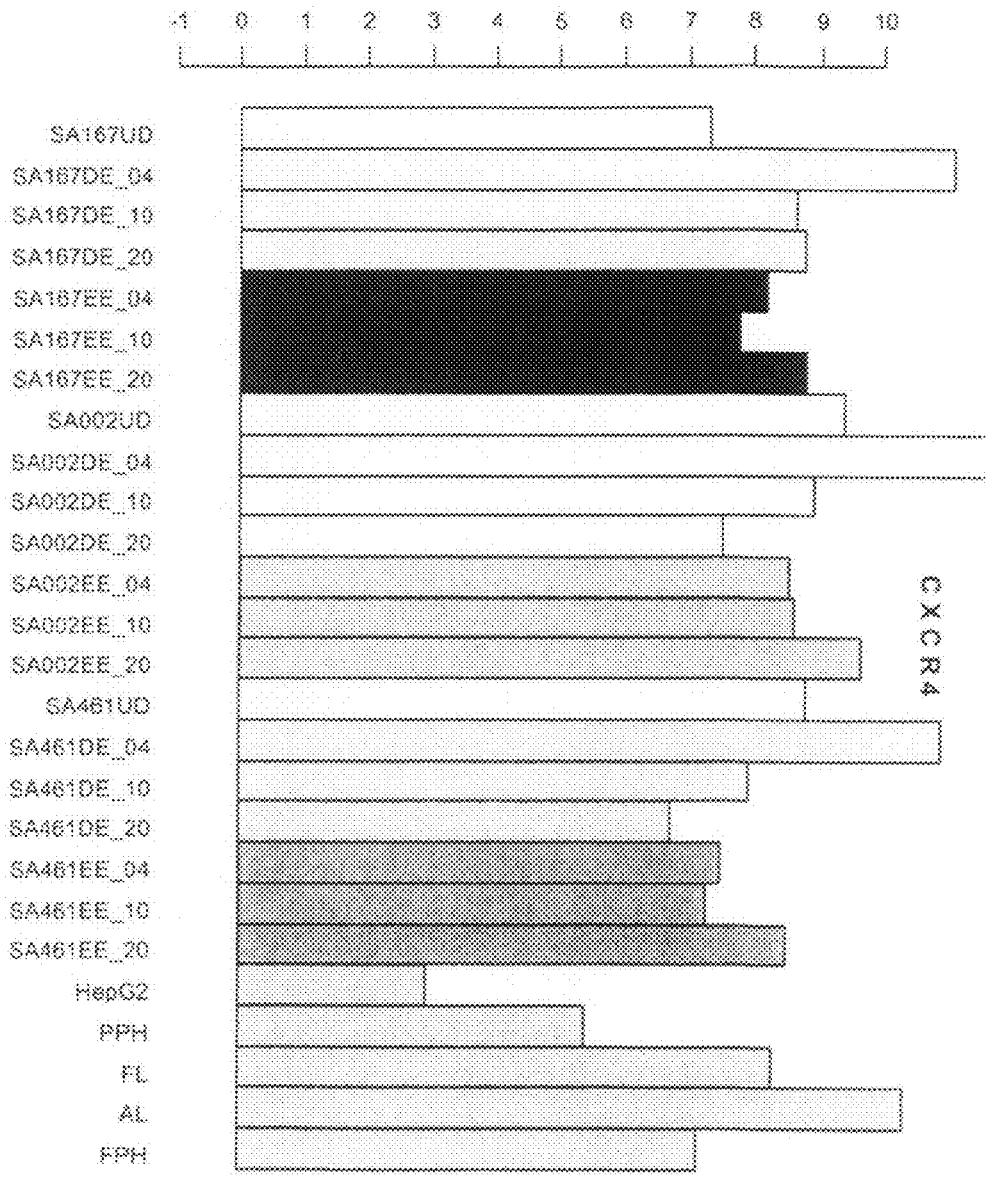
Figure 7E:
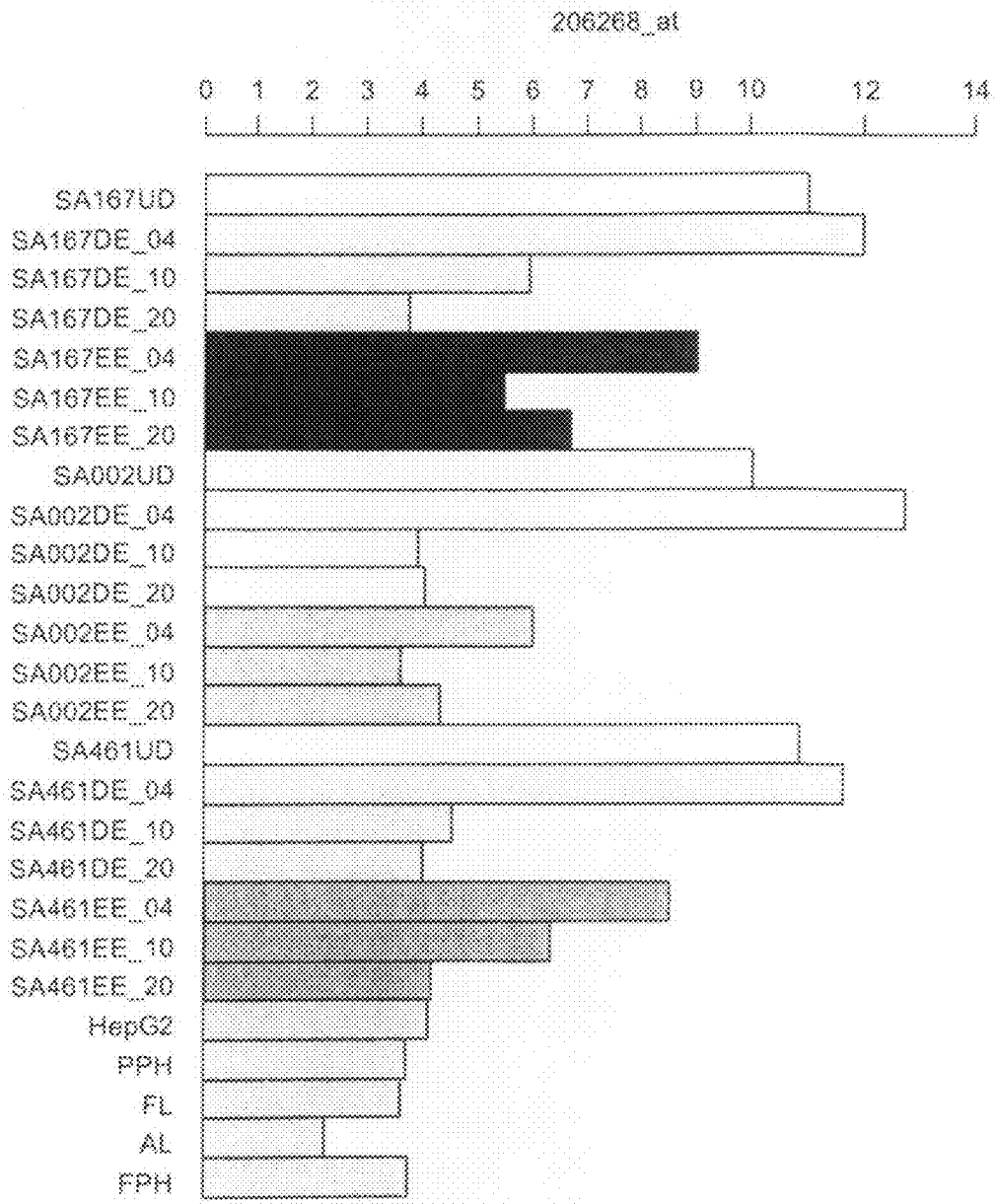
Figure 7F:
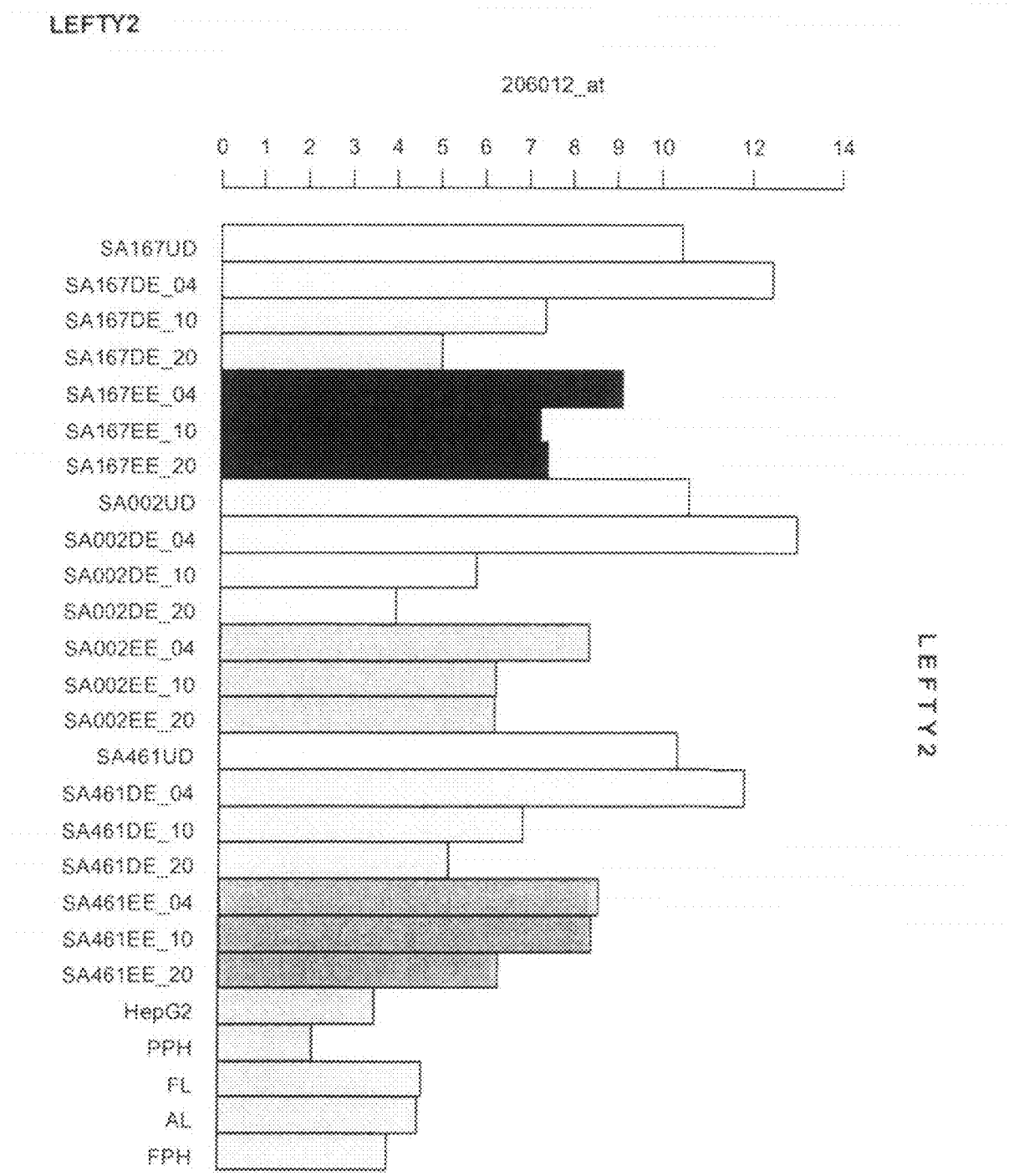
Figure 7G:
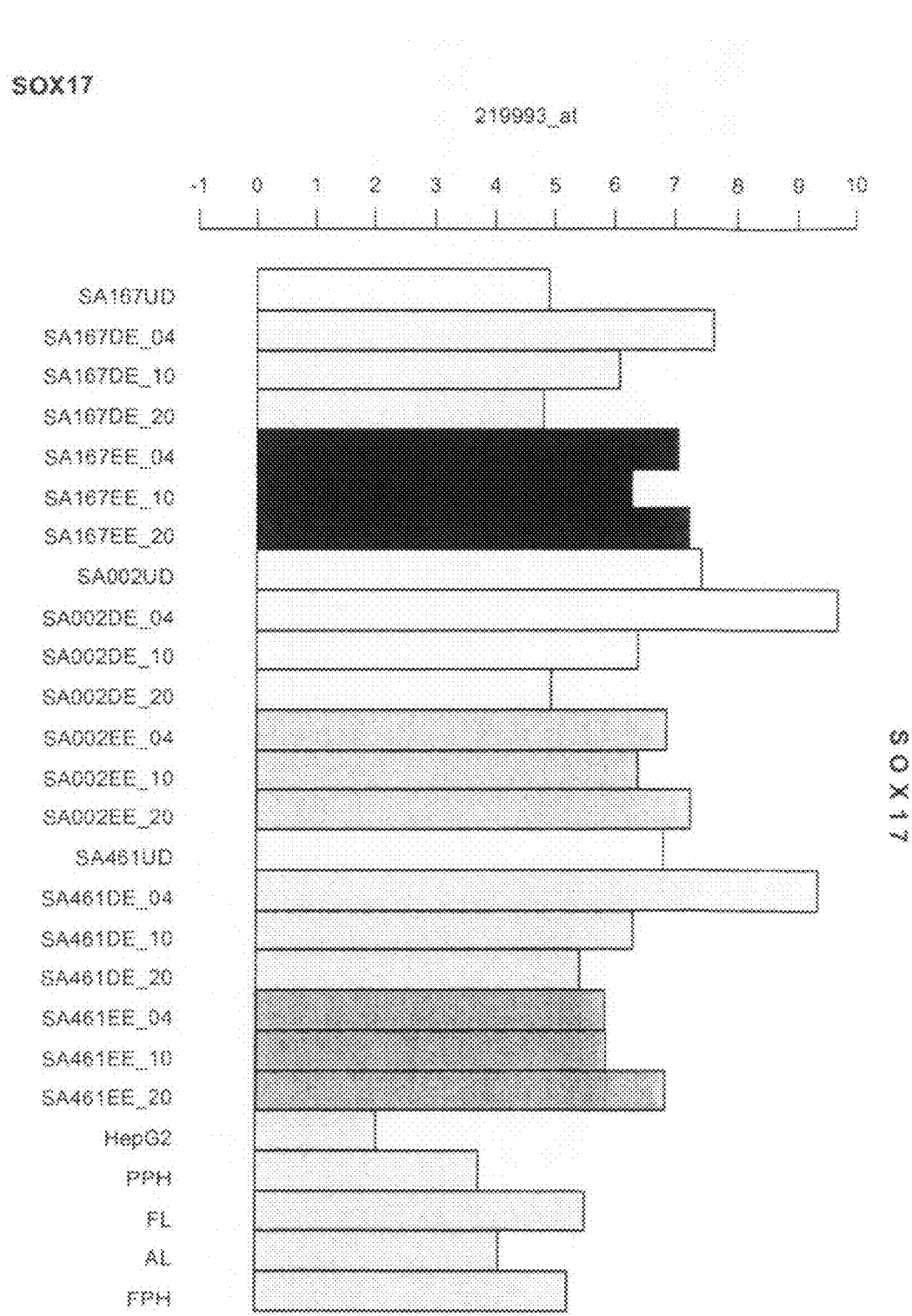
Figure 7H:
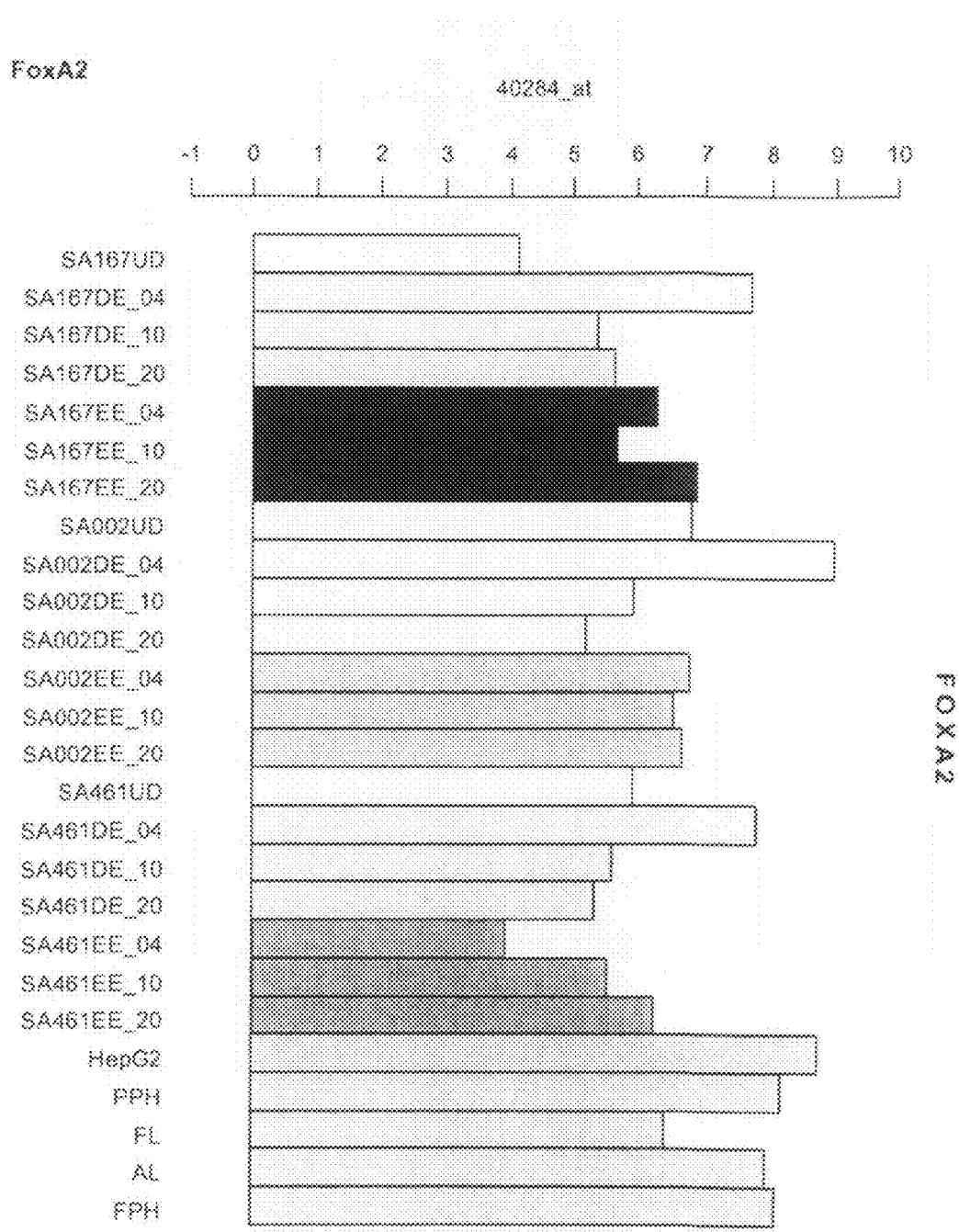
Figure 7I:
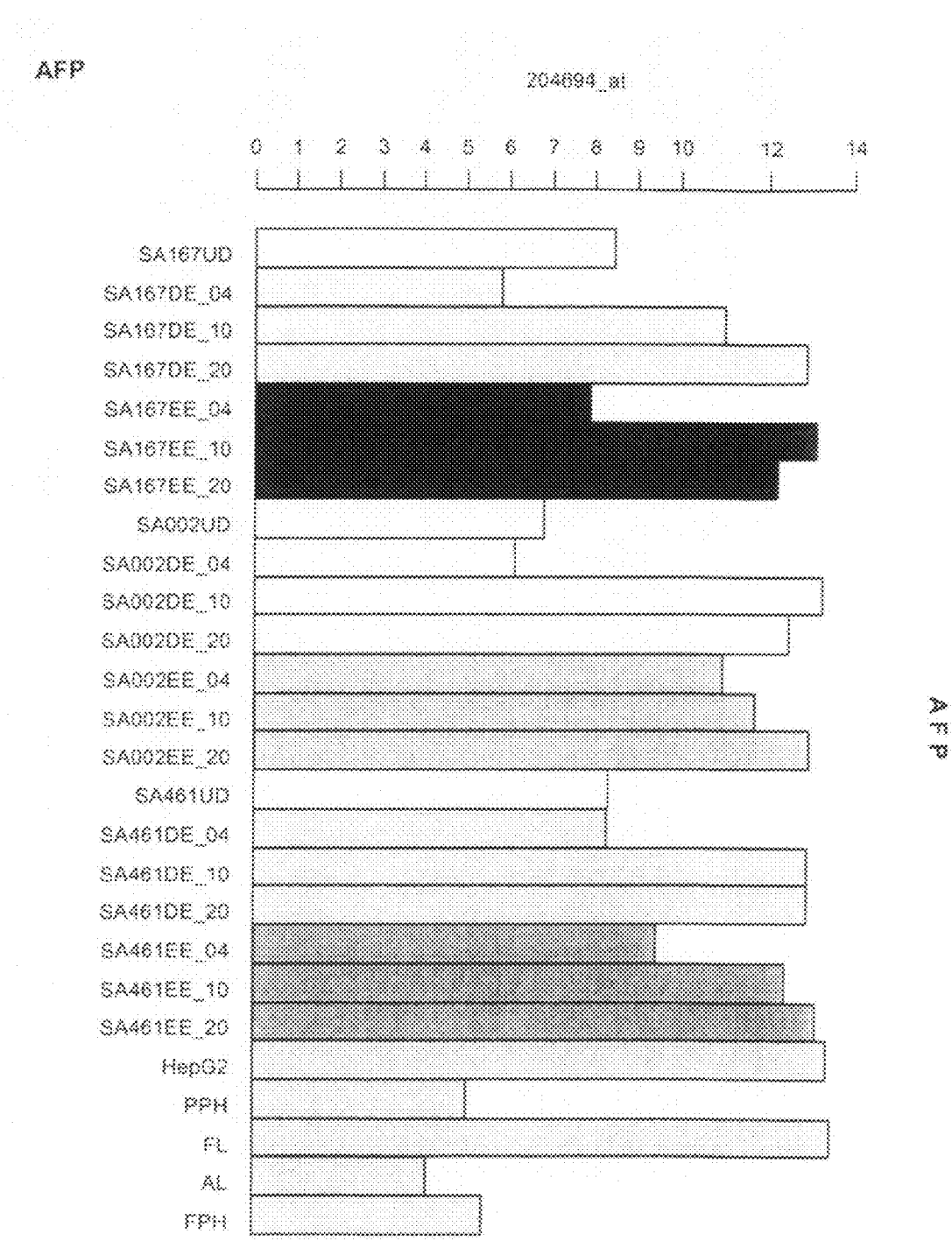
Figure 7J:
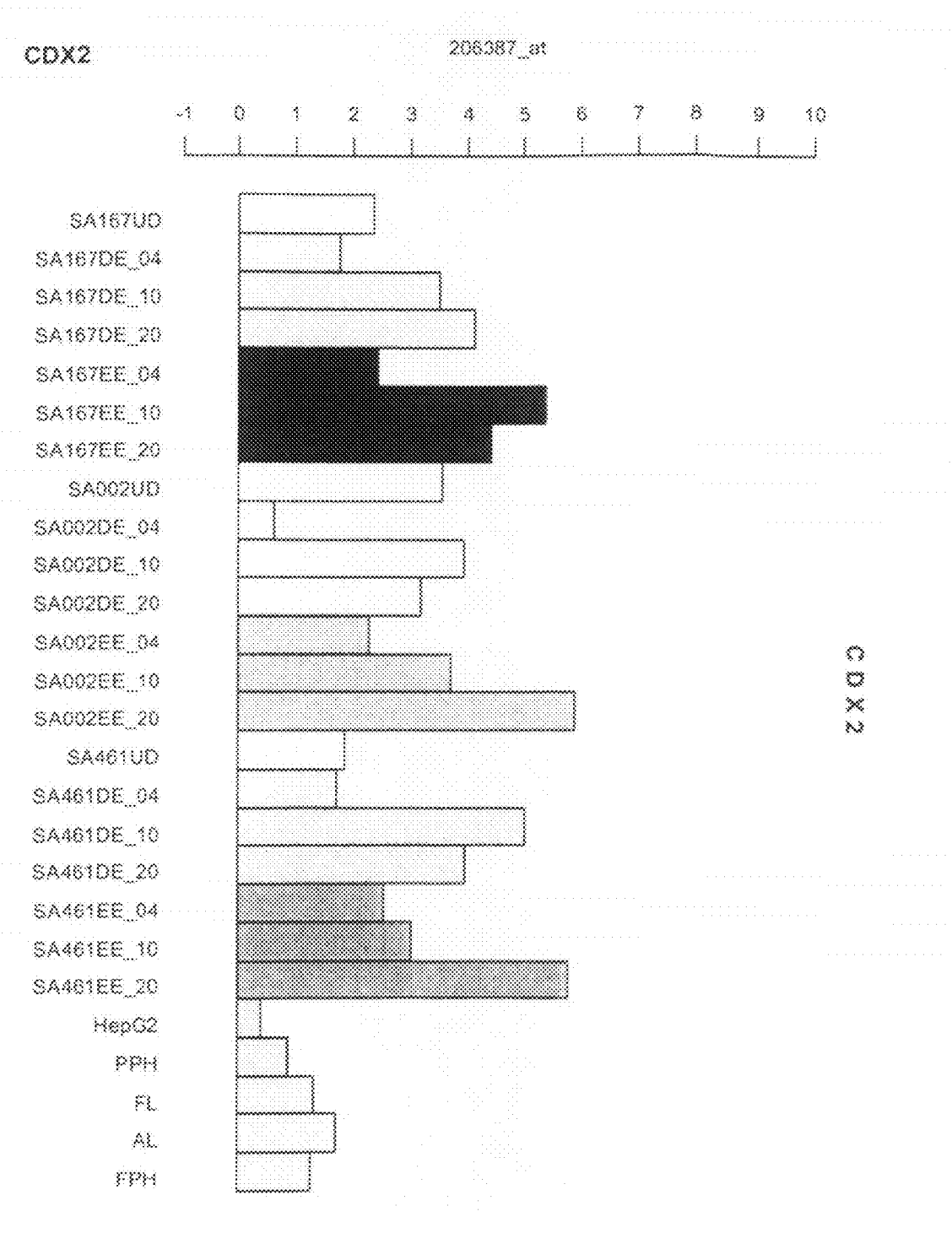

FIG. 7. All the plots are in log 2 scale for visualizing expression values for all samples. Plots of gene expression for OCT4 and Nanog are representative for all the undifferentiated markers used in this experiment. To examine the induction of DE in culture LEFTY1, LEFTY2, GOOSECOID, SOX17, HNF3B, CXCR4 were analysed and were all upregulated in Activin A and bFGF treated cultures compared to intrinsic differentiated cultures (EE). While AFP and CDX2 all were lower expressed in Activin A and bFGF treated cultures compared to intrinsic differentiated cultures. This gives that Activin A and bFGF conditioned media induces DE from hBS cells. Black arrows points at relative bars.

DE-Hep Progenitors

Figure 8:
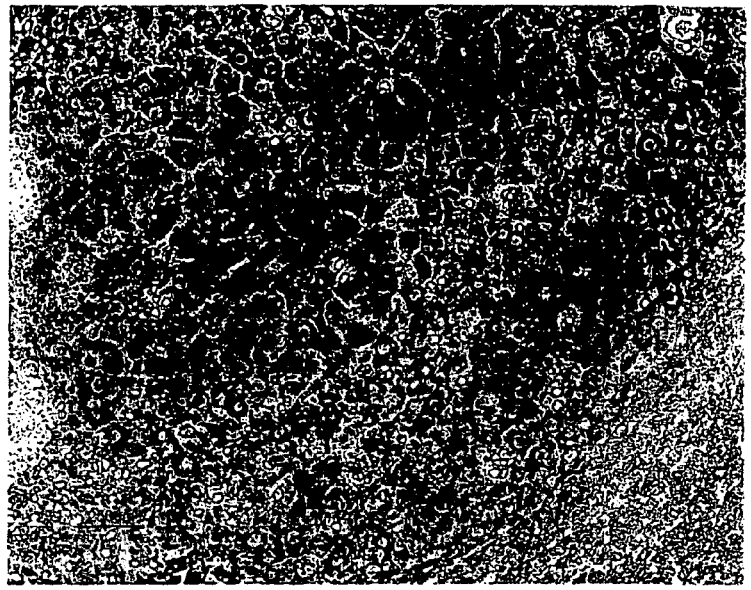

FIG. 8. Morphology of DE-derived hepatic progenitors (DE-Hep progenitors) from stage II. The cultures strongly responded to BMP4 exposure and after 2 days in stage II medium a rather heterogeneous population, among many epithelioid cell types was obtained. After additional 6-9 days in stage II medium, the first polygonal-shaped cells, some of them bi-nucleated, appeared as shown in FIG. 6.

Figure 9:
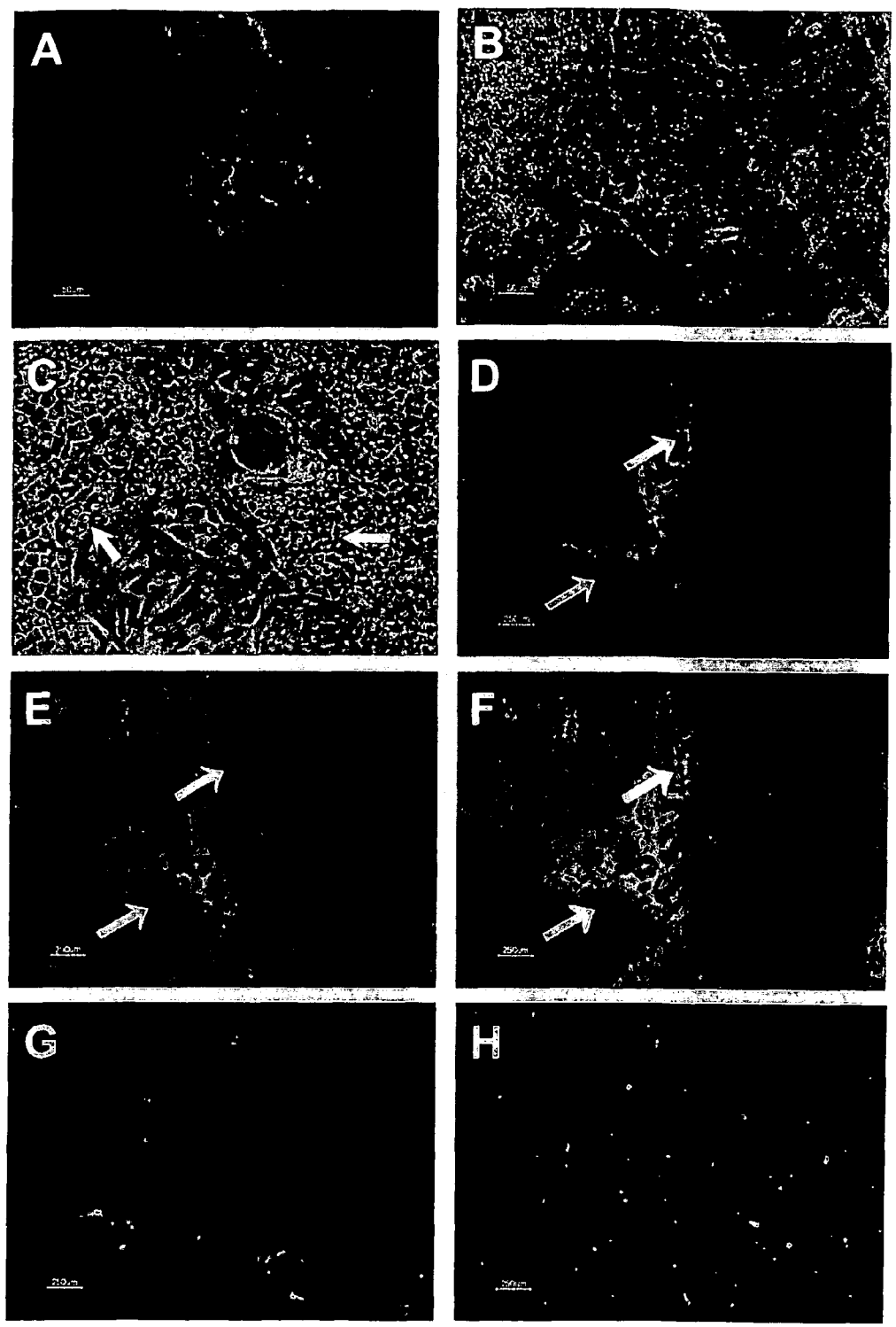

FIG. 9 a-h). EpCAM staining of hBS cell derived DE-Hep progenitors. a) A DE culture at day 8, according to stage II, labelled with an EpCAM antibody, b) a phase-contrast image of the corresponding region. The DE cultures strongly responded to the growth factors applied in phase II and the former homogenous epithelial cells changed morphology into polygonal-shaped cells (compare also 7 c)).

c-h) Morphology and expression of EpCAM and CK19 of DE-Hep progenitors. c) Phase contrast image of a DE culture at day 17 containing polygonal-shaped cells (white arrows point), d) the corresponding region labeled with an EpCAM antibody and in e) with a CK19 antibody, f) overlay of EpCAM and CK19 (white arrows in d, e and f show some of the double positive cells). g) DE-Hep cells at day 14 are positive for CD54 and, h) CK7.

Figure 10:
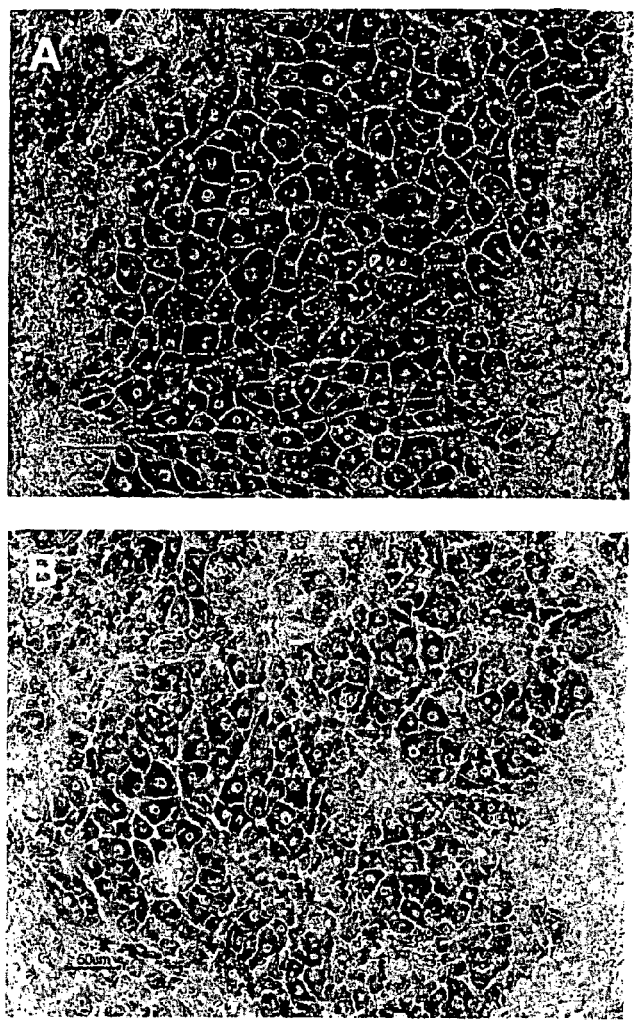

FIG. 10 a-b). Late stage DE-Hep progenitors/early DE-Hep cells in stage II/III derived from hBS cells. a,b) Phase-contrast image of DE-Hep progenitors at day 8 in stage II medium, total 20 days in culture counted from passage day.

Functional DE-Hep Cells

Figure 11:
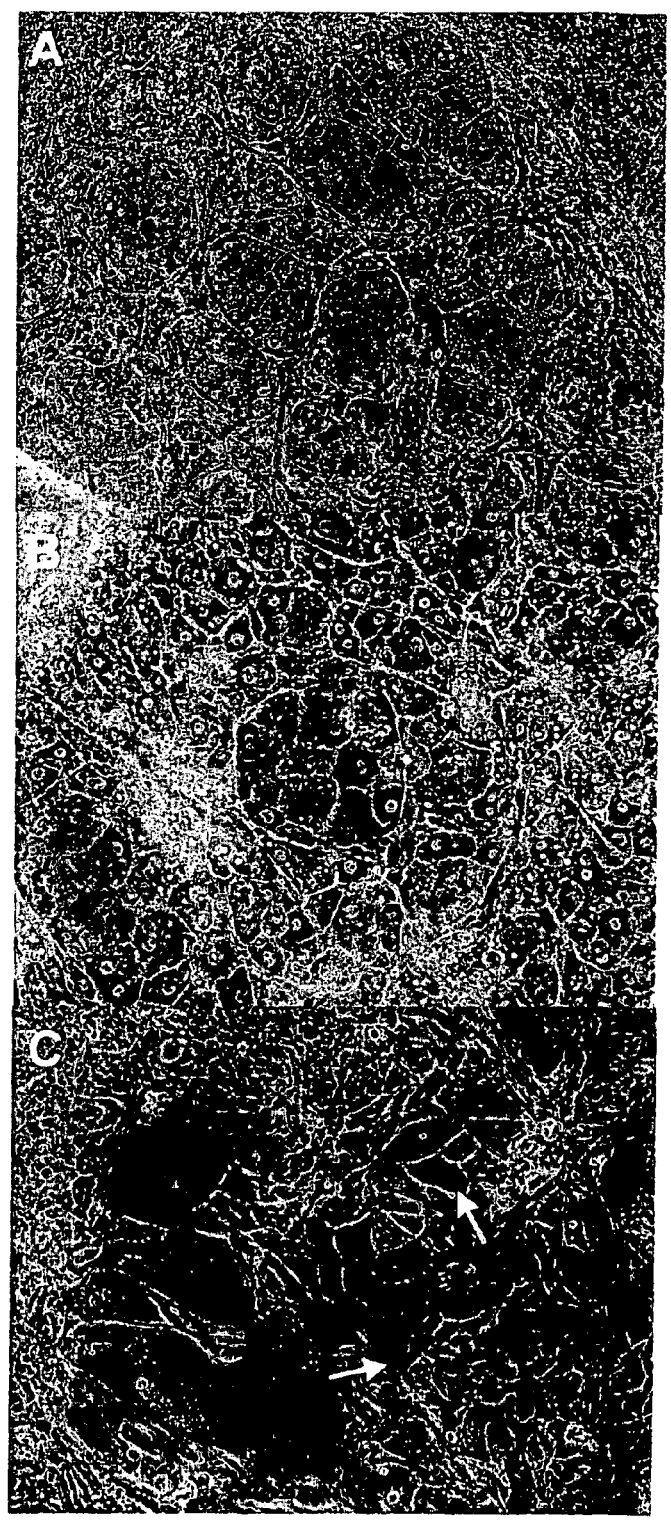

FIG. 11 a-b). DE-Hep cells in stage III derived from hBS cells and, c) from SCED cells. a,b) Phase-contrast image of DE-Hep cells at day 12 in stage II medium, total 23 days in culture counted from passage day. a) shows an overview picture and the corresponding higher magnification in b). Note that the cells are arranged in clusters, are bi-nucleated and exhibit a hepatocyte-like morphology. c) Phase-contrast image of DE-Hep cells at stage III derived from SCED cells, day 33 in culture. Note the white arrows showing bi-nucleated DE-Hep cells with typical hepatocyte-like cell morphology.

Figure 12:
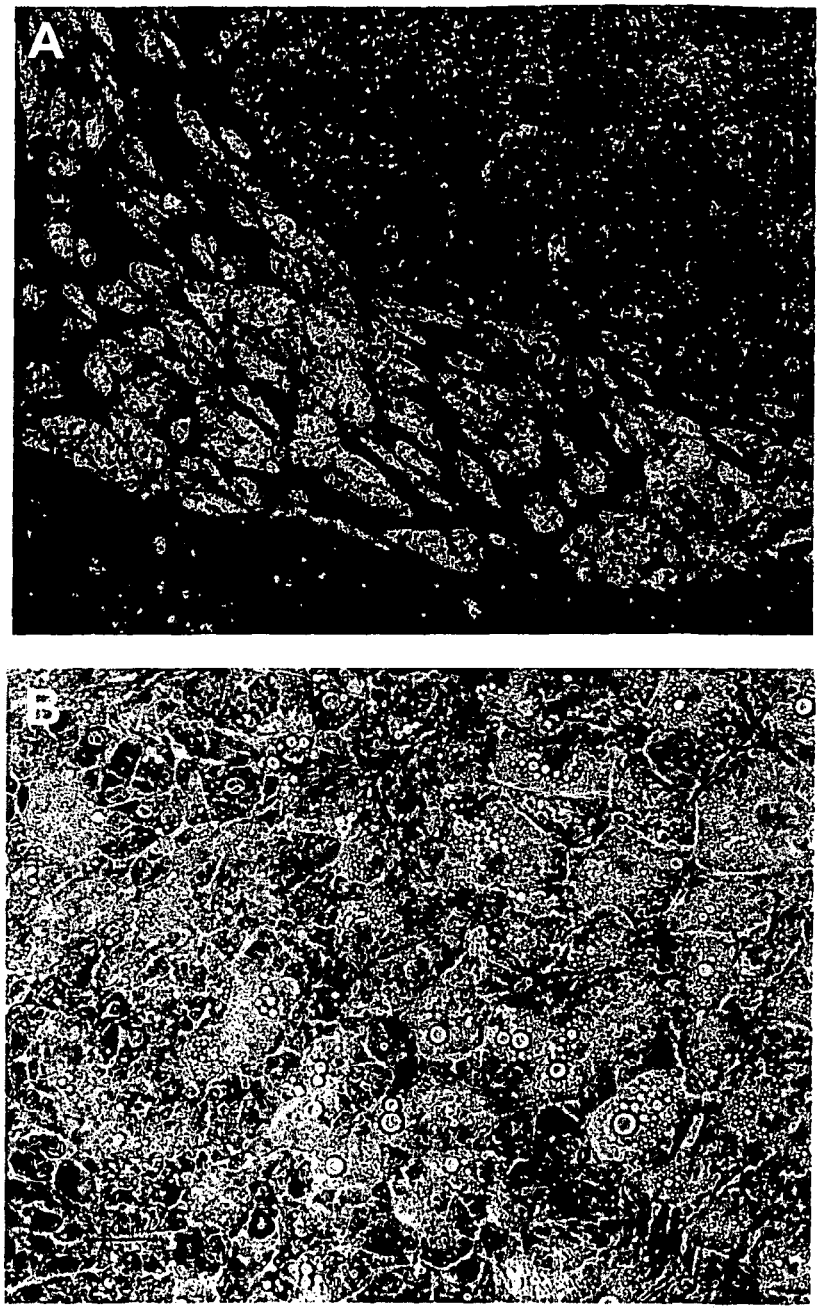

FIG. 12 a-b). Hepatocyte-like cells generated by the intrinsic differentiation of hBS cells on MEFs, e.g. no specific supplements added to the culture medium and sparse Vitro-HES™ medium changes, (compare patent application WO2007/140968A1) are used as controls. a) hepatocyte-like cells are located at the periphery of the hBS cell colony. b) Close-up of hepatocyte-like cells derived under those conditions shows that the cells are highly enriched with triglycerides.

Figure 13:
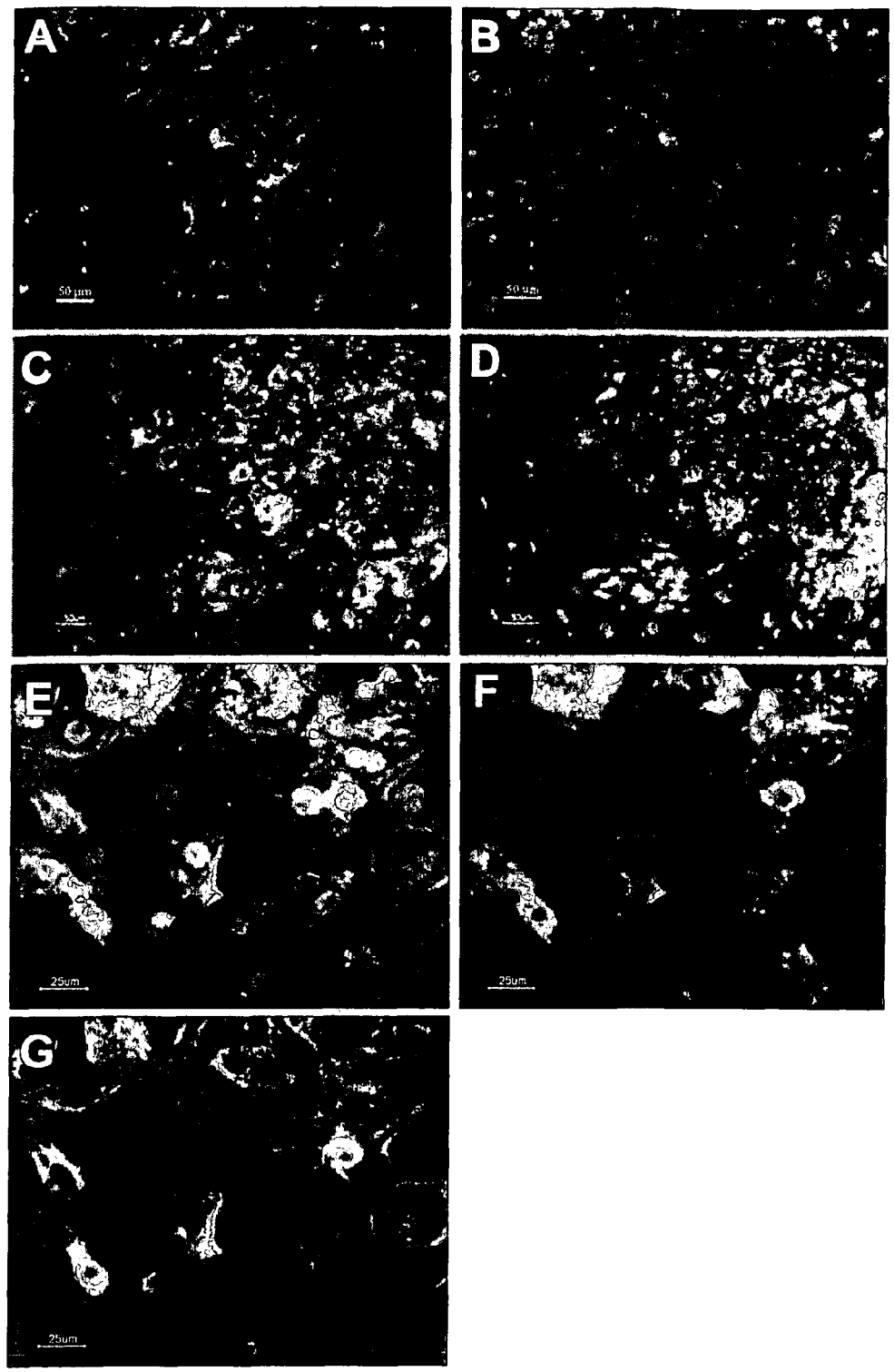

FIG. 13 a-g). CYP expression of DE-Hep cultures during stage III. Immunofluorescent labeling of DE-Hep cells at stage III show strong CYP1A2 immunoreactivity a), whereas hepatocyte-like cells in control cultures (intrinsic differentiation) show lower CYP1A2 immunoreactivity (not shown), b) CYP1A2 and nuclear counterstaining with DAPI. DE-Hep cells also display c) CYP3A4 immunoreactivity, d) overlay of nuclear DAPI and CYP3A4. Higher magnification of corresponding DE-Hep cell cultures at stage III immunofluorescent labeled with e) CYP3A4, CK18 and DAPI merged into one figure, f) CYP3A4, and g) CK18.

Figure 14:
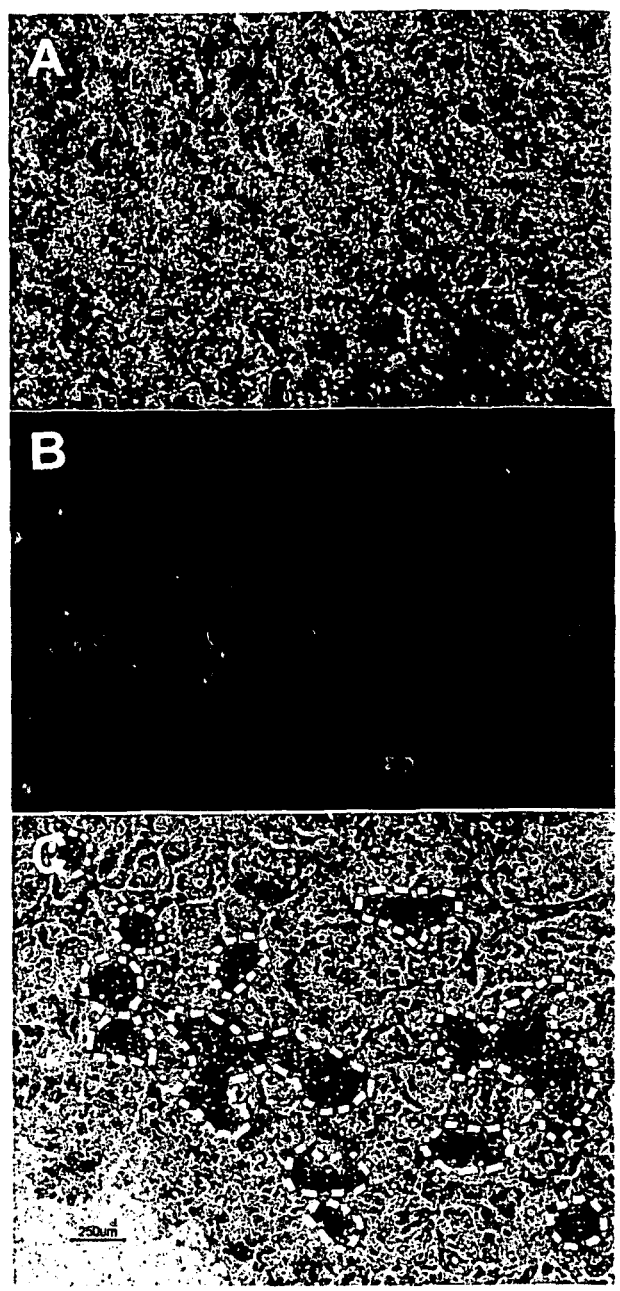

FIG. 14 a-c). Immunofluorescence analysis of the organic anion transporter MRP2 gene in DE-Hep cells showing the functional activity of the cells. MRP2 immunoreactivity is found in DE-Hep cells and shows the typical expression pattern. a) Phase contrast image showing morphology, and b) MRP2 immunoreactivity in DE-Hep cells at stage III, 21 days. Phase-contrast pictures of c) indocyanine green (ICG) uptake (encircled areas) in DE-Hep cells after 1 h incubation. Clearance followed over night.

Figure 15:
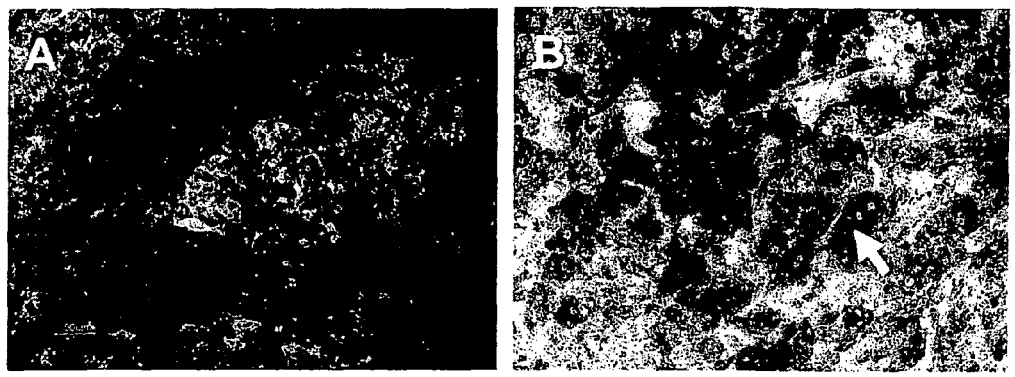

FIG. 15. Glycogen storage in DE-Hep cells showing the functionality of the cells. Phase-contrast pictures of DE-Hep cells at low a) and high magnification b) at stage III day 21 in culture, showing dark areas of glycogen storage. Note that some cells in b) are binucleated and store glycogen (white arrow).

Figure 16:
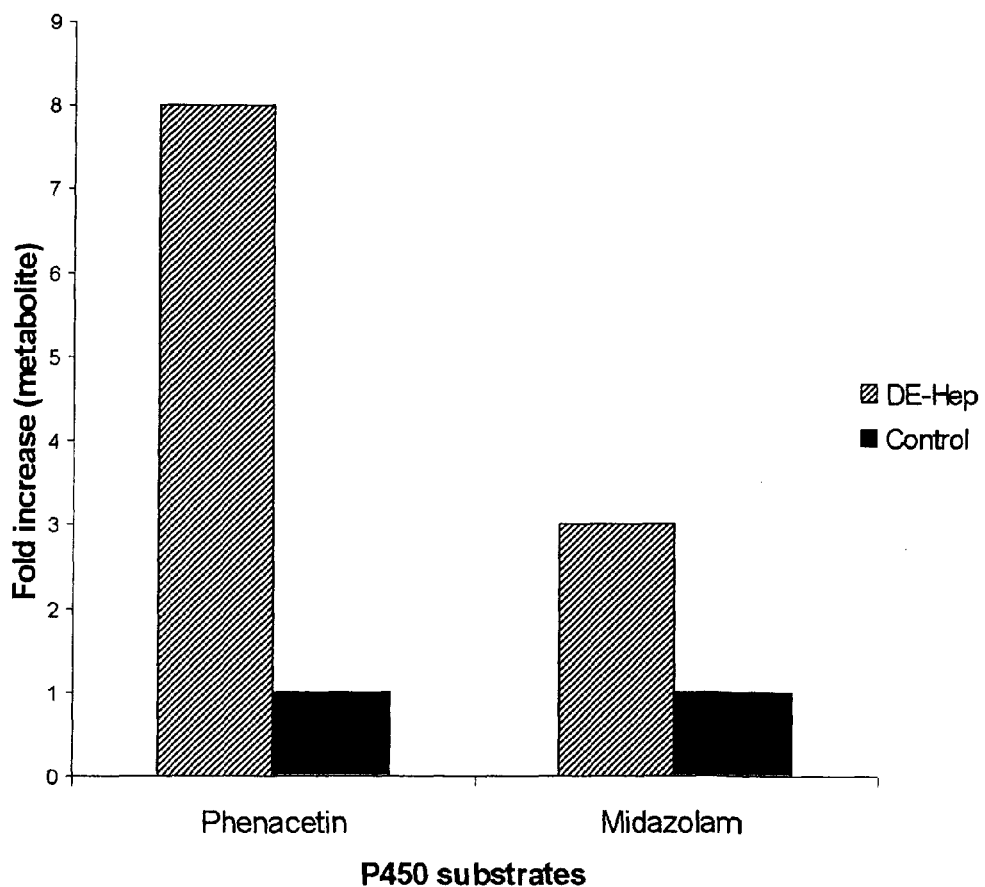

FIG. 16. Functional drug metabolism via CYP1A2, CYP3A4 and CYP2C9 and inducibility of CYP expression in DE-Hep cultures.

DE-Hep cells derived from several hBS cell lines, human primary hepatocytes isolated from different donors and the hepatoma cell line HepG2 were analyzed for their ability to metabolize the CYP1A2 substrate Phenacetin, the CYP3A4 substrate Midazolam and the CYP2C9 substrate Diclofenac.

A) Representative results of CYP activity assays on DE-Hep cultures derived from different hBS cell lines with different DE-protocols. Note that DE-Hep cultures derived from different hBS cell lines differ in metabolic activity for CYP1A2, 3A4 and CYP2C9 resulting in typical CYP activity profiles for different hBS cell lines. B) Also human primary hepatocytes from different donors show a high inter-individual variation of CYP activity profiles similar to DE-Hep cultures derived from different hBS cell lines. The hepatoma cell line HepG2 shows mainly CYP1A2 activity. C,D) Upon treatment with a cocktail of CYP inducers, DE-Hep cultures show a more than 3 fold upregulation of CYP1A2 activity (C), and a 3-4 fold increase in CYP1A2 mRNA and CYP3A4 mRNA levels (D). The results are presented as nM metabolite (B,C), log [nM metabolite] (A) and fold change in RNA expression (D; untreated DE-Hep culture is set as one).

Figure 17:
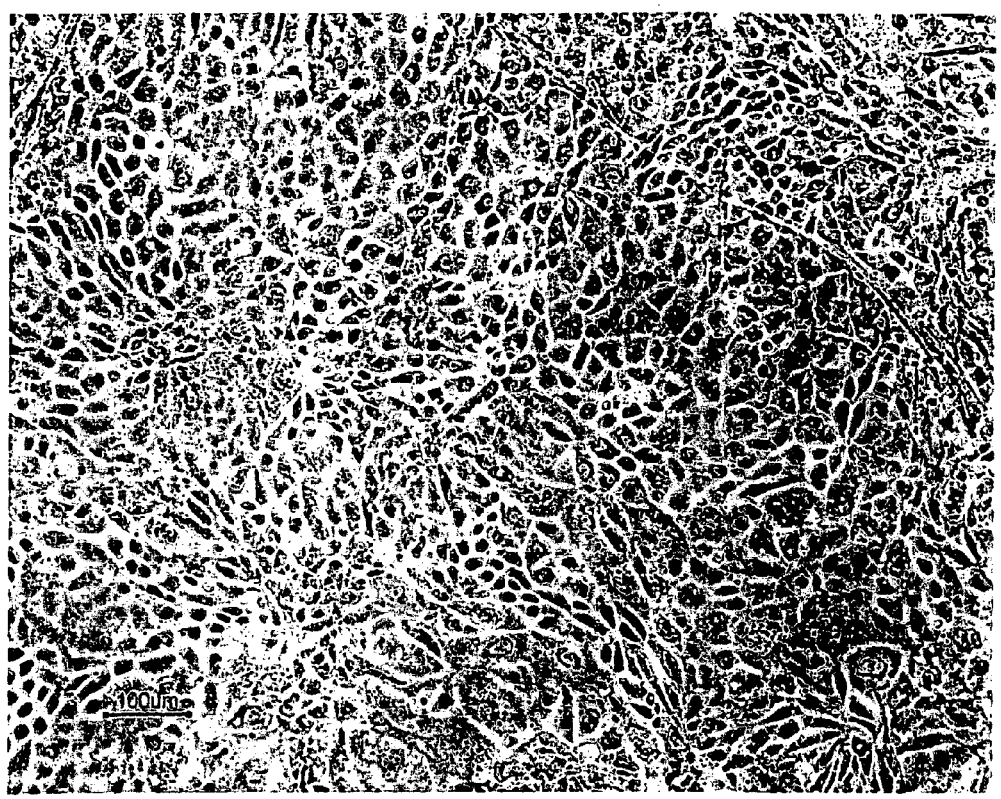

FIG. 17. Morphology of DE-Hep progenitors derived from DE cells which have been transferred from MEF onto a Matrigel coated plate. In the presence of stage II medium (see Example 2) the cells differentiated rapidly towards hepatic progenitor cells and proliferated as well. On day 16 in stage II many cells were EpCAM, CK7, CK19 and CD54 immunopositive (data not shown, compare Table 2 for markers expressed in DE-Hep progenitors).

Figure 18:
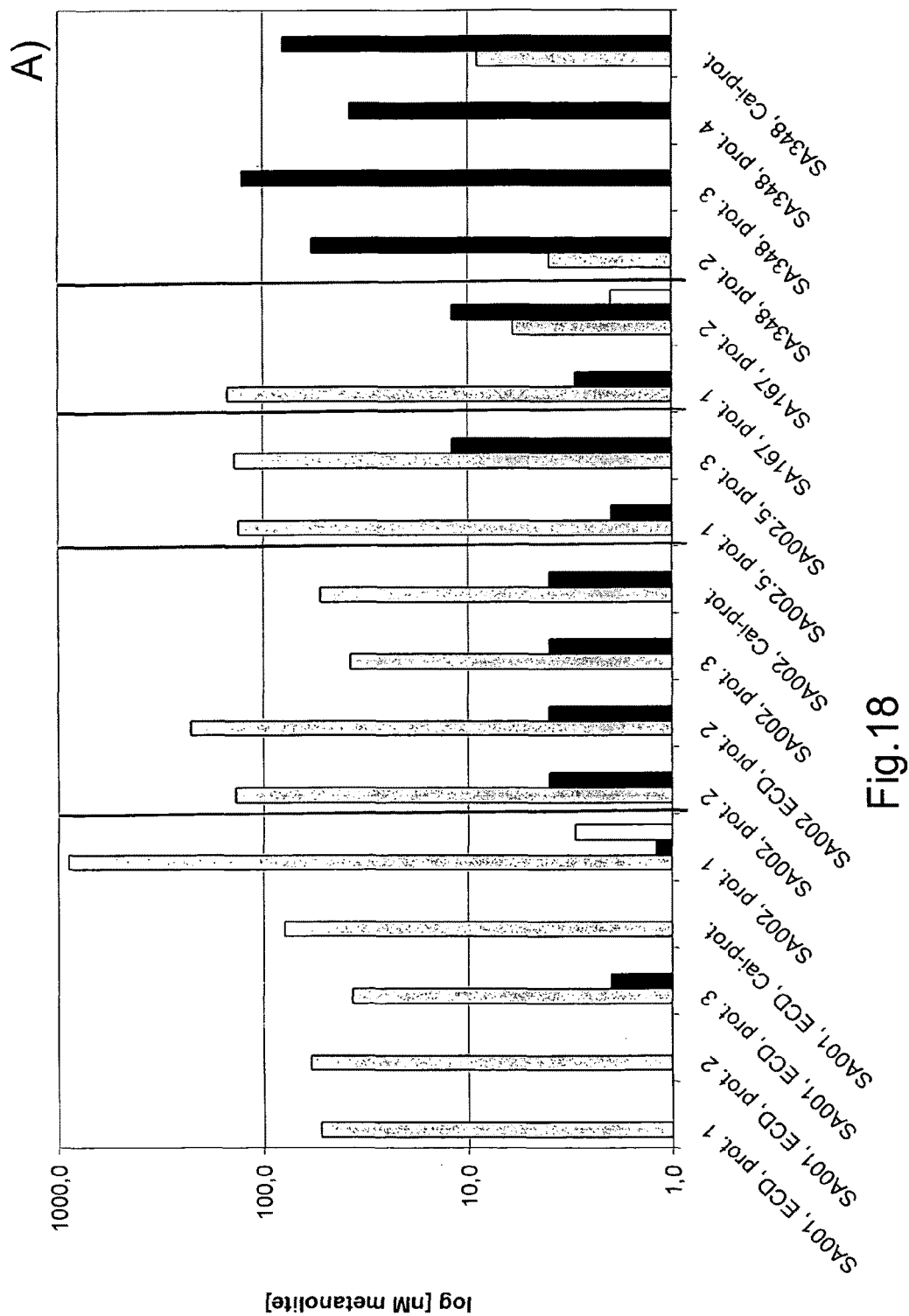
Figure 18:
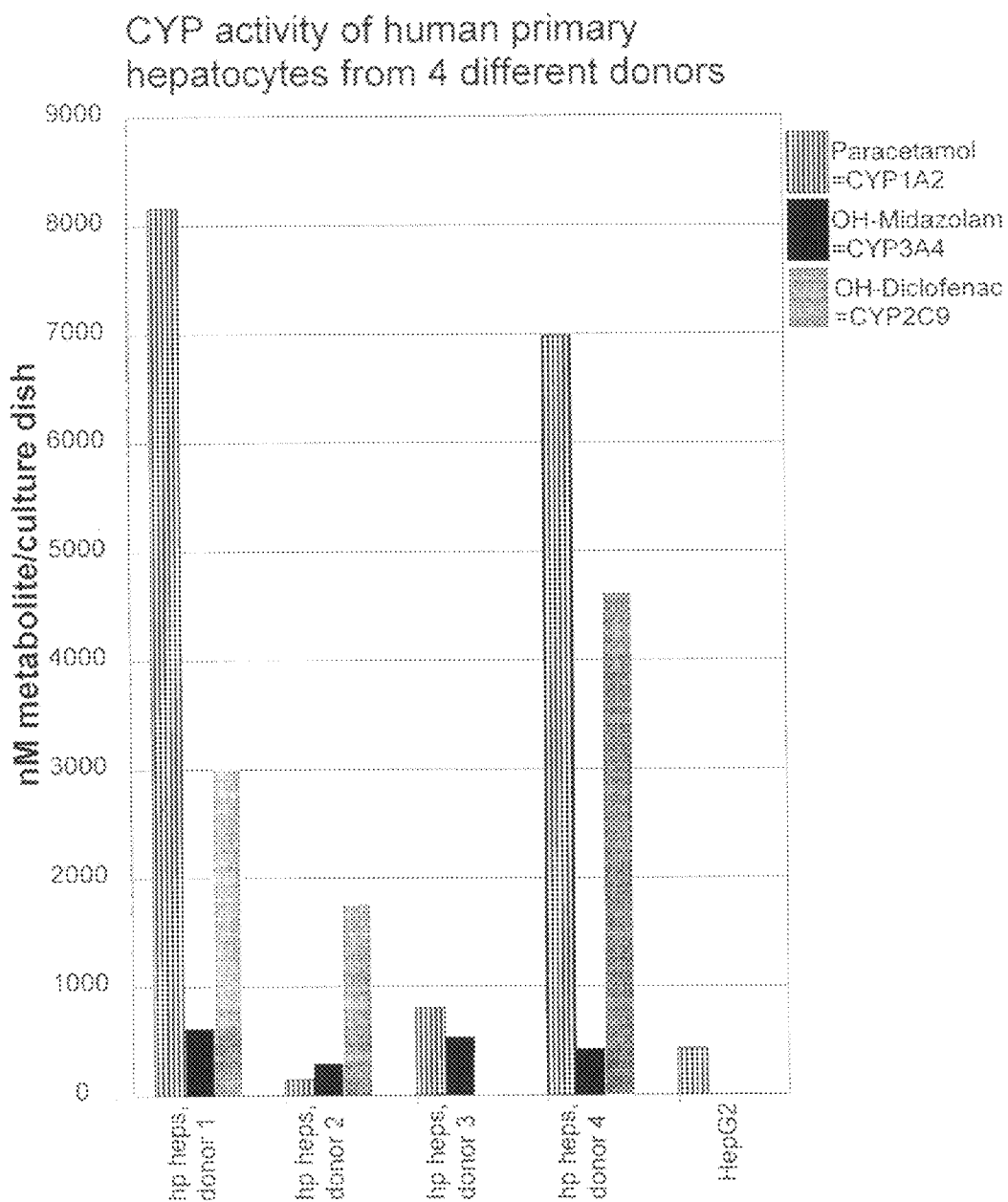
Figure 18:
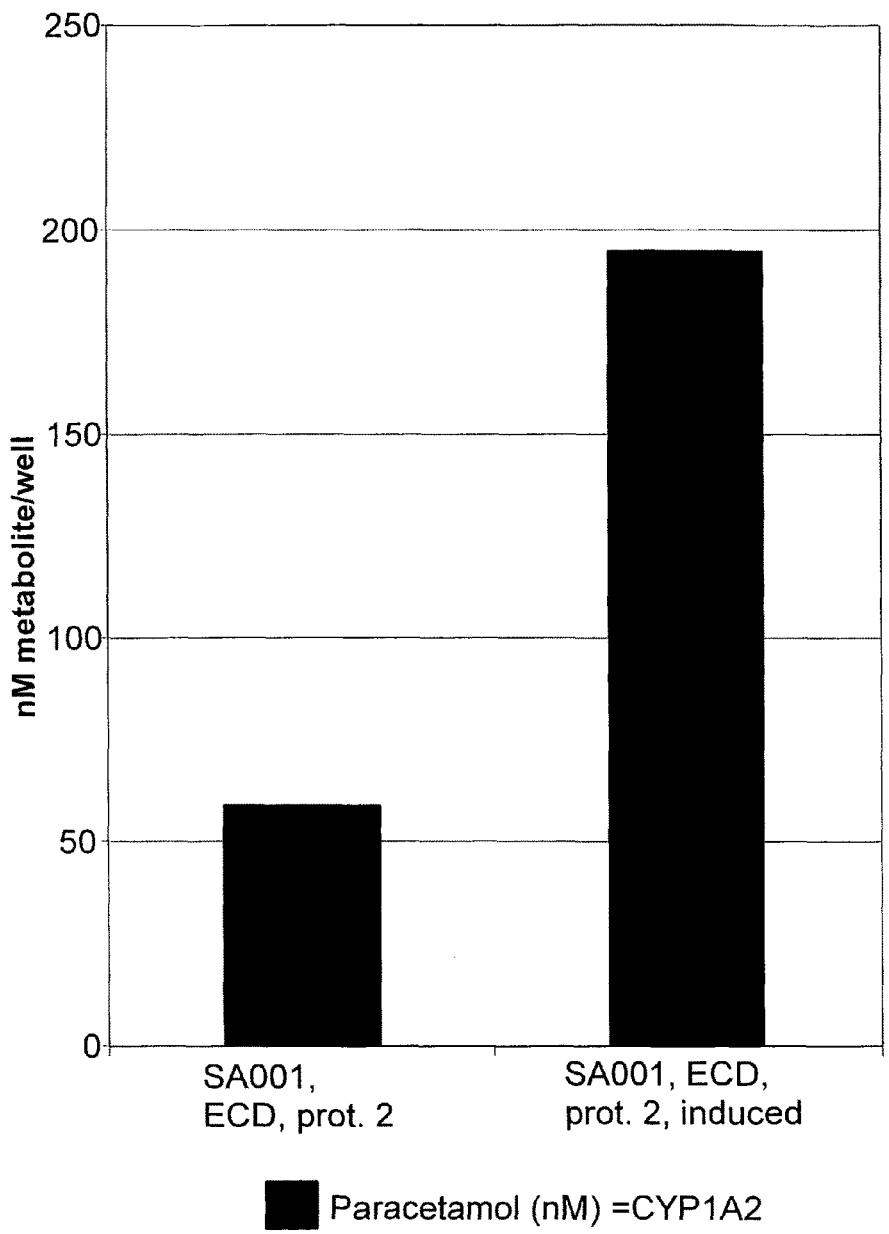
Figure 18:
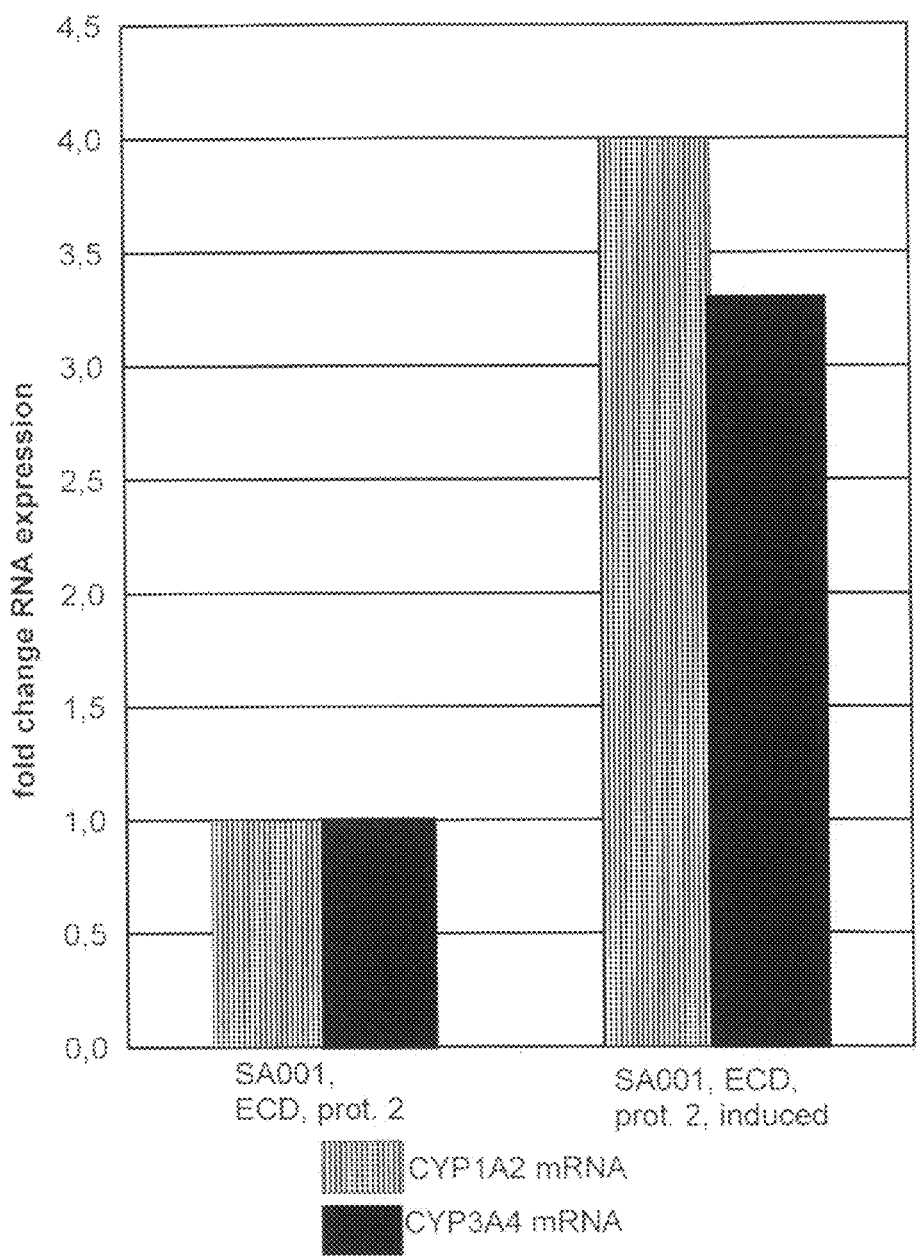

FIG. 18. Comparison of gene expression in DE-Hep cells with human primary hepatocytes and HepG2 cells. See Example 13 for further details.

Figure 19A:
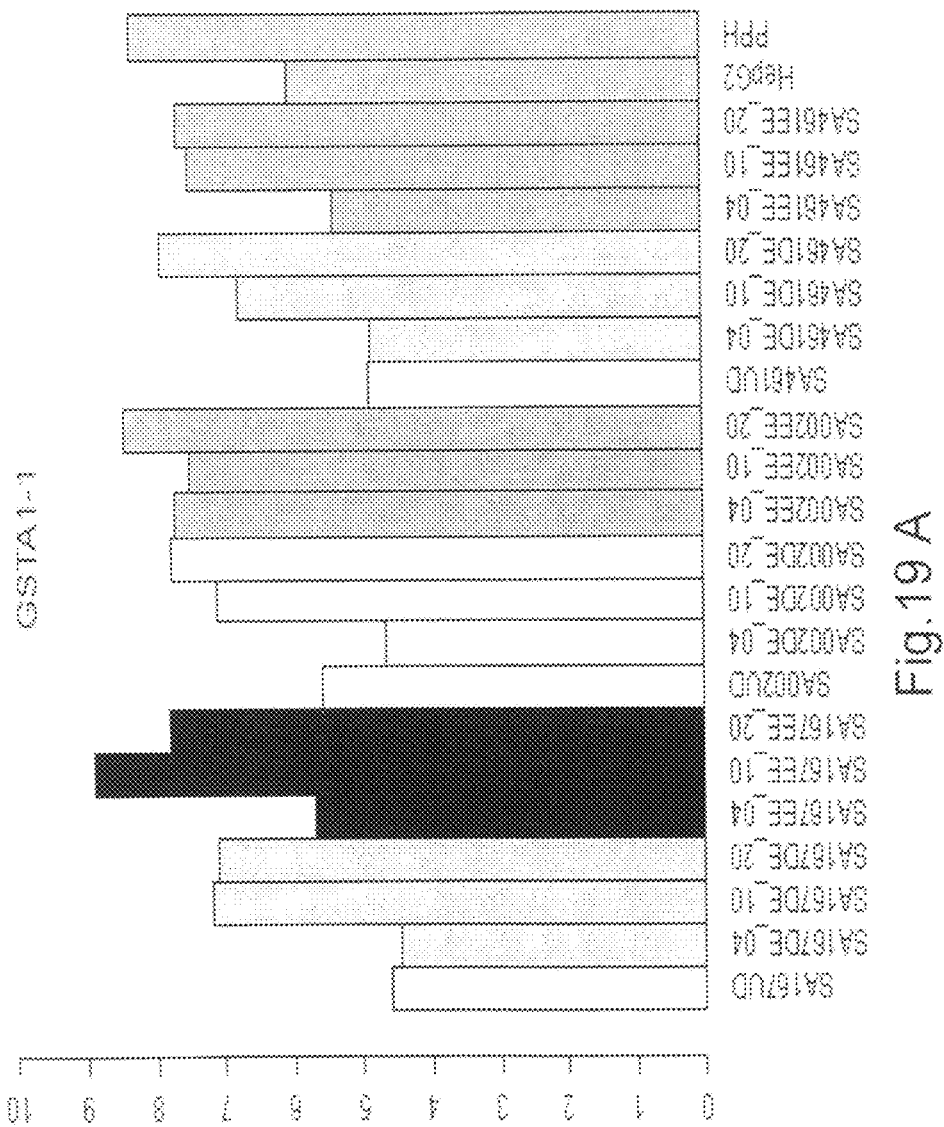

FIG. 19. Expression of phase II enzymes in DE-Hep cultures.

The hBS cell lines SA167, SA002 and SA461 were analysed for the expression of the phase II enzymes glutathione transferase GSTA1-1 (A) and sulfotransferase SULT1 E1 (B). In undifferentiated hBS cultures (abbreviated as UD), expression of both phase II enzymes is low and subsequently upregulated during differentiation of the hBS cell cultures both in DE-Hep cultures (abbreviated as DE) and in intrinsically differentiated hBS cultures (abbreviated as EE). HBS cell cultures were analysed on day 04, 10 and 20. As controls HepG2 and cultured human primary hepatocytes (plated and cultured for 48 hr; abbreviated as PPH) were used.

Figure 20:
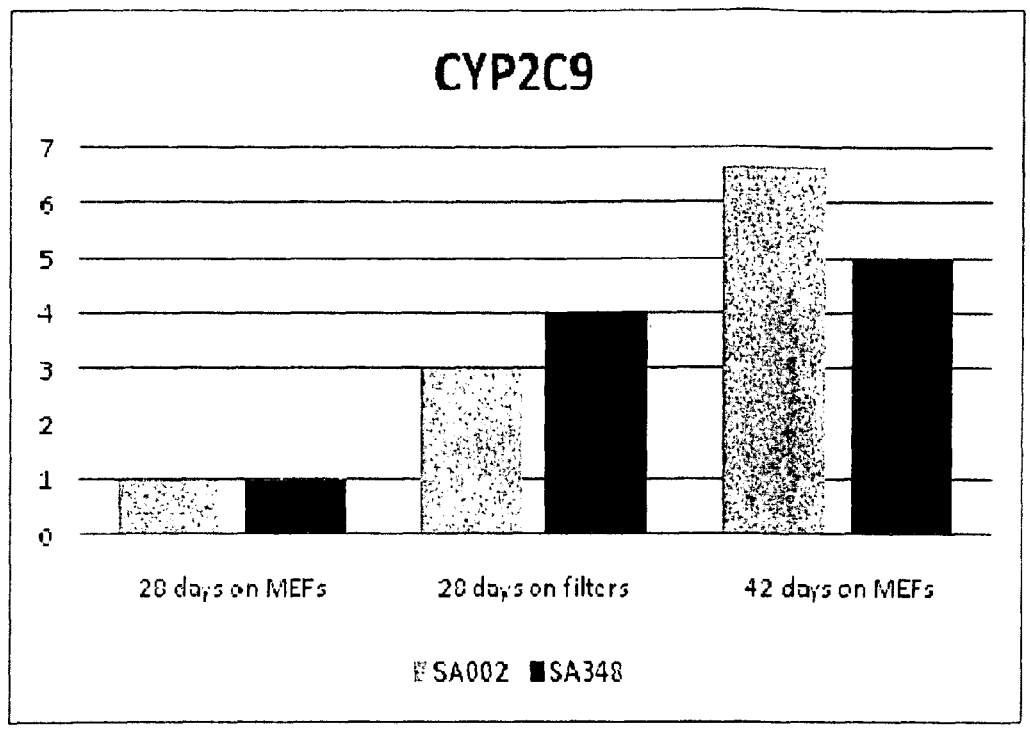

FIG. 20. Improvement of CYP2C9 mRNA expression in DE-hep cells by feeder free culture conditions or by extending the culture period. CYP2C9 mRNA expression relative to the house keeping gene CREBBP in SA002 (grey bars) and SA348 (black bars). 3 biological replicates in 1 experiment, except for SA348 for 42 days which was done in just one replicate.

Figure 21:
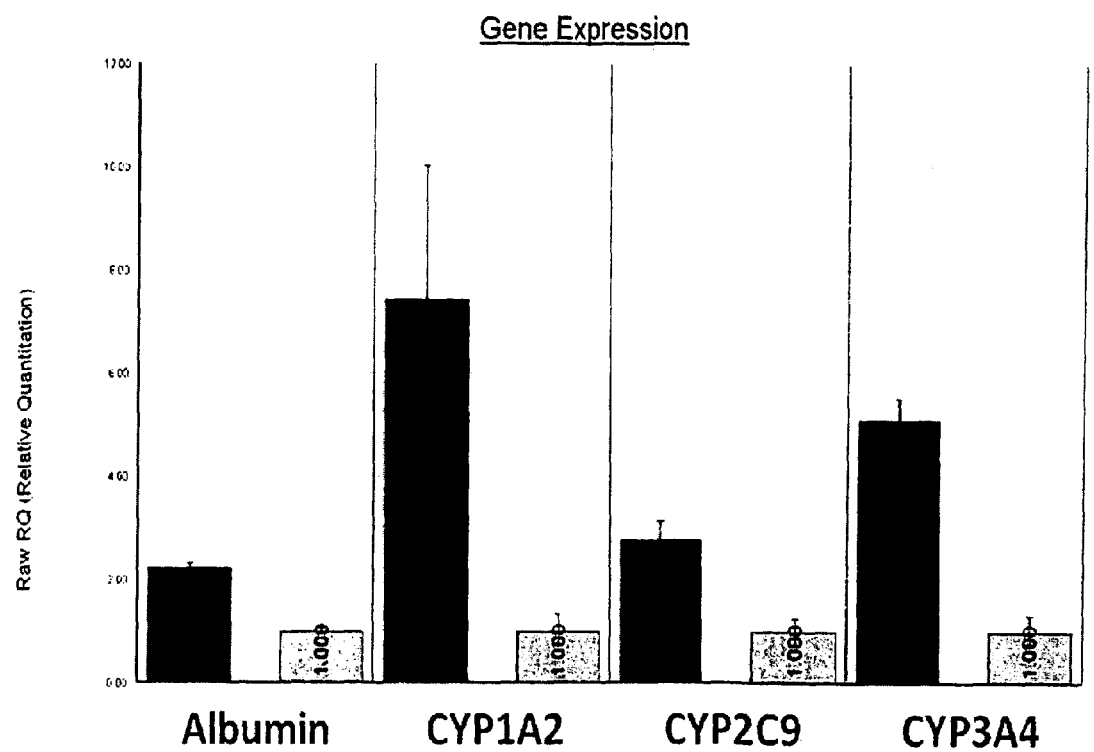

FIG. 21. mRNA expression level of albumin, CYP1A2, CYP2C9 and CYP3A4 relative to the house keeping gene CREBBP in cells derived from the two different protocols: our DE-hep protocol (black bars) and the protocol published by Cai et al (grey bars). The expression levels are shown relative to the Cai protocol.

Figure 22:
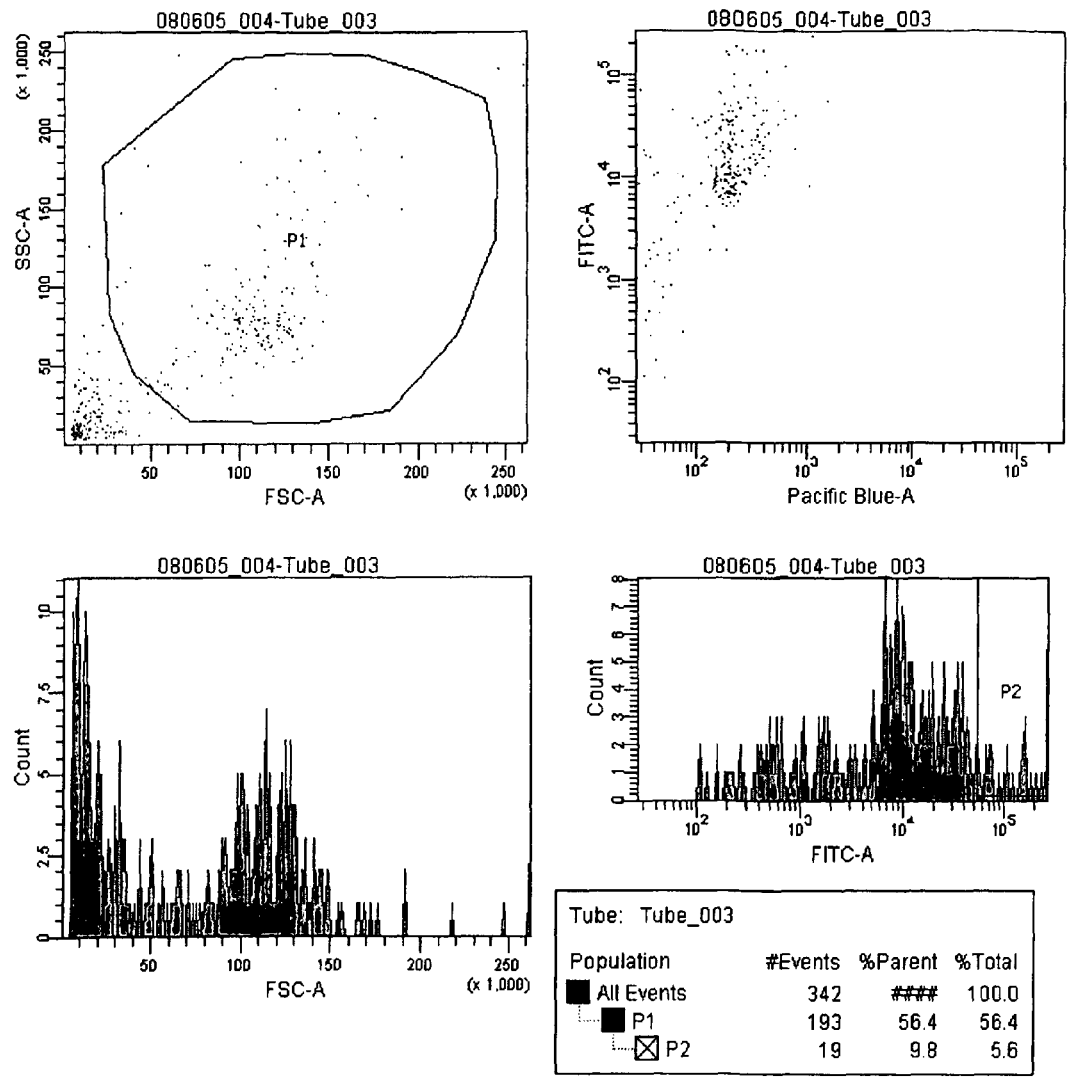
Figure 22:
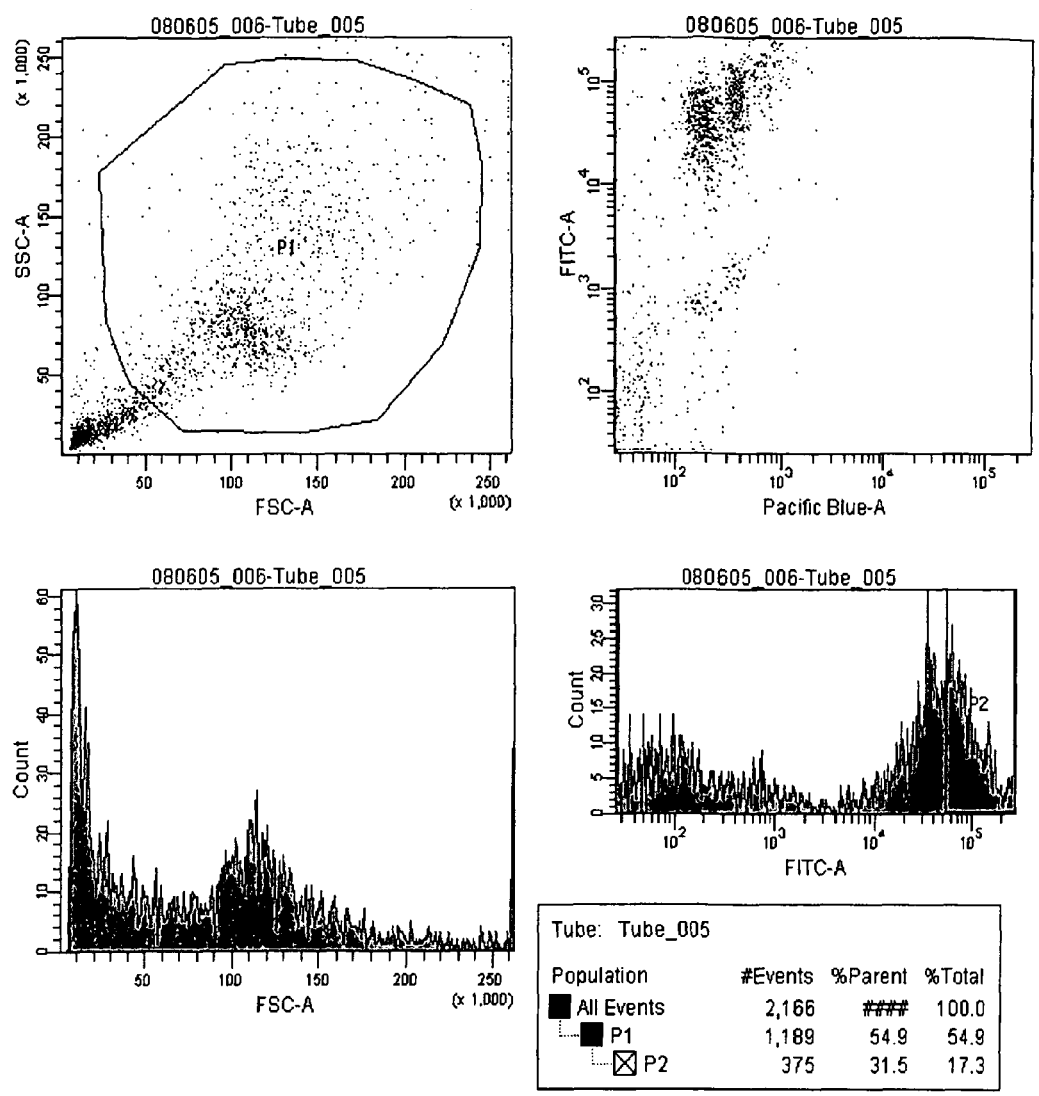
Figure 22:
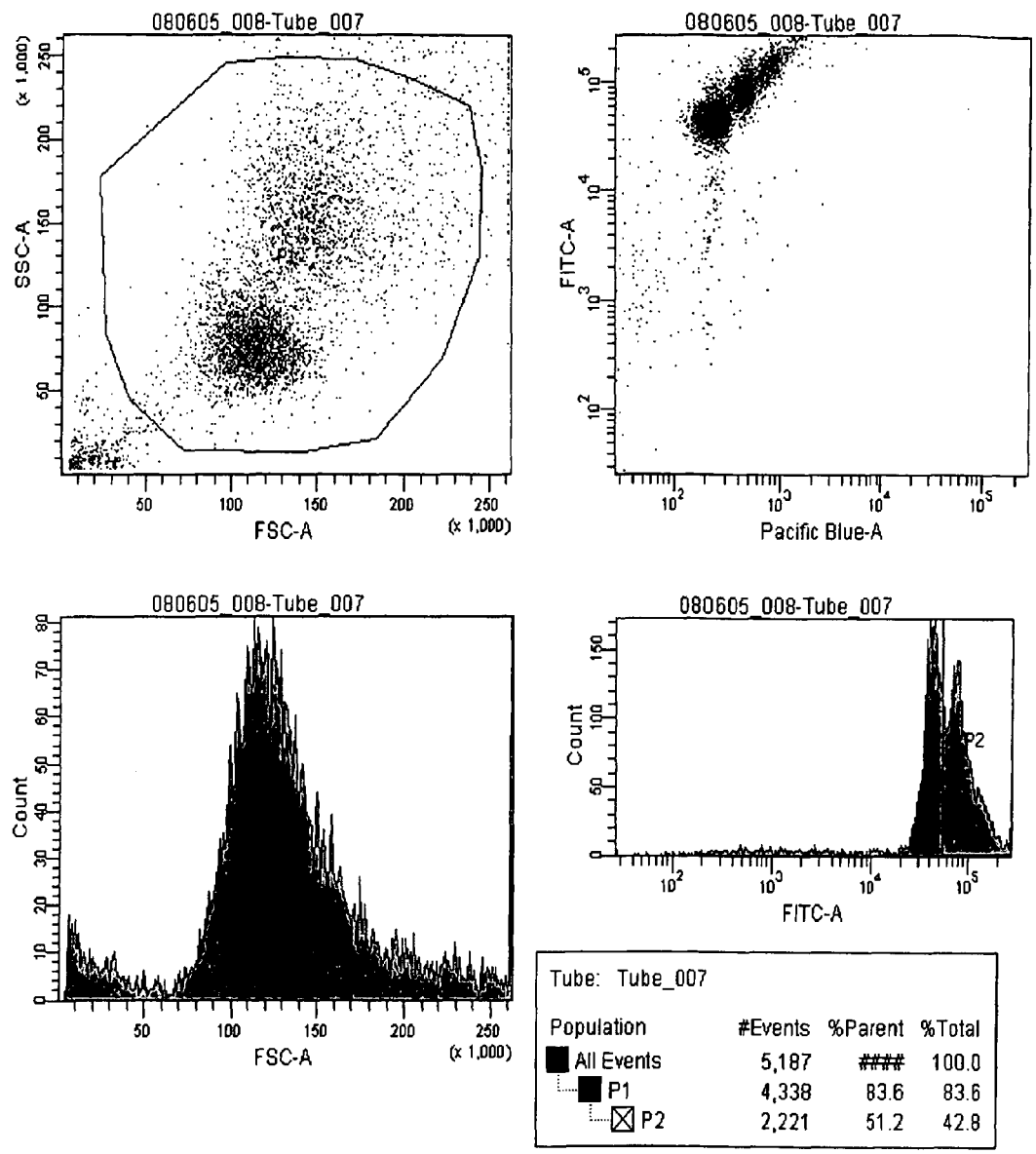

FIG. 22. The corresponding isotype was used as a control for unspecific binding of the monoclonal antibody (FIG. 22. A). Approximately 33.5% of all counted cells (DAPI) were positive for CYP1A2 in the DE-Hep cultures (4218 cells counted) (FIG. 22. B I/II). The primary hepatocytes consisted of 52% CYP1A2 positive cells (20000 cells counted) (FIG. 22. CI/II). Interestingly the DAPI profile depicts mononuclear, binuclear and multinuclear cells in both the DE-Hep and primary hepatocytes (FIG. 22. B, C).

Figure 23:
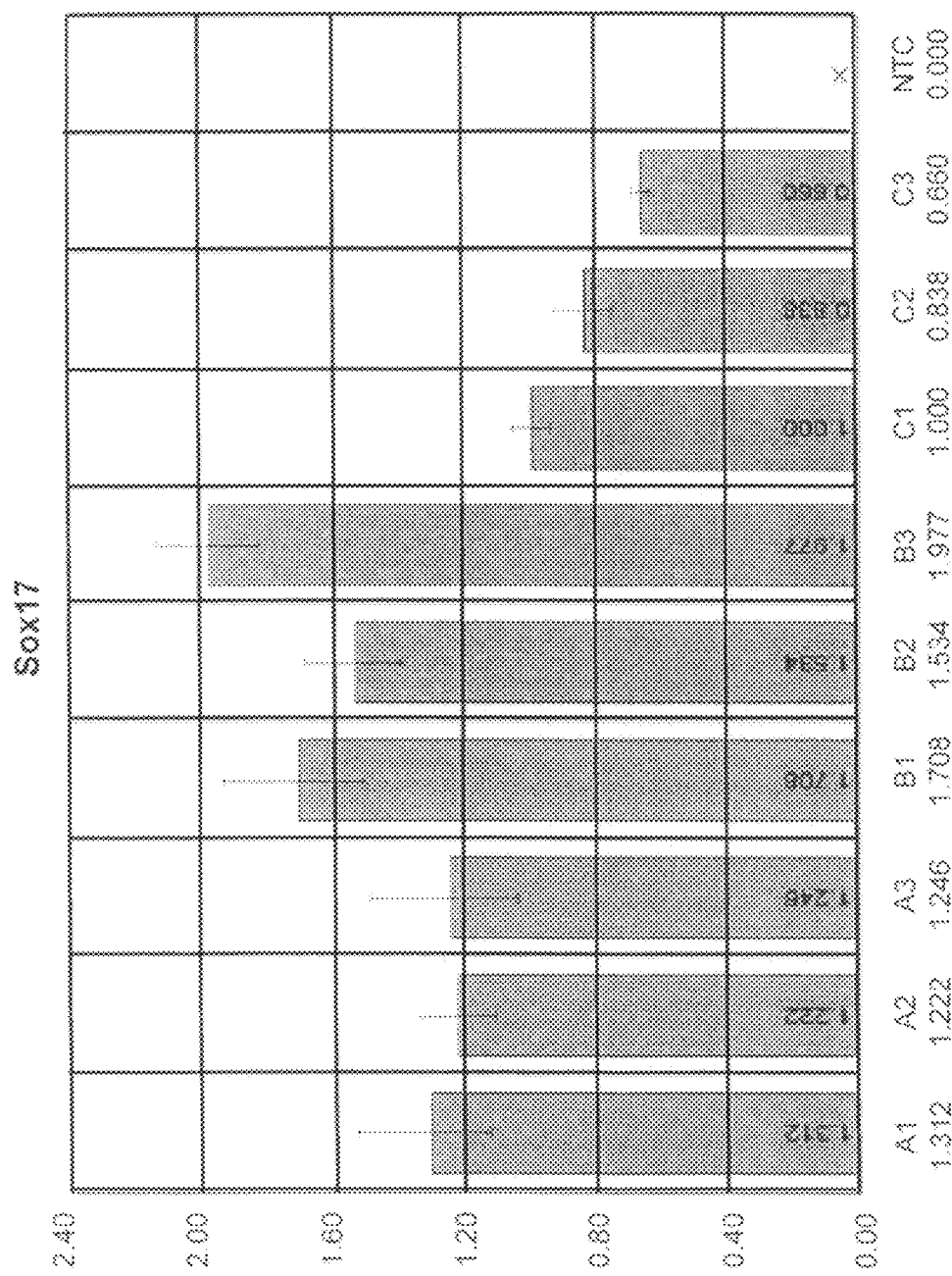
Figure 23A:
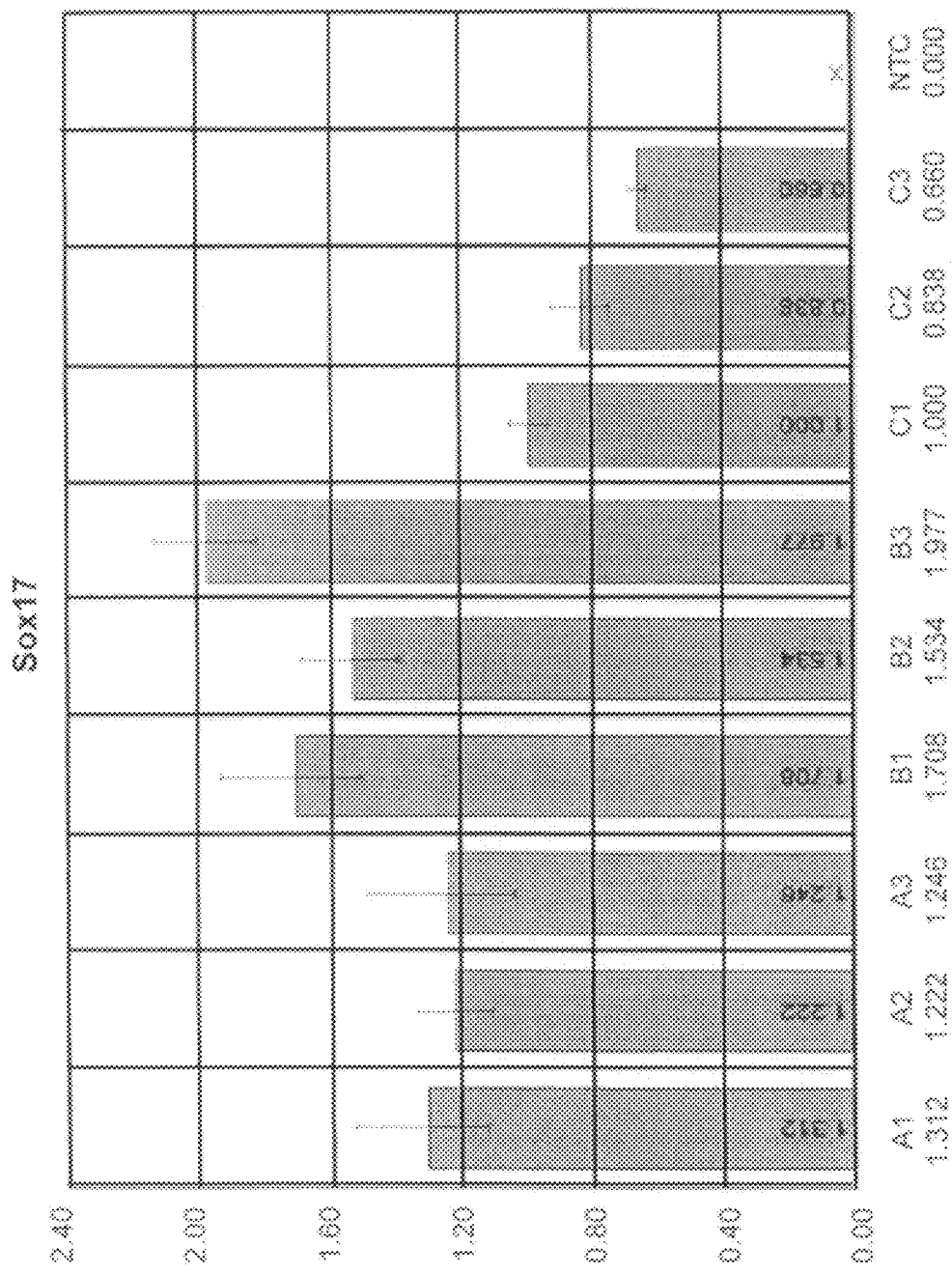
Figure 23B:
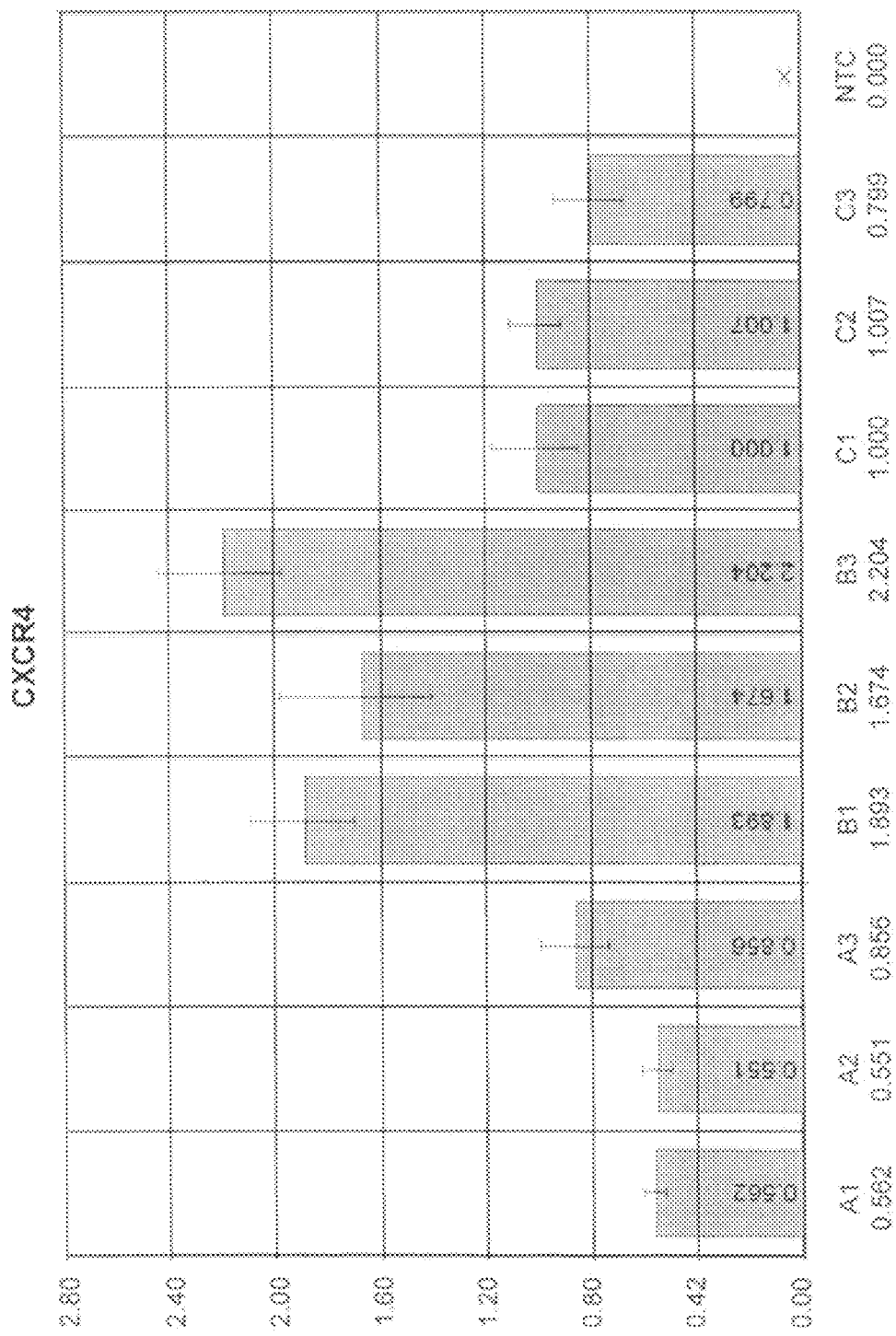
Figure 23C:
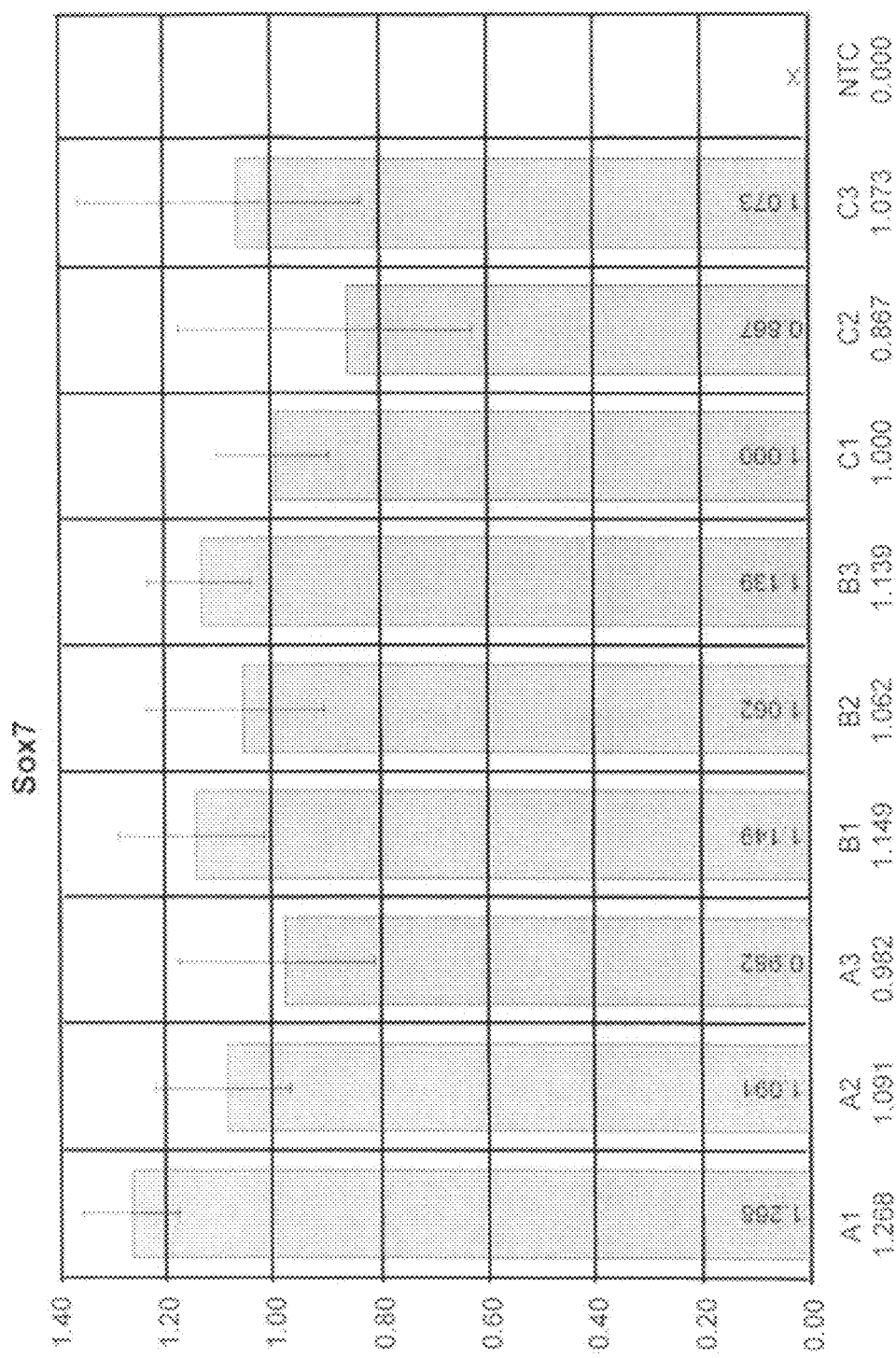
Figure 23D:
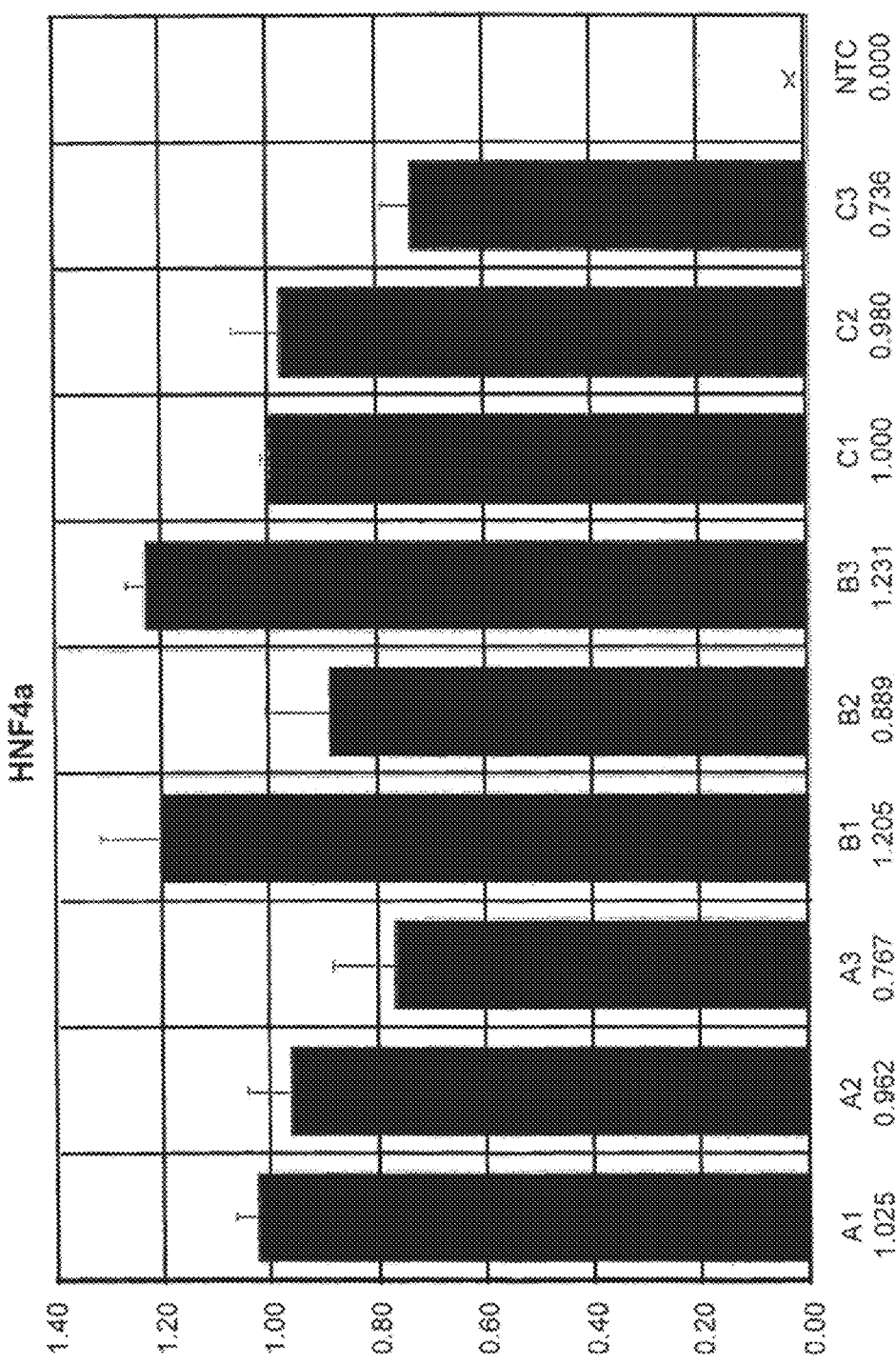
Figure 23E:
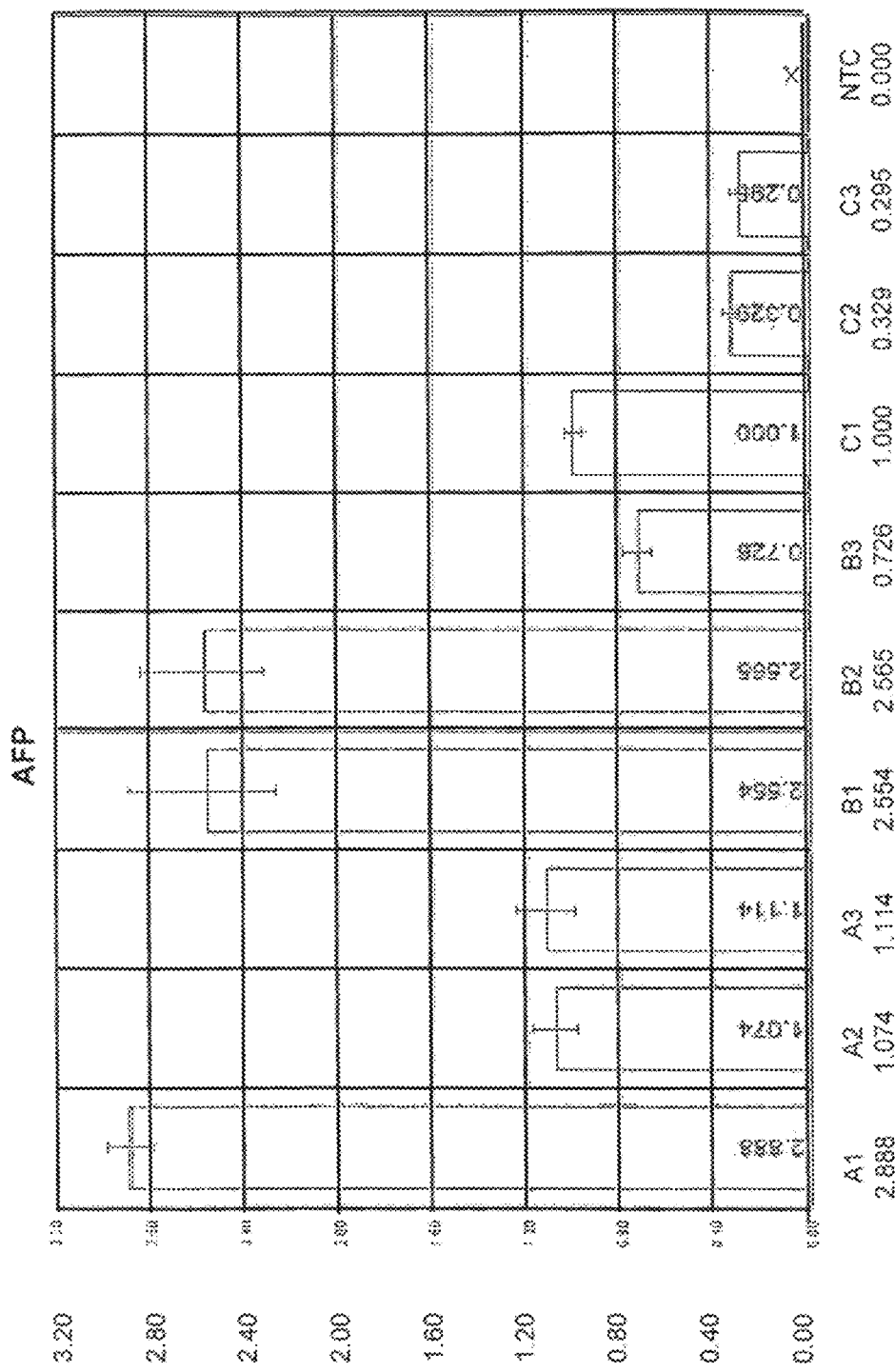
Figure 23F:
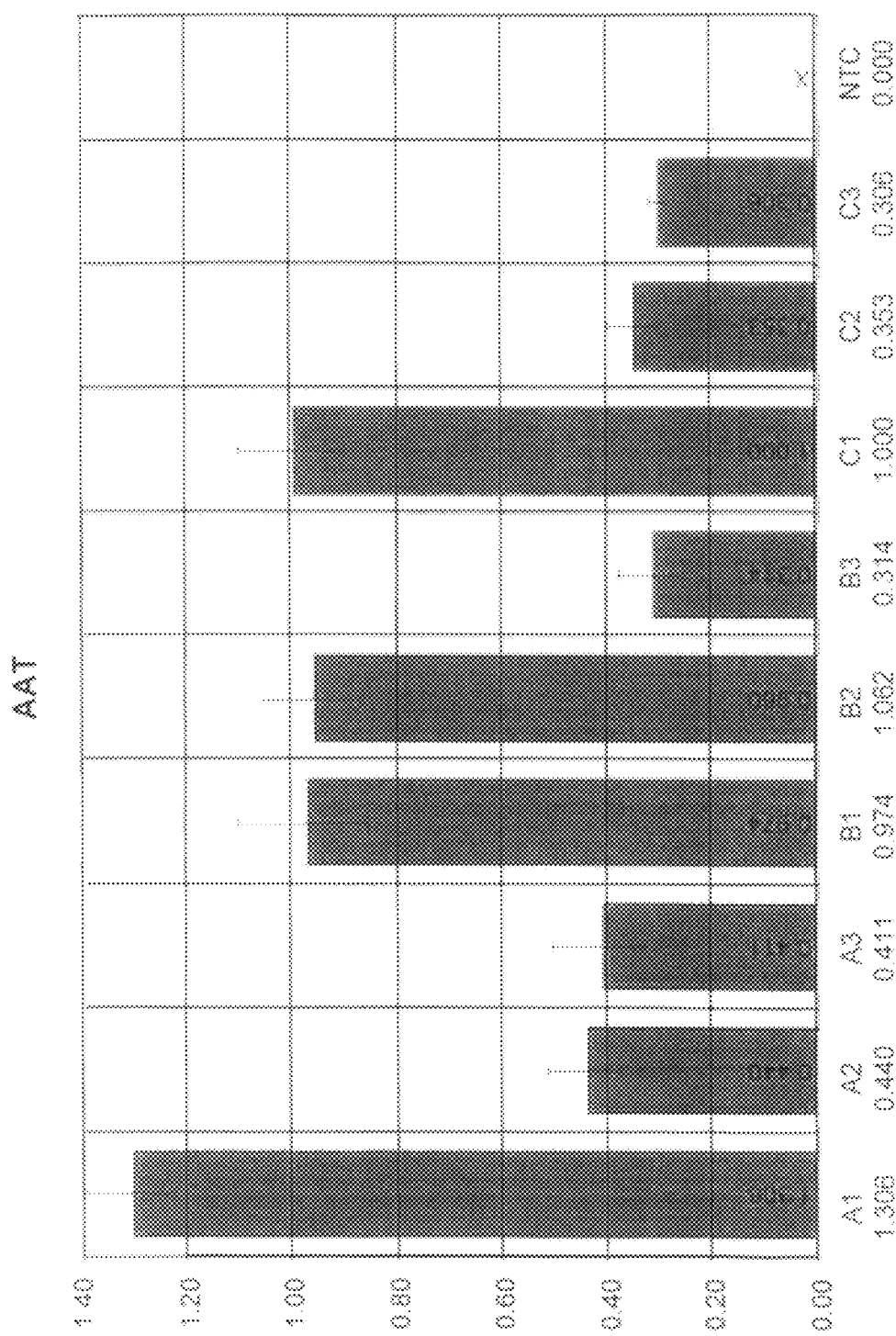
Figure 23G:
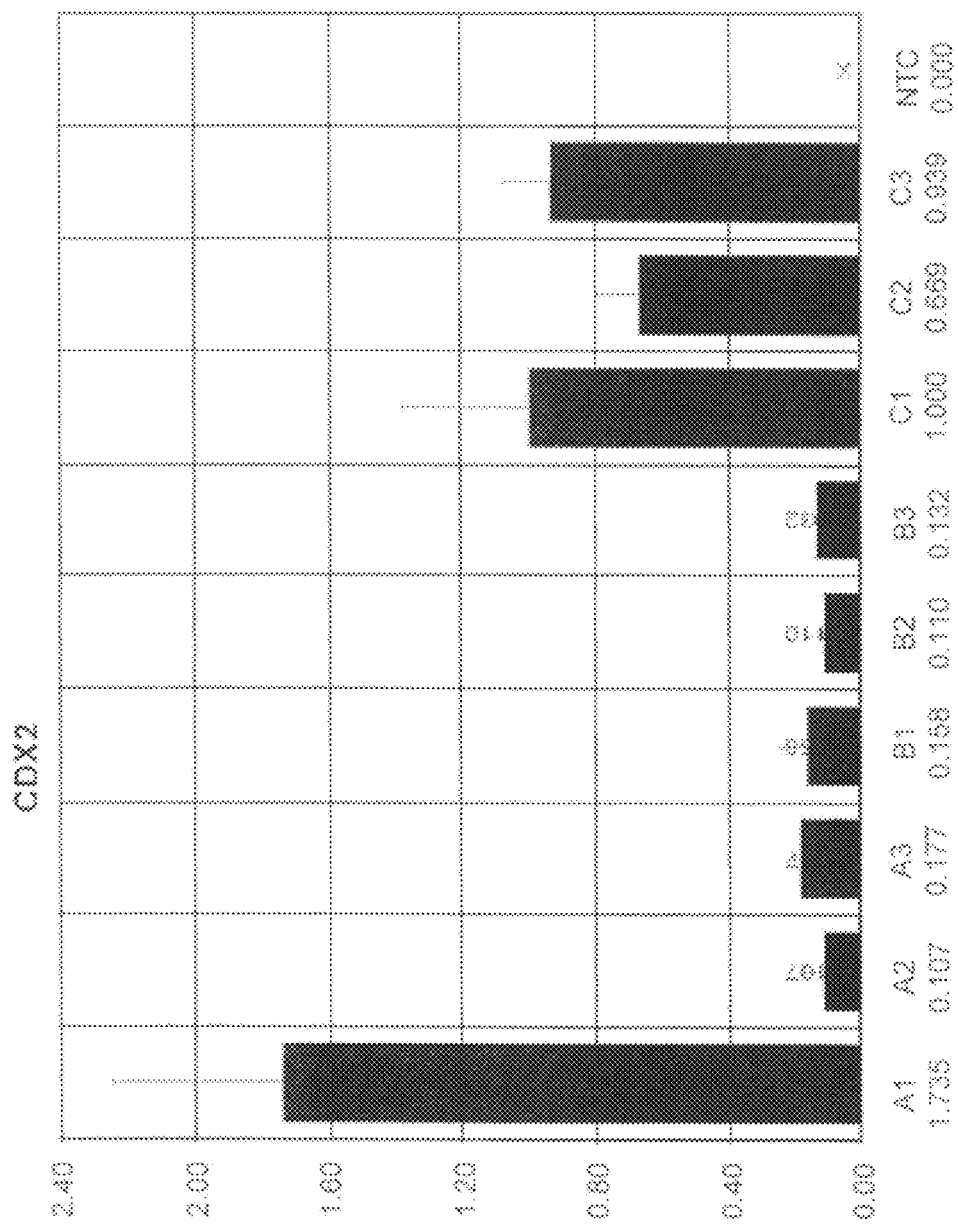

FIG. 23. mRNA expression of genes expressed in definitive endoderm (Foxa2, Sox17 and CXCR4; DE) or genes expressed in extraembryonic tissue (Sox7, CDX2 and AAT; ExE) relative to the house keeping gene CREBBP in hESCs treated with activin A (black bars) or activin B (grey bars). One experiment with 5 biological replicates. DE=definitive endoderm. ExE=extraembryonic tissue.

Methods and Material

Methods
Starting Material
Suitable material, undifferentiated human blastocyst-derived stem cells, can be obtained in the following four different ways, described in detail in the following patent applications;
 1. hBS cell line establishment and LOT preparation (WO03055992)
 2. hBS cells transferred to a feeder-free culture system (WO2004099394)
 3. Xeno-free preparation (WO2007042225 A3)
 4. Enzymatically passaged hBS cells (WO07107303)

The xeno-free preparation is especially important when the DE-hep cells are used for therapeutic purposes.

EXAMPLES

Example 1

Starting Material
The starting material for the present invention is suitably pluripotent undifferentiated hBS cells, such as undifferentiated hBS cell lines. Such material can be obtained from Cellartis AB, www.cellartis.com. Cellartis AB is the largest source of defined hBS cell lines world wide and has more than 30 hBS cell lines and subclones available today. Two of the cell lines are listed in the National Institutes of Health (NIH) Human Embryonic Stem Cell Registry, http://stemcells.nih.gov/research/research/registry/ and 20 in the UK Stem Cell Bank. Additionally, Cellartis can provide hBS cell lines approved for research use by major markets such as Japan, Germany and France. For the present invention hBS cell line SA002, SA002.5, SA034, SA167, SA181, SA348 and SA461 were used specifically. Characteristics of the hBS cells recommended as starting material are the following: positive for alkaline phosphatase, SSEA-3, SSEA-4, TRA 1-60, TRA 1-81, Oct-4, negative for SSEA-1, telomerase activity, and pluripotency in vitro and in vivo (the latter shown by teratoma formation in immuno-deficient mice). (Methods and protocols as previously shown, Heins et al, WO03055992.)

LOT Preparation and Characterization Program

The LOT preparation of hBS cell lines constitutes an expansion of the hBS cells in culture and a subsequent freezing of more than 100 straws in one single passage according to a standardized method (patent pending, WO2004098285). The morphology of the hBS cell lines are monitored before and after freezing and also in consecutive passages in the subsequent culturing after thawing of cells from the LOT. The quality of the LOT freezing is verified by an examination of the thawing recovery rate, which shall show a thawing rate of 100% for each straw of 10 thawed, i.e. cell material can be subcultured from each individual vitrified straw upon thawing. A safety test concerning microbiological safety is then performed on the cells and the media in the passage of freezing to make sure the cells are free from contamination. The characterization program performed includes a broad range of methods to validate the differentiation status the of the hBS cell lines. At first a marker expression analysis of the commonly accepted markers for undifferentiated cells (SSEA-1, SSEA-3, SSEA-4, TRA-1-60, TRA-1-81, Oct-4 and ALP) is performed. The genetic stability of the cells through out passage and freezing-thawing cycles is checked through karyotyping and FISH. The telomerase activity is measured using a Telo TAGGG Telomerase PCR ELISA$^{PLUS}$ kit. The pluripotency of the hBS cells are examined by in vitro differentiation via an embryoid body step and through in vivo differentiation by transplantation of hBS cells under the kidney capsule of immuno-deficient SCID mice.

The starting material used herein may furthermore be completely xeno-free derived whereby completely xeno-free hepatocyte-like cells may be obtained for potential use in regenerative medicine and so significantly decreasing the risks of graft rejection and potential transfer of non-human pathogens. For xeno-free derivation of hBS cells all medium and matrix components, feeder cells and other material used may not be derived from or been in contact with any non-human animal material. Suitable components for xeno-free derivation of hBS cells and furthermore xeno-free hepatocyte-like cells are xeno-free derived human fibroblasts, such as human foreskin fibroblasts (HFF), serum-free or human serum based culture medium with human recombinant growth factors, differentiation factors and/or potential other additives, and either human recombinant enzymes or sterile mechanical tools for dissociation and propagation of the cells.

Furthermore, the starting material for deriving DE-Hep cells are hBS cells on feeder cells such as mouse embryonic fibroblasts or human foreskin fibroblasts or in feeder-free systems on surfaces such as Matrigel or Collagen etc. hBS cells can be passaged enzymatically and/or manually before and/or during the experiments onto the same kind of matrix or a different matrix and the same kind of medium or a different medium.

Example 2

Inducing Undifferentiated hBS Cells into DE and Further into Functional Hepatocytes Undifferentiated hBS cells were maintained and propagated in vitro. At day 4-7 after passage undifferentiated hBS cell colonies were treated according to a basic differentiation program. Each step in this protocol is characterized by key components that are crucial;

Stage I, Definitive endoderm (DE): low serum and Activin A
Stage II, DE-Hep progenitor cells: members of the TGFbeta superfamily of proteins, especially BMP4
Stage III, functional DE-Hep cells: HGF Changes in growth factor exposure time, concentration, various combinations of them and length of treatment have been tested An overview of the basic method and variations is presented in FIG. 1a. The undifferentiated hBS cells are induced to DE by incubation with Activin A (100 ng/ml) for 3-5 days in RPMI Advanced medium or DMEM medium or a comparable medium (stage I, day 0). The medium is changed every day. The first day of Activin A induction the serum concentration is zero and the medium is supplemented with or without Wnt3A (25 ug/ml) and/or FGF2. Starting from the second day of stage I, 0.2% FCS, Activin A and/or FGF2 is supplemented the medium. After the Activin induction the cells are incubated in their conditioned media for additionally 1-3 days without medium change after which stage II is started (variation of the basic protocol). During stage II the cells are incubated in RPMI Advanced or DMEM medium or a comparable medium supplemented with BMP4 and FGF2 and/or different concentrations of aFGF, bFGF, BMP2 and HGF in sequential steps (see variations of the basic protocol, FIG. 1a). The medium is changed every to every second day. During stage III the DE-derived hepatocytes (DE-Hep cells) are maturated.

Stage I: Differentiation into Definitive Endoderm

Previously it has been shown that hBS cells can differentiate into definitive endodermal cell types upon exposure to well defined growth factors (Activin A). In the present invention several cell lines (SA001, SA002, SA002.5, SA034, SA167, SA181, SA348 and SA461) have been induced by growth factors (GFs) to generate hepatic cells via definitive endoderm (DE) which are then called DE-Hep cells. Our strategy involves three differentiation stages that mimic important steps in liver development, as described below. In the first differentiation phase (Stage I, see FIG. 1a) Activin A induces hBS cells into DE which takes 1 to 5 days. In stage II early hepatic cell types are induced by BMP4 or/and other factors and these early hepatic cells expand and maturate. In the last phase, stage III, terminal maturation is achieved by HGF, OSM, DEX for up to several days (FIG. 1a).

We used Activin A, and Activin A in combination with Wnt3a and/or FGF2 to generate DE. After 4 to 5 days in Stage 1 the hBS cell colony differentiated and genetic markers for early DE were examined using quantitative real-time real time-PCR (Q-PCR). Activin A induced a strong wave of early endoderm at day 3 to 5, and was highlighted by high expression levels of Sox17, HNF3beta (HNF3b or HNF3b) and Cxcr4 expression (FIG. 4) and then reduced to near baseline levels (data not shown). Interestingly the combination of Activin A and FGF2 yielded a higher expression of Sox17 (more than two times higher), HNF3b (more that 1.5 times higher) and Cxcr4 (nearly 1.5 times higher) compared to Activin A alone (FIG. 4). Untreated hBS cells had significantly less Sox17, HNF3b and Cxcr4 than growth factor treated cultures. In addition, the control culture had significantly less Sox17, HNF3b and Cxcr4 gene expression. Furthermore they up regulate early liver markers like AFP or AAT. At this early stage in differentiation and development, this indicates the presence of extraembryonic endoderm (ExE) in intrinsically differentiating colonies (FIGS. 5 and 10). The expression data were confirmed by co-staining of Sox17/Sox7, Sox17/Cxcr4, Sox17/Oct4, Sox7/HNF3b (data not shown). After 4 days in Activin A more than 70% of the remaining cells were Sox17, and only few were found to be Sox7 or double positive for HNF3b and Oct4. The changes of gene expression after Activin A treatment were associated to morphological changes and distinct differentiation pattern of the colonies (FIG. 2). After 4 to 5 days induction with Activin A containing medium cells gathered together and formed a ring of epithelial cells around the colony. Those homogenously growing cells expanded over the plate and could be passaged to a mouse feeder layer containing plate and/or other matrixes. Together these findings show that all the cell lines used herein are capable of differentiating into definitive endodermal cell types after exposure to Activin A. Furthermore the early occurring high AFP expression levels indicate that untreated intrinsic differentiated hBS cell cultures generate mainly extra embryonic endoderm (ExE). See FIGS. 4 and 5, example 5.

Stage II: Hepatic Induction

In stage II (FIG. 1) the cell were exposed to growth factors combinations to induce liver development. The culture strongly responds to the growth factors added the culture medium and forms homogenous epithelial cells grouped in small clusters. After some more days a rather heterogeneous population of liver-like cells develops, among which many cell types are grouped together in clusters (FIG. 6). Moreover, in the second stage, after 6-9 days (after induction by Activin A), the first polygonal-shaped cells with few bi-nucleated cells appeared (FIG. 6).

We evaluated by gene expression analysis whether these morphological changes were associated with distinct differentiation pattern at the molecular level. Whole dissected colonies were analysis by Q-PCR showing that in both, control as growth factor induced cultures, expression of early liver markers AFP, HNF4a, HNF3b, Albumin, CK7, CK8, CK18, CK19 and HNF1a positive could be detected. Upon exposure to liver-specific factors (Stage II), the levels of liver markers were significantly higher compared to the control cultures.

To support the findings obtained by Q-PCR, immunohistochemical analysis were performed. Both control as well as phase II cultures expressed the early liver markers.

Stage III: Hepatic Maturation

In stage III, the cultures were subsequently changed to a medium containing HGF, FGF2, and FGF1 for 2-3 days. In protocol 1, a specific embodiment of the invention (FIG. 1b) the medium was changed during Stage II to different media containing aFGF, bFGF, BMP2, BMP4, HGF with different concentrations and with 0.2% Serum. At these stages many DE-Hep cells emerged and exhibited typical hepatocyte morphology with a polygonal shape, containing distinctive nuclei with a nucleoli. Interestingly they were arranged in small islet-like clusters starting at mid to late stage II (FIGS. 6 and 9).

During stage III, the cells were further cultured in HCM medium for maturation. At this stage whole colonies were dissected and analyzed by Q-PCR. The results showed that the expression of hepatocyte markers (Albumin, CYP3A4 and UGT2B7) were significantly upregulated compared to intrinsically derived hepatocyte-like cells. Immunostainings at the end stages in both protocols showed that many DE-Hep cells were positive for CYP1A2, CYP3A4/7, CK18, CK8, CK19 and HNF4alpha (table 2). Interestingly the expression of the polarized transporter protein MRP2 could be detected in the DE-Hep cultures but not in the untreated control cultures. The control cultures were intrinsically differentiated cells, see definitions.

One Specific Embodiment of the Invention, Protocol 1:

The following specific conditions were used in this specific embodiment, protocol 1, see FIG. 1b.

Stage I: DE Induction

Definitive endoderm was induced in stage I by cultivation in RPMI advanced medium or DMEM medium or a comparable medium supplemented with 1% PEST, 1% Glutamax and FGF2 (4 or 5 ng/ml) and additionally with;

Day 1: Activin A, Wnt3A (100 ng/ml, 25 ng/ml) 0% FCS
Day 2: Activin A (100 ng/ml) 0.2% FCS
Day 3: Activin A (100 ng/ml) 0.2% FCS
Day 4: Activin A (100 ng/ml) 0.2% FCS The cells were cultured 2-3 days without medium change. The protocol combines the medium supplements, Activin A and bFGF.

Stage II: DE-Hep Progenitor Expansion

For derivation and expansion of DE-Hep progenitors RPMI advanced medium or DMEM medium or a comparable medium was used and supplemented with 1% PEST, 1% Glutamax and additionally with;

Day 5: aFGF, bFGF, BMP2, BMP4 (100 ng/ml, 5 ng/ml, 50 ng/ml, 200 ng/ml, respectively) 0.2% FCS.
Day 6: aFGF, bFGF, BMP2, BMP4 (100 ng/ml, 5 ng/ml, 50 ng/ml, 200 ng/ml, respectively) 0.2% FCS.
Day 7: bFGF, BMP4, HGF (50 ng/ml, 200 ng/ml, 50 ng/ml, respectively) 0.2% FCS.
Day 8: bFGF, BMP4, HGF (50 ng/ml, 200 ng/ml, 50 ng/ml, respectively) 0.2% FCS.
Day 9: bFGF, BMP4, HGF (50 ng/ml, 200 ng/ml, 50 ng/ml, respectively) 0.2% FCS.

The DE-Hep progenitors were cultured in stage II medium from day 9 up to day 20 with medium change every second day. A relatively high HGF concentration (100-200 ng/ml) was used for the first days.

Optionally;

Day 6: BMP4 (50 ng/ml), FGF2 (4 ng/ml), 0.2% FCS,
Day 7: BMP4 (50 ng/ml), FGF2 (4 ng/ml), 0.2% FCS
Day 8-9: FGF1 (50 ng/ml), FGF2 (4 ng/ml), 1% FCS
Day 10: HGF, FGF2 (50 ng/ml, 4 ng/ml, respectively), 1% FCS
Day 11-13: HGF, FGF2, EGF (50 ng/ml, 4 ng/ml, 10 ng/ml, respectively), 1% FCS Giving a higher FCS concentration and a supplement of EGF (10 ng/ml) at day 11 to 13.50% of the medium was changed every day.

Stage III: DE-Hep Maturation

For maturation of hepatic cells derived from definitive endoderm (DE-Hep cells) Williams E based medium or HCM medium or a comparable medium was used and supplemented with 1% PEST, 1% Glutamax and at day 10 additionally with: OSM, Dex, ITS mixture, BMP4, HGF (10 ng/ml, $10^{-7}$ M, 1×, 200 ng/ml, 50 ng/ml, respectively), 0% FCS. Up to day 15 the medium was change every day.

A high HGF concentration (100-200 ng/ml) was used for incubation longer than 6 days. A high concentration of Dexamethasone (Dex) was used (100 µM). After day 15 a Williams E based medium (1% PEST, 1% Glutamax) was used supplemented with Sodium Butyrate, HGF (2.5 mM, 2.5 ng/ml, respectively) and 0% FBS. Medium change every second day from day 16 to 21.

One Specific Embodiment of the Invention, Protocol 2:

The following specific conditions were used in this specific embodiment, protocol 2, see FIG. 1b.

Stage I: DE Induction

Definitive endoderm was induced in stage I by cultivation in RPMI advanced medium or DMEM or a comparable medium supplemented with 1% PEST, 1% Glutamax, bFGF (4 or 5 ng/ml) and additionally with;

Day 1: Activin A (100 ng/ml) 0% FCS
Day 2-3: Activin A (100 ng/ml) 0.2% FCS

The cells were cultured 2 days without medium change. The protocol combines the medium supplements, Activin A and bFGF.

Stage II: DE-Hep Progenitor Expansion

For derivation and expansion of DE-Hep progenitors HCM medium (in some cases the HCM-antibiotic mix GA1000 was omitted) or a Williams E based medium or a comparable medium was used and supplemented with 1% PEST, 1% Glutamax and additionally with HGF (20 ng/ml) and 0% FCS.

Day 6-12: HGF (20 ng/ml) 0% FCS.

The DE-Hep progenitors were cultured in stage II medium from day 6 up to day 12 with medium change every 2-3 days.

Stage III: DE-Hep Maturation

For maturation of hepatic cells derived from definitive endoderm (DE-Hep cells) HCM medium (in some cases the HCM-antibiotic mix GA1000 was omitted) or a Williams E based medium or a comparable medium was used and supplemented with 1% PEST, 1% Glutamax and at day 13 additionally with: OSM, Dex, (10 ng/ml, $10^{-7}$ M), 0% FCS. The medium was change every 2-3 days. The DE-Hep cells were cultured in this medium for a minimum of 22 days and up to 35 days.

In some cases EGF and ascorbic acid were omitted during the last days or the last week before analysing the DE-Hep cultures and a positive effect on maturation and functionality of the cells was observed. Without EGF and ascorbic acid proliferation is not stimulated anymore which leads to increased maturation instead.

One Specific Embodiment of the Invention, Protocol 3:

The following specific conditions were used in this specific embodiment, protocol 3, see FIG. 1b.

Stage I: DE Induction

Definitive endoderm was induced in stage I by cultivation in RPMI advanced medium or DMEM or a comparable medium supplemented with 1% PEST, 1% Glutamax, bFGF (4 or 5 ng/ml) and additionally with;

Day 1: Activin A (100 ng/ml) 0% FCS
Day 2-3: Activin A (100 ng/ml) 0.2% FCS

The cells were cultured 2 days without medium change. The protocol combines the medium supplements, Activin A and bFGF.

Stage II: DE-Hep Progenitor Expansion

For derivation and expansion of DE-Hep progenitors HCM medium (in some cases the HCM-antibiotic mix GA1000 was omitted) or a Williams E based medium or a comparable medium was used and supplemented with 1% PEST, 1% Glutamax and additionally with;

Day 6-9: FGF4, BMP2 (30 ng/ml, 20 ng/ml, respectively) 0% FCS.
Day 10-15: HGF (20 ng/ml) 0% FCS.

The DE-Hep progenitors were cultured in stage II medium from day 6 up to day 15 with medium change every 2-3 days.

Stage III: DE-Hep Maturation

For maturation of hepatic cells derived from definitive endoderm (DE-Hep cells) HCM medium (in some cases the HCM-antibiotic mix GA1000 was omitted) or a Williams E based medium or a comparable medium was used and supplemented with 1% PEST, 1% Glutamax and at day 16 additionally with: OSM, Dex, (10 ng/ml, $10^{-7}$ M), 0% FCS. The medium was change every 2-3 days. The DE-Hep cells were cultured in this medium for a minimum of 22 days and up to 35-40 days.

In some experiments EGF and ascorbic acid were omitted during the last days or the last week before analysing the DE-Hep cultures and a positive effect on maturation and functionality of the cells was observed. Without EGF and ascorbic acid proliferation is not stimulated anymore which leads to increased maturation instead.

One Specific Embodiment of the Invention, Protocol 4:

The following specific conditions were used in this specific embodiment, protocol 4, see FIG. 1b.

Stage I: DE Induction

Definitive endoderm was induced in stage I by cultivation in RPMI advanced medium or DMEM or a comparable medium supplemented with 1% PEST, 1% Glutamax and additionally with;

Day 1: Activin A (100 ng/ml) 0% FCS
Day 2-3: Activin A, FGF2 (100 ng/ml, 4 ng/ml, respectively) 0.2% FCS
Day 4-5: Activin A, FGF2 (100 ng/ml, 4 ng/ml, respectively) 1% FCS 50 or 100% of the medium was changed every day. The protocol combines the medium supplements, Activin A and bFGF.

Stage II: DE-Hep Progenitor Expansion

For derivation and expansion of DE-Hep progenitors RPMI advanced medium or DMEM or a comparable medium was used and supplemented with 1% PEST, 1% Glutamax and additionally with;

Day 6-7: BMP4, FGF2 (50 ng/ml, 4 ng/ml, respectively) 0.2% FCS.
Day 8-9: aFGF, FGF2 (50 ng/ml, 4 ng/ml, respectively) 1% FCS.
Day 10-12: HGF, FGF2, EGF (50 ng/ml, 2 ng/ml, 10 ng/ml, respectively) 1% FCS.

The DE-Hep progenitors were cultured in stage II medium from day 6 up to day 12 with 50 or 100% medium changes every 1-3 days.

Stage III: DE-Hep Maturation

For maturation of hepatic cells derived from definitive endoderm (DE-Hep cells) HCM medium (in some cases the HCM-antibiotic mix GA1000 was omitted) or a Williams E based medium or a comparable medium was used and supplemented with 1% PEST, 1% Glutamax and additionally with;

Day 13-14: OSM, ITS mixture, HGF (10 ng/ml, 1×, 50 ng/ml, respectively), 0% FCS
Day 15-26: OSM, ITS mixture, HGF, Dex (10 ng/ml, 1×, 50 ng/ml, $10^{-7}$ M, respectively), 0% FCS 50 or 100% medium was change every 1-3 days.

In some experiments EGF and ascorbic acid were omitted during the last days or the last week before analysing the DE-Hep cultures and a positive effect on maturation and functionality of the cells was observed. Without EGF and ascorbic acid proliferation is not stimulated anymore which leads to increased maturation instead.

Example 3

Morphology of Definitive Endoderm, Stage I

Activin A treatment was associated to morphological changes and distinct differentiation pattern of the colonies. After 3-5 days, treated by an Activin A-containing medium, cells gathered together and formed a ring of epithelial cells around the colony (FIG. 2). Those homogenous growing cells expanded over the plate and could be passaged to a Mouse feeder layer containing plate.

Example 4

Characterization of Definitive Endoderm with Immunocytochemistry and Quantitative Analysis At early differentiation stages Sox7 can be regarded as a marker for extraembryonic endoderm (ExE) and is not expressed in definitive endoderm (DE) (D'Amour et al., 2006). Sox17 positive cells are present both in ExE and DE. This suggests that Sox17+/Sox7− cells are of DE origin. Immunostainings with Sox7 and Sox17 were performed to confirm that DE-Hep cells have been generated from definitive endoderm. After 4 days with Activin A the vast majority of the cells are Sox17 positive and Sox7 negative (FIG. 3).

Activin A induces definitive endoderm detected by a combination of Sox17+/Sox7−, 80-90% of the total cells in a Activin A or Activin A/FGF2 treated culture are estimated to be Sox17 positive and negative for Sox7 (manual counting in microscope). Control cultures induced mainly extraembryonic endoderm that is Sox17/Sox7 positive.

Example 5

Gene Expression of Definitive Endoderm by Quantitative Real-Time PCR

To investigate the gene expression level in different cell types, TaqMan® low density arrays (384-Well Micro Fluidic Cards, Applied Biosystems) were used. For comparison, commercially available total RNA from foetal liver, human adult liver, plated human primary hepatocytes freshly isolated human primary hepatocytes and HepG2 was analyzed in parallel. cDNA synthesis was performed using Superscript 3 (cat no 18080-051 Invitrogen). The relative gene expression levels were normalized against the expression of CREBBP.

Q-PCR analysis of hBS cells induced for 5 days in medium supplemented with Activin A, showing expression levels of eight genes. Activin A induced a strong wave of early endoderm and is highlighted by high expression levels of Sox17, HNF3b and Cxcr4. Interestingly the combination of Activin A and bFGF yielded in higher expression of SOX17, HNF3b and CXCR4 compared to Activin A alone. Untreated hBS cells had significantly less SOX17, HNF3b and CXCR4 than growth factor treated cultures. In addition, the control culture (intrinsic differentiation) had significantly less SOX17, HNF3b and CXCR4 gene expression, in addition to an up regulation of early liver markers like AFP and A1AT. At this early stage of differentiation and development, this indicated the presence of extra embryonic endoderm in intrinsically differentiating colonies. CXCR4 is expressed in mesoderm and definitive but not in primitive endoderm [McGath K E. et al. Embryonic expression and function of the chemokine SDF-1 and its receptor, CXCR4. Dev. Biol. 213:442-45 (1999)] and are therefore in combination with Sox17 and/or HNF3b an excellent marker for DE. Sox17 and HNF3b are both markers for early definitive and primitive endoderm. The TGFbeta superfamiliy member Nodal is essential for specification of endoderm during gastrulation in mice. High levels of Nodal signaling specifies definitive endoderm and lower levels of Nodal signaling specifies mesoderm [Lowe, L A., Yamada, S., Kuehn, N. R., Genetic dissection of nodal function in patterning the mouse embryo. Development 128, 1831-1843 (2001); Brennan, J. et al. Nodal signaling in the epiblast patterns the early mouse embryo. Nature 411, 965-969 (2001)]. Activin is also a member of the TGFbeta family and binds to same receptor as Nodal (with the exception of the co-receptor cripto), triggering similar intracellular signaling events with LEFTY1 and LEFTY2 induction [de Caestecker, M. The transforming growth factor-beta superfamily of receptors. Cytocine Growth Factor Rev. 15, 1-11 (2004)], and therefore can be used to mimic Nodal activity in vitro. For gene expression data, see FIGS. 4 and 5.

Further proof that the combination of Activin A and bFGF generate higher expression of DE markers and lower expression of extra embryonic markers compared to Activin A alone was more extensive shown in several experiments by QPCR (SA002 p70 n=7, SA002 p29 n=5) (FIG. 6). Sox17, HNF3B/HNF3b and CXCR4 were all significant higher in Activin A and bFGF treated cultures compared to Activin A alone. The number of DE cells was higher in Activin A and bFGF treated cultures compared to Activin A alone (FIG. 6). Activin A treated cultures had higher expression of the extra embryonic markers AFP, A1AT and CDX2 compared to Activin A and bFGF treated cultures showing that Activin A in combination with bFGF generates more definitive endoderm compared to Activin alone. For gene expression data, see FIG. 6.

Example 6

Global Gene Expression: DE vs EE Induced Hepatocytes Several Probes for One Gene One probe represents a specific mRNA transcript (splicing variant) and these transcripts can show completely different expression profiles. As this is data on transcriptional level it will sometimes cause confusion when mapping to protein expression. To know which splicing variant that codes for the protein of interest in, different strategies can be used: 1) The variant with highest expression can be selected; 2) Average can be calculated; 3) A "biological" interpretation of the expected expression profile can be chosen. The third alternative has been used if the gene is well known. For less known genes the first strategy has been used. Each probe has a flag that indicates how specific the probe is. The probe names is included on left side in the plot. For genes that lack very specific probes we have shown the most specific available ones. Lower values than 1 is negative values in the log 2 scale, see table below.

| Log2 value | Normal value |
| --- | --- |
| −3 | 0.125 |
| −2 | 0.25 |
| −1 | 0.5 |
| 0 | 1 |
| 2 | 4 |
| 3 | 8 |
| 4 | 16 |
| 8 | 256 |
| 10 | 1024 |
| 13 | 8192 |
| 15 | 32768 |
| 20 | 1,048,576 |

GeneChip probe arrays are manufactured using technologies that combine photolithographic methods and solid phase chemistry. In this way arrays are produced containing hundreds of thousands of olignucleotide probes packed at extremely high densities. Currently, Affymetrix is providing GeneChips for monitoring global activities of genes in yeast, Arabidopsis, Drosophila, mice, rats and humans. To complement the global capabilities QPCR can be used as this method is even more sensitive. The relative gene expression levels were normalized against the expression of CREBBP. The following genes were analyzed to characterize undifferentiated cells: POU5 μl (Oct-4), NANOG, GDF3, GAL, LECT1, FOXH1, CER1, DNMT3B, DPPA5, FOXD3, TERT, TERF1, TDGF1///TDGF3, SOX2, PODXL, and LIN28. All of these genes were dramatically reduced in cultures exposed to Activin A and bFGF for 5 days. FIG. 7 shows the expression for OCT4 and Nanog but all the other markers had the same profile. Following genes were analyzed to characterize DE cells: LEFTY1, LEFTY2, BRA, AFP, SOX7, SOX17, SERPINA1 (A1AT), HNF4alfa, GOOSECOID, HNF3B, CXCR4, CDX2 of which some are plotted in FIG. 7. One could clearly se that LEFTY1, LEFTY2, GOOSECOID, SOX17, HNF3B, CXCR4 all were upregulated in cultures treated with Activin A and bFGF after 5 days. This was not as clear in control cultures (intrinsic differentiation, EE). See FIG. 7 The results from this experiment summarized in FIG. 7 The panel of genes are selected to distinguish between definitive and extraembryonic endoderm.

Description of Array Experiment and Data Analysis

Three cell lines SA167, SA002, and SA461 were used. The experimental set up was as follows: undifferentiated hBS cells (UD), definitive endoderm at day 5 (DE5), intrinsic differentiated hBS cells at day 5 (EE5), DE induced hepatic progenitors at day 10 (DE10), intrinsic differentiated hBS cells at day 10 (EE10), DE induced hepatocytes at day 20 (DE20), intrinsic differentiated hBS cells at day 20 (EE20). As controls fetal liver (FL), adult liver (AL), plated primary hepatocytes (PH) and fresh primary hepatocytes (FPH) and HepG2 were used.

The quality of the RNA and cDNA, labelled by in vitro transcription, was tested using an Agilent Bioanalyzer. Fragmented cDNA was hybridized at 45° C. for 16 hours to GeneChip Human, HGU 133 Plus 2.0 (Affymetrix, Santa Clara, Calif.). Each sample was hybridized to the arrays in biological duplicates (two arrays for each sample). For data extraction the MAS5 software (Affymetrix, Santa Clara, Calif.) was used and data was median normalized and log 2 transformed for subsequent data analysis.

All the plots are in log 2 scale.

The production of enriched cultures of hBS cell-derived DE in the presence of Activin A and bFGF were analyzed by multiple markers of good quality for analyzing of DE cells. We thereby show that we have made DE and not primitive endoderm from hBS cells. Our data also indicate that hBS cells cultured with Activin A together with bFGF give more DE cells comparison to cultures given just Activin A.

Example 7

Morphology of DE-Hep Progenitor Cells

The cultures strongly responded to exposure of the factors in stage II, (key component BMP4) and former homogenous epithelial cells grouped in small clusters. After two more days a rather heterogeneous population, among many epithelioid cell types was obtained. Moreover, in the second stage, after 6-9 days, the first polygonal-shaped cells with few bi-nucleated cells appeared (FIG. 8). These cells were often located next to three dimensional ridges of fibroblast-like cells (FIG. 8).

Example 8

Characterization of DE-Hep Progenitor Cells with Immunocytochemistry

The DE-Hep progenitor population was confirmed by immunofluorescence markers, see table 2 summarizing the analysis by immunocytochemical labelings of early DE-Hep progenitor cells from stage II also depicted in FIG. 8 and example 7. DE-Hep progenitor cells are often found in regions with cells expressing EpCAM, FIG. 9.

TABLE 2

Immunocytochemical analysis on DE-Hep progenitors (stage II).

| Antibody | DE-Hep progenitor cells (stage II) |
|---|---|
| EpCAM | + (subpop.) |
| HNF4a | + |
| HNF3b | + |
| HNF1 | + |
| CK8 | + |
| CK18 | + |
| CK19 | + |
| Desmin | + (subpop.) |
| ICAM-1 (CD54) | + (subpop.) |
| c-kit | + (subpop.) |
| CD133 | + (subpop.) |

Example 9

Gene Expression of DE-Hep Progenitors

The RNA concentration of the samples was determined using NanoDrop ND-1100. The same amount of RNA from the different samples was used in reverse transcription which was performed in duplicates to create cDNA. As a control for the amount of genomic DNA the NoRT control was performed where no reverse transcriptase (RT) enzyme was added. The signal in the NoRT control reflects the amount of genomic DNA. qPCR of the genes was performed on the cDNA from the duplicate samples and on the NoRT control. The assays used are: HNF3b, HNF4a, EpCAM, AFP, AAT, Desmin, CD133, Notch2, ICAM-1, CK7, CK18 and CK19.

Analysis: Relative quantities are calculated assuming a 90% PCR efficiency and setting the sample with lowest expression level to a value of 1. Other samples can then be directly compared and plotted.

Example 10

Expansion and Culture of DE-Hep Progenitors

For expansion and purification of DE-Hep progenitors, the cultures were enzymatically treated at stage II day 5 (protocol 1 and 4) with 0.2% Trypsin-EDTA or manually dissected and transferred to Matrigel coated tissue culture plates for replating according to the scheme described below. For Matrigel culture of DE-Hep progenitors RPMI Advanced medium or DMEM or a comparable medium was used and supplemented with 1% PEST, 1% Glutamax and additionally with;

Day 5: aFGF, bFGF, BMP2, BMP4 (100 ng/ml, 5 ng/ml, 50 ng/ml, 200 ng/ml, respectively) 5% FCS;
Day 6: aFGF, bFGF, BMP2, BMP4 (100 ng/ml, 5 ng/ml, 50 ng/ml, 200 ng/ml, respectively) 0.2% FCS;
Day 7: bFGF, BMP4, HGF (50 ng/ml, 200 ng/ml, 50 ng/ml, respectively) 0.2% FCS;
Day 8: bFGF, BMP4, HGF (50 ng/ml, 200 ng/ml, 50 ng/ml, respectively) 0.2% FCS;
Day 9: bFGF, BMP4, HGF (50 ng/ml, 200 ng/ml, 50 ng/ml, respectively) 0.2% FCS;

Further maturation into DE-Hep cells was carried out as in example 2. DE-Hep progenitor cells could also be dissociated by Collagenase IV and replated on a MEF coated plate.

Example 11

Morphology of DE-Hep Cells in Stage III of the Novel Protocol 1

In phase III, the cultures were changed to HCM medium (see FIG. 1a and example 2). At this stage many DE-Hep cells emerged and exhibited typical hepatocyte morphology with a polygonal shape, containing distinctive nuclei with nucleoli (FIG. 11). Interestingly they were arranged in small islet-like clusters that were surrounded by fibroblast-like cells (FIG. 12). This morphology differs from the morphology of the hepatocyte-like cells derived by intrinsic differentiation (FIG. 12; compare also Söderdahl et al., 2007).

Example 12

Characterization of DE-Hep Cells with Immunocytochemistry and Quantitative Analysis Whole colonies were fixated and analyzed by immunocytochemistry. The data in table 1 showed that in the DE-Hep cultures many cells were positive for CYP1A2, CYP3A4/7, CK18, CK8, CK19 and HNF4alpha. Interestingly the expression of the polarized transporter protein MRP2 could be detected in the DE-Hep cultures but not in the untreated control cultures (intrinsic differentiation). Table 3A summarizes the immunocytochemical analysis that has been performed up to now on DE-Hep cells at stage II, control cultures, HepG2 and primary human hepatocytes, commercially available from In Vitro Technologies. Empty boxes have not been stained or analyzed.

TABLE 3A

Immunocytochemical analysis on DE-Hep cells at stage III in comparison to control cultures (intrinsically differentiated hBS cultures), HepG2 and primary human hepatocytes. DE-Hep cultures characterized in phase III by immunohistochemistry and ELISA. A good specific marker for hepatocytes is the synthesis of urea which is made only by the hepatocytes and not by the yolk sac and could thus be used to discriminate between true hepatocytes and yolk sac cells.

|  | DE-Hep | Control | HepG2 | Human primary hep |
|---|---|---|---|---|
| ICC |  |  |  |  |
| α$_1$-antitrypsin | + | + | + | + |
| αFP | + | + | + | − |
| Albumin | + | + | + | + |
| CK 7 | + | + | − | − |
| CK8 | + | + | + | + |
| CK18 | + | + | − | + |
| CK19 | + | + | + | − |
| CYP1A2 | + | − | − | + |
| CYP3A4 | + | − | − | + |
| Glycogen | + | + | + only few | + only few |
| HNF3β | + | + | + | + |
| ICG | + | + |  | + about 15% |
| LFABP | + | + | − | + |
| MRP2 | + | − | − | − |
| ELISA |  |  |  |  |
| Urea (mmol/L) | 1.2 | <0.8 | 1.5 | 1.7 |

* intrinsically differentiated hBS cultures

The table covers the characterization data of phase III DE-Hep cultures, that were compared to cultures of intrinsically differentiated hBS cells, the HepG2 cell line, and human primary hepatocyte cultures. The "+" and "−" are semi quantitative measures and describe the approximate levels of the analyzed marker

TABLE 3B

Calculation of human Albumin positive nuclei in DE-Hep cultures

| Protocol | Number Human nuclei | Number Human Albumin positive nuclei | % Human Albumin positive nuclei |
|---|---|---|---|
| DE-Hep cells, Protocol 2 | 39655 | 9821 | 24.8 |

*Since a certain percentage of DE-Hep cells are found to be bi-nucleated (like human hepatocytes), the number of nuclei is not equal with the number of cells.

Example 13

Biological Activity of DE-Hep Cells

In order to assess whether these DE-Hep cells are functional, they were tested for Indocyanine green uptake and secretion (Example 17), glycogen storage (Example 18), Albumin secretion (Example 15), LDL-uptake, metabolic capability of distinct drugs (Example 16) and ammonia metabolism (Example 20).

We found DE-Hep cultures to be capable of uptake and excretion of indocyanine green (see Example 17).

Since human hepatocytes can store and make glycogen, we analyzed glycogen levels by periodic acid-Schiff staining of stage III cells and untreated cultures. Positive staining was found in both cultures (see Example 18 and FIG. 15).

To further determine the differentiation state and functional competence of the DE-Hep cells, the cells were evaluated for albumin gene expression and Albumin secretion (see Example 15).

To determine whether the DE-Hep cells of stage III would take up LDL, which is observed in hepatocytes, we assessed LDL uptake by incubating the cultures with DiI-Ac-LDL (1,1gamma-dioctadecyl-3,3,3delta,3gamma-tetramethylindocarbocyanine perchlorate ($C_{59}H_{97}ClN_2O_4$) acetylated Human Low Density Lipoprotein). Cultures in stage III toke up LDL whereas in untreated control cultures only some cells showed LDL uptake.

For drug metabolism of Phenacetin, Diclofenac and Midazolam through DE-Hep cells see Example 16 and for ammonia metabolism see Example 20.

Example 14

Gene Expression Analysis of DE-Hep Cells by Q-PCR and LDA Cards

Samples of hBS cell derived DE-Hep cultures and adequate controls (either intrinsically differentiated hBS cells on MEFs with sparse VitroHES™ medium change or HepG2 cells) were analysed by QPCR for the expression of hepatic-related genes. Expression of albumin, HNF4a, CYP3A4, CYP3A7, CYP7A1 and UGT2B7 was analyzed as specified in Table 4.

In addition, gene expression of DE-Hep cells was characterised on LDA microfluidity cards as listed in Table 5 A and B. cDNA derived from total RNA of the samples was hybridised with a LDA card and the experiment ran in a PCR setup and further analysed using suitable software. All samples were run in parallel with adequate controls in repeated experiments on the LDA card following the instructor's manual (Applied Biosystems 7900HT Micro Fluidic Card Getting Started Guide) and the following shortened protocol:

cDNA was prepared from total RNA and diluted it in RNase/DNase-free water to receive a suitable concentration (see below). The following components were mixed: cDNA (1-100 ng), 5 µl, RNase/DNase-free water, TaqMan Universal PCR, 45 µl, Master mix (2×), 50 µl, Total: 100 µl. The samples were thereafter loaded onto the LDA card (each sample mix is 100 ul and 170 ng cDNA per sample) and centrifuged, whereafter the LDA card was sealed. Finally, the card was run on ABI 7900HT real-time PCR system according to the instructions in the manual and the results analyzed by using SDS 2.2.1 software and the relative quantification method.

A summary of gene expression analysis on DE-Hep cells by either QPCR or LDA analysis is presented in Table 4 (QPCR) and 5 (LDA) and described in the following.

TABLE 4

Gene expression analysis by QPCR.

| | Sample description | HNF4a | Alb | CYP3A4 | UGT2B7 | CYP3A7 | CYP7A1 |
|---|---|---|---|---|---|---|---|
| | Protocol 1 (without any modifications) | | | | | | |
| A | DE-Hep, SA348 | 2 | 68 | 52 | 4 | — | — |
| | intrinsically differentiated hBS cells, SA348 | 1 | 1 | 1 | 1 | — | — |
| | Protocol 2 (without any modifications) | | | | | | |
| B | DE-Hep, SA348 | 5 | 143 | 71 | 89 | 114 | 2 |
| | intrinsically differentiated hBS cells, SA348 | 1 | 1 | 1 | 1 | 1 | 1 |
| | Protocol 3 (without any modifications) | | | | | | |
| C | DE-Hep, SA348 | 0.4 | 8 | 234 | 3 | 237 | 2 |
| | intrinsically differentiated hBS cells, SA348 | 1 | 1 | 1 | 1 | 1 | 1 |
| D | DE-Hep, SA348 | — | 5 | 80 | 3 | 118 | 3 |
| | intrinsically differentiated hBS cells, SA348 | — | 1 | 1 | 1 | 1 | 1 |
| | Protocol 4 (without any modifications) | | | | | | |
| E | DE-Hep, SA348 | — | 139 | 160 | 44 | 253 | 3 |
| | intrinsically differentiated hBS cells, SA348 | — | 1 | 1 | 1 | 1 | 1 |
| F | DE-Hep, SA348 | — | 18 | 22 | 3 | 33 | 24 |
| | intrinsically differentiated hBS cells, SA348 | — | 1 | 1 | 1 | 1 | 1 |
| | Protocol from Cai et al. 2007 (without any modifications) | | | | | | |
| G | DE-Hep, SA348 | 0 | 0.1 | 154 | 0 | 278 | 4 |
| | intrinsically differentiated hBS cells, SA348 | 1 | 1 | 1 | 1 | 1 | 1 |

Sample C performed with EGF and ascorbic acid

Sample D performed without EGF and ascorbic acid

Sample E modifications: stage 1: without Activin A, bFGF and FCS; stage 2: DMEM instead of RPMI A and 0.2% FCS all the time; stage 3: no ITS and HGF on days 17-30.

Sample F: without EGF and ascorbic acid.

— = not tested;

0 = no expression detected.

* Expression in DE-Hep cells (DE-Hep) is normalized to expression in intrinsically differentiated control hBS cells.

* DE-Hep cells and intrinsically differentiated control hBS cells were analysed after 21-38 days in culture.

DE-Hep cells derived with protocols 1-4 show increased expression of adult liver-related genes compared to intrinsically differentiated control hBS cells. Importantly, expression of functional genes like CYP3A4 is often found to be clearly higher in DE-Hep cells. Expression of adult liver-related genes like CYP7A1 is detected in all tested samples and often higher in DE-Hep cultures than in intrinsically differentiated control hBS cells. In many samples CYP1A2 expression was detected (data not shown).

When comparing our protocols 1-4 with the protocol published by Cai et. al. 2007 (G) both HNF4a, Albumin and UGT2B7 are clearly higher.

Table 5: Gene Expression Analysis of DE-Hep Cells on LDA Cards

TABLE 5A

|  | Genes | DE-Hep Prot. 1 SA002 | intrinsically differentiated hBS cells SA002 |
|---|---|---|---|
| Cytochrome P450s | CYP1B1 | 83 | 1 |
|  | CYP2A6/2A7/2A13 | 1.5 | 1 |
|  | CYP2B6 | 0.25 | 1 |
|  | CYP2C8 | 150 | 1 |
|  | CYP2C9 | 400 | 1 |
|  | CYP2C19 | 0.3 | 0 |
|  | CYP2D6 | 4 | 1 |
|  | CYP2E1 | 62.5 | 1 |
|  | CYP3A4 | 0.03 | 0 |
|  | CYP3A5 | 0.07 | 0 |
| UGTs | UGT1A3 | 0 | 0 |
|  | UGT1A6 | 0.2 | 0 |
|  | UGT1A8 | 0 | dCT = 11 |
|  | UGT2B7 | 1.5 | 0 |
|  | UGT1A | 100 | 1 |
| Transporters | NTCP | 2.2 | 0 |
|  | OATP-A | 2.41 | 1 |
|  | OATP-2 | 1.1 | 1 |
|  | OCT1 | 5 | 1 |
|  | MDR1 | 6.6 | 1 |
|  | MDR3 | dCT = 6.5 | dCT = 8.7 |
|  | BSEP | 1.6 | 0 |
|  | MRP2 | 300 | 0.001 |
| Transcription factors | FXR | 0.005 | 0 |
|  | RXRα | 8 | 1 |
|  | RXRβ | 9 | 1 |
|  | RXRγ | 10 | 1 |
|  | HNF1α | 0.3 | 0 |
|  | HNF3α | 30 | 1 |
|  | HNF3β | 1.3 | 1 |
|  | HNF4α | 20 | 1 |
|  | HNF6 | 37.5 | 1 |
|  | DBP | 3.6 | 1 |
|  | C/EBP A | 20 | 1 |
|  | C/EBP B | 11 | 1 |
| Others | Albumin | 1880 | 1 |
|  | Apolipoprotein E | 10 | 1 |
|  | Alcoholdehydrogenase 1 (ADH1A) | 3.6 | 0 |

*Normalized against HPRT1. *Intrinsically differentiated hBS cells are control sample.; dCT values were given in cases the control samples did not express the tested gene. Protocol 1 performed without any modifications.

In Table 5A, DE-Hep cells at stage III derived by protocol 1 from hESC line SA002 are compared to intrinsically differentiated hBS cells from hESC line SA002 (set as one). DE-Hep cells show increased expression of almost all genes compared to intrinsically differentiated hBS cells.

TABLE 5B

|  | Genes | DE-Hep Prot. 1 SA002.5 | DE-Hep Prot. 2 SA348 | DE-Hep Cai 07 SA348 | hum. prim. hepatocytes | HepG2 |
|---|---|---|---|---|---|---|
| Cytochrome P450s | CYP1B1 | + | + | + | + | 0 |
|  | CYP2A6/2A7/2A13 | 351 | 96 |  | 740 | 1 |
|  | CYP2B6 | 9.1 | 37.3 |  | 228 | 1 |
|  | CYP2C8 | 9.6 | 6 |  | 0.5 | 1 |
|  | CYP2C9 | + | + | 0 | + | 0 |
|  | CYP2C19 | + | + |  | + | 0 |
|  | CYP2D6 | 0.7 | 0.03 | 0 | 0.6 | 1 |
|  | CYP2E1 | 6 | 8.7 |  | 656.2 | 1 |
|  | CYP3A4 | 25.6 | 187.6 |  | 262.8 | 1 |
|  | CYP3A7 | 158.4 | 680.6 |  | 6.5 | 1 |
| UGTs | UGT1A6/4/3 | 0.007 | 0.02 |  | 217.2 | 1 |
|  | UGT1A6 | + | + | 0 | + | 0 |
|  | UGT1A8 | 0 | 0 | 0 | 0 | 0 |
|  | UGT2B7 | 0.6 | 0.7 |  | 1.9 | 1 |
|  | UGT1A | 0.09 | 0.5 | 0 | 201.6 | 1 |
| Transporters | NTCP | + | + |  | 0 | 0 |
|  | OATP-A | + | + |  | 0 | 0 |
|  | OATP-2 | + | + | 0 | + | 0 |
|  | OCT1 | 1.6 | 4.1 |  | 36.8 | 1 |
|  | MDR1 | 0.009 | 0.008 |  | 1.3 | 1 |
|  | MDR3 | 0.03 | 0 | 0 | 1.8 | 1 |
|  | BSEP | + | 0 |  | + | 0 |
|  | MRP2 | 0.02 | 0.03 |  | 0.6 | 1 |
| Transcription factors | FXR | 0.009 | 0.02 |  | 8.5 | 1 |
|  | RXRα | 0.4 | 1.4 |  | 4.6 | 1 |
|  | RXRβ | 0.8 | 1.9 |  | 1.9 | 0 |
|  | RXRγ | + | + | 0 | 0 | 0 |
|  | HNF1α | 0.04 | 0.2 |  | 2 | 1 |
|  | HNF3α | 0.4 | 0.7 |  | 3.5 | 1 |
|  | HNF3β | 0.1 | 0.5 |  | 2.3 | 1 |
|  | HNF4α | 0.03 | 0.1 |  | 0.7 | 1 |
|  | HNF6 | 0.6 | 0.2 |  | 5 | 1 |

TABLE 5B-continued

| | Genes | DE-Hep Prot. 1 SA002.5 | DE-Hep Prot. 2 SA348 | DE-Hep Cai 07 SA348 | hum. prim. hepatocytes | HepG2 |
|---|---|---|---|---|---|---|
| Others | C/EBP A | 0.2 | 0.2 | | 1.2 | 1 |
| | C/EBP B | 0.4 | 0.8 | | 9.7 | 1 |
| | Apolipoprotein E | 1 | 1.6 | | 3.1 | 1 |
| | Alpha 1 antitrypsin | 0.1 | 0.3 | | 18.6 | 1 |
| | Alcoholdehydrogenase 1 (ADH1A) | + | + | 0 | + | 1 |
| | Cytochrome P reductase | 0.3 | 0.4 | | 2.4 | 1 |

*Normalized against HPRT1.
*HepG2 cells and human primary hepatocytes cultured for 48 hr are control samples. HepG2 is set as 1 and all other samples are normalised to their expression.
; + = expression detected, but not normalised since HepG2 cells were negative
"Cai 07" = protocol according to Cai et al. 2007 (see references)
No modifications performed in protocols 1 and 2 compared and Cai et al. 2007

In Table 5B, DE-Hep cells at stage III derived by protocol 1 from hESC line SA002.5, by protocol 2 from hESC line SA348, and by the protocol from Cai et al. 2007 from hESC line SA348 are compared to primary human hepatocytes cultured for 24 hr and HepG2 cells (set as one).

Interestingly, UGT2B7, CAR, HNF4a and Albumin are found to be expressed at higher levels in DE-Hep cells derived by protocol 1 and 2 compared to DE-Hep cells derived with the Cai-protocol. No expression of CYP2C9, CYP2C19, CYP2D6, UGT1A6, OATP-2 and Alcohol dehydrogenase 1 could be detected in DE-Hep cells derived with the Cai-protocol.

Comparison of Gene Expression in DE-Hep Cells with Human Primary Hepatocytes and HepG2 Cells (see FIG. 18)

DE-Hep cells derived with protocol 2 (3 independent experiments) show equally high CYP3A4 expression as human primary hepatocytes cultured for 48 hr and about 100 times higher expression than HepG2 cells. Hepatocyte-like cells in intrinsically differentiated hBS cells cultures (3 independent experiments, run in parallel to protocol 2) show lower expression levels of CYP3A4 compared to DE-Hep cultures. DE-Hep cells derived with protocol 2 are found to express the adult liver-related genes CYP7A1 and glucose 6 phosphatase (see Table 5A and B). Note that DE-Hep cultures are not a homogenous cell population and that the expression level would be higher if one enriched DE-Hep cells from the mixed cultures.

Example 15

Elisa Analysis of Albumin Secretion in Medium Supernatants from DE-Hep Cells

Albumin secretion was analyzed using Albumin Quantification kit (cat. No. 03576108, Cobas) at Klinisk Kemi, C-lab, Sahlgrenska University Hospital, Gothenburg. Albumin is synthesized in liver parenchymal cells at a rate of 14 g/day and has two main functions in plasma: maintaining the oncotic pressure (80% due to albumin in plasma) and transport. It is the most important transport protein for substances having low water solubility (such as free fatty acids, bilirubin, metal ions, hormones and pharmaceuticals). The test principle is based on an immunoturbidimetric assay, using anti-albumin antibodies. These antibodies react with the antigen in the sample to form antigen/antibody complexes which, following agglutination, are measured turbidimetrically. Expected values in serum/plasma are 35-52 g/L (532-790 µmol/L).

The cells were analyzed at different stages, stage II medium samples A-E. In the first differentiation phase (Stage I, see FIG. 1a) Activin A induces hBS cells into DE which takes 1 to 5 days. In stage II early liver cell types are induced by BMP4 or/and other factors and this early liver cells expanded and mature. In the last phase, stage III, terminal maturation is achieved by HGF, OSM, DEX for up to several days (FIG. 1a). Definitive endoderm induced DE-Hep cells secreted Albumin. Albumin was not detected in controls of intrinsically differentiated hBS cells according to Soderdahl et al. 2007, Table 6. Neither the human primary hepatocytes nor the HepG2 cells secreted albumin above the detection level of this assay. Notice that samples A-D have been incubated in its medium for two days whereas sample E was incubated in its medium for one day, table 6.

TABLE 6

Albumin secretion from DE-Hep cells (SA002).

| Samples | Albumin (mg/l) |
|---|---|
| 1a DE-Hep cells, day 22 | 149 |
| 1b intrinsically differentiated hBS cells, day 22 | — |
| 2a DE-Hep, cells day 24 | 152 |
| 2b intrinsically differentiated hBS cells, day 24 | — |
| 3a DE-Hep cells, day 20 | 142 |
| 3b intrinsically differentiated hBS cells, day 20 | — |
| 4a DE-Hep cells, day 38 | 142 |
| 4b intrinsically differentiated hBS cells, day 34 | — |
| 5 DE-Hep cells, day 31 | 75 |
| 6 HepG2 | — |
| 7 Human primary Hepatocytes | — |

Example 16

DE-Hep Cells Display Functional Drug Metabolism via CYP1A2, CYP3A4 and CYP2C9

HBS derived DE-Hep cells at stage III were tested for their ability to metabolize 3 probe drugs for the phase I enzymes CYP1A2, CYP2C9 and CYP3A4. 26 µM Phenacetin (metabolised by CYP1A2; purchased from Aldrich), 9 µM Diclofenac (metabolised by CYP2C9; purchased from SIGMA) and 3 µM Midazolam (metabolised by CYP3A4; purchased from SIGMA) were incubated as a cocktail for 12-17 hr at 37° C. and 5% $CO_2$ in phenol red free medium.

Samples of the culture supernatants were collected and centrifuged for 5-20 min at a speed of 500-4000 g to get rid of any cell debris. 100-120 µl of the cleared supernatant samples was transferred to a 96-well plate and 15 µl of acetonitril was added to each well. Addition acetonitril could be omitted if desired. The samples were frozen at −20 C, and the metabolite concentrations in the culture supernatant were measured by LC-MS (acetaminophen for CYP1A2, 1 hydroxyl-Midazolam (10H-Midazolam) for CYP3A4 and hydroxyl-Diclofenac (OH-Diclofenac) for CYP2C9).

DE-Hep cells metabolized all three probe drugs tested (Table 7 and FIG. 14 A). Interestingly, DE-Hep cultures derived from different hBS cell lines differ in metabolic activity for CYP1A2, 3A4 and CYP2C9 resulting in typical CYP activity profiles for different hBS lines, e.g. high CYP1A2 and lower CYP3A4 activity in DE-Hep cells derived from hBS cell lines SA001, SA002 and SA002.5 and vice versa in hBS cell line SA348 (FIG. 14 A). This is in agreement with the well-known inter-individual variation of CYP expression in human described in literature and reproduced in our hands when analyzing CYP activity in human primary hepatocytes isolated from different donors (FIG. 14 B).

In addition to the constitutive CYP expression in untreated DE-Hep cultures (FIG. 14 A), CYP expression in DE-Hep cells is inducible by treatment with a CYP inducer cocktail containing 25 µM Rifampicin, 25 µM Omeprazole, 100 µM Isoniazid, 100 µM Dexamethasone, 10 µM Primidone (Desoxyphenobarbital), and 88 mM Ethanol: CYP1A2 activity and CYP1A2 and CYP3A4 mRNA levels are 3-4 fold higher (FIG. 4 C,D) after a 24 hr incubation with the CYP inducer cocktail than in untreated control cultures.

In contrast to DE-Hep cells, the hepatoma cell line HepG2 shows mainly CYP1A2 activity, whereas only low CYP3A4 activity and no CYP2C9 activity could be detected (Table 7 and FIG. 14 B). However, when comparing CYP activity in DE-Hep cultures with HepG2 and human primary hepatocytes, it should be taken into account that both HepG2 and human primary hepatocytes are a pure cell population whereas DE-Hep cultures are a mixed cell population and contain other cell types besides DE-Hep cells. Taken together, DE-Hep cells display both constitutive and inducible CYP expression, large inter-individual variations in CYP expression levels between different hBS cell lines and thus a high similarity to human primary hepatocytes.

TABLE 7

Cytochrome P450 activity of DE-Hep cells

| Protocol | Cell line | Days in culture | nM Phenacetin (=CYP1A2) | nM OH-Midazolam (=CYP3A4) |
|---|---|---|---|---|
| Protocol 1 (ECD) | SA001 | 27 | 53 | 0 |
| Protocol 1 (induced, ECD) | SA001 | 27 | 58 | 0 |
| Protocol 1 | SA002 | 26 | 886 | 1 |
| Protocol 1 | SA002.5 | 31 | 133 | 2 |
| Protocol 1 | SA167 | 30 | 149 | 3 |
| Protocol 2 | SA001 | 27 | 273 | 2 |
| Protocol 2 (ECD) | SA001 | 27 | 59 | 0 |
| Protocol 2 (ECD, induced) | SA001 | 27 | 195 | 0 |
| Protocol 2 | SA002 | 28 | 137 | 4 |
| Protocol 2 (ECD) | SA002 | 37 | 225 | 4 |
| Protocol 2 (+10% FCS in stage 2 and 3) | SA167 | 30 | 6 | 12 |
| Protocol 3 (ECD) | SA001 | 27 | 37 | 2 |
| Protocol 3 | SA002 | 29 | 38 | 4 |
| Protocol 3 | SA002.5 | 29 | 138 | 12 |
| Protocol 3 | SA348 | 29 | 0 | 127 |

TABLE 7-continued

Cytochrome P450 activity of DE-Hep cells

| Control cell types | nM Phenacetin (=CYP1A2) | nM OH-Midazolam (=CYP3A4) |
|---|---|---|
| HepG2 cells* | 427 | 5 |
| Primary human hepatocytes (from 4 different donors), cultured for 48 hr* | 4026 | 464 |
| Mouse embryonic feeder cells | 5 | 1 |

"ECD" = Enzymatic cluster dissociation.
*for both HepG2 cells and human primary hepatocytes, the average of 4 independent experiments was calculated. Human primary hepatocytes were cultured for 48 hr before adding drugs.

Mouse embryonic feeder cells display very low CYP activity levels close to the detection level, thus not significantly contributing to CYP activity measured in DE-Hep cultures on mouse embryonic feeder cells.

Example 16

Transporter Analysis of DE-Hep Cells, Stage III

Transport across hepatocyte plasma membranes is a key parameter in hepatic clearance and usually occurs through different carrier-mediated systems.

Multidrug Resistance Protein 2 (MRP2)

Biliary elimination of anionic compounds is mediated by the multidrug resistance protein 2 (MRP2). MRP2 immunofluorescence is found in DE-Hep cell cultures at stage III (see FIGS. 14 a and b). Expression of MRP2 in DE-Hep cells was confirmed on the mRNA level on the LDA cards (see Table 5A+B).

Indocyanine Green (ICG)

Indocyanine green (ICG, also called Cardiogreen, Sigma, I2633) is an organic anion that is nontoxic and eliminated exclusively by hepatocytes and is therefore commonly used clinically as a test substance to evaluate liver function. (Shinohara et al. 1996). ICG was dissolved in 5 ml of solvent in a sterile vial and then added to 20 ml of DMEM containing 10% FBS. The final concentration of the resulting indocyanine green (ICG) solution was 1 mg/ml. The ICG solution was added to the cell culture dish and incubated at 37° C. for 60 minutes. After the dish was rinsed three times with phosphate-buffered saline (PBS), the cellular uptake of ICG was examined with a stereomicroscope. After the examination, the dish was refilled with DMEM containing 10% FBS. ICG was eliminated from the cells over night.

The uptake of indocyanine green by functional DE-Hep cells was analysed and showed indeed that after nearly 60 min of incubation with ICG many cells of the DE-Hep cultures were positive showing the ability to actively take up ICG (see FIG. 14 c). Furthermore after 24 h most of the ICG had been excreted from the cells. ICG uptake and excretion appeared only in few of the control cultures, showing that intrinsically differentiating cultures are able to generate also functional hepatocyte-like cells.

Uptake and excretion of ICG is known to occur via the drug transporter OATP-2 which expression in DE-Hep cells was confirmed on the mRNA level on the LDA cards (see Table 5A+B).

Example 17

Glycogen Storage of Functional DE-Hep Cells

Human hepatocytes synthesise and store glycogen. We analyzed glycogen levels by periodic acid-Schiff staining of DE-Hep cells in stage III and in intrinsically differentiated cells. Positive staining was found in both cultures (glycogen staining of DE-Hep cells: FIG. 15; glycogen staining of intrinsically differentiated cells: see Söderdahl et al. 2007). Significantly higher glycogen storage was found in the DE-Hep cells than in intrinsically differentiated cells and could be related to cells with a hepatocyte-like morphology. Note that some glycogen-positive cells in FIG. 15 B are bi-nucleated.

Glycogen storage detection in cells was detected by PAS-staining (Periodic Acid-Schiff staining system, SIGMA-ALDRICH, Cat-no. 395-B). The cells were fixed in 4% paraformaldehyde diluted in methanol for 15 minutes at room temperature and subsequently washed three times in PBS. As technical negative control, a culture was treated with human saliva for 20 minutes at room temperature and subsequently washed in PBS. The human saliva contains α-amylase which digests glycogen. Periodic acid, which oxidizes glycols to aldehydes, was added to the treated and untreated cultures for 5 minutes at room temperature followed by repeatedly washing in PBS. Subsequently, cultures were incubated in Schiff's reagent for 15 minutes at room temperature allowing a reaction between pararosaniline and sodium metabisulfite which results in a pararosaniline product that stains the glycol-containing cellular compartments bright pink. After washing in PBS cells were counter-stained in haematoxylin for 90 seconds at room temperature and rinsed in $H_2O$ prior to mounting in mounting media. Haematoxylin stains the nuclei of a cell (blue).

Example 18

Immunocytochemical Detection of Definitive Endoderm-, Hepatic Progenitor- and Liver-Related Genes, as Well as Drug Metabolizing Enzymes and Drug Transporters
Used Primary Antibodies:
Albumin (rabbit) 1:500, DAKOCytomation, A0001
AAT (rabbit) 1:200, DAKOCytomation, A0012
CD133 (mouse) 1:50, Miltenyi, clone AC141 c-kit (goat) 1:100, R&D, AF332
CK7 (rabbit) 1:200, Novocastra, NCL-CK7 560
CK8 (mouse IgG1) 1:200, Santa Cruz, sc-52324
CK18 (mouse) 1:200, DAKOCytomation, M7010
CK19 (mouse IgG1) 1:150, Novo Castra, NCL-CK19
Desmin (mouse IgG1) 1:200, Chemicon, MAB 1698
EpCAM (mouse IgG1), 1:50, GeneTex, Inc. VU-ID9
EGFR-1 (mouse IgG2b), 1:100, abcam, ab30 e-cadherin (mouse IgG1), 1:500, ZYMED, 13-1700
LFABP (goat) 1:500, Santa Cruz, sc-16064
HNF3b (goat) 1:250, Santa Cruz, sc-6554
HNF4a (rabbit) 1:500, Santa Cruz, sc-8987
HNF1a (rabbit), 1:400, Santa Cruz, sc-22840
Nestin (mouse IgG1), 1:250, BD Biosciences, 611658
Notch2 (rabbit) 1:100, SantaCruz, 25-255
Oct-4 (mouse) 1:500, Santa Cruz, sc-5279 c-Met (HGF receptor, mouse) 1:100, upstate, 05-237 α6-integrin (CD49f, rat) 1:250, BD Biosciences, 555736
ICAM-1 (CD54, mouse) 1:500, BD Pharmingen, 559047
PDGFRa (mouse) 1:500, Chemicon, CBL1366
Sox17 (rabbit) 1:2000, (kind gift from E. Baetge)
Vimentin (mouse IgG1) 1:300, SIGMA, V-6630
Used Secondary Antibodies:
    donkey anti-goat-Alexa 488, 1:500, Molecular Probes, # A-11055
    donkey anti mouse-Cy3, 1:1000, Jackson Immuno Research, #715-165-151
    donkey anti-mouse-Cy2, 1:100, Jackson Immuno Research, #715-225-151
    donkey anti-rabbit-Alexa488, 1:1000, Molecular Probes, #A-21206
    donkey anti-rabbit-Alexa594, 1:1000, Molecular Probes, #A-21207
    donkey anti-rat-Cy3, 1:500, Jackson Immuno Research, #712-165-153
    donkey anti-rat-Cy2, 1:100, Jackson Immuno Research, #712-225-153
Immunostaining Protocol:
For Intracellular Proteins:
    15 min fixation in 4% PFA, 2×PBS wash, 30 min 5% FBS in 0.1% PBT, primary antibodies incubated in 1% FBS in PBS overnight at 4 C, secondary antibodies in 1% FBS in PBS for 1 hr at RT, all washes in PBS, DAPI at 0.05 mg/ml for 5 min at RT, mounted in DAKOCytomation mounting medium.
For Extracellular Proteins:
    15 min fixation in 4% PFA, 2×PBS wash, 30 min 5% FBS in PBS, primary antibodies incubated in 1% FBS in PBS overnight at 4 C, secondary antibodies in 1% FBS in PBS for 1 hr at RT, all washes in PBS, DAPI at 0.05 mg/ml for 5 min at RT, mounted in DAKOCytomation mounting medium.
Phase I Metabolic Enzymes:
    Drugs are metabolised or broken down by two sequential pathways in human/mammals. Phase I enzymes consist of the Cytochrome P450 family. Proteins from this class of enzymes catalyse reactions resulting in the addition of functional groups and reactive centres as for example SH, OH, —NH2 and —COOH groups to their xenobiotic substrates. DE-Hep cells display immunoreactivity for the following CYPs: 1A2, 3A4/7 (potential antibody cross reaction between the two subtypes).
Used Primary Antibodies:
    CYP1A2 (rabbit) 1:100, Biomol, CR3130; raised to a synthetic tridecapeptide of human CYP1A2 and therefore presumably not cross-reacting with CYP1A1
    CYP1A2 (rabbit) 1:200, Cypex, PAP021; not cross-reacting with CYP1A1 in Western Blot according to information by the manufacturer
    CYP3A4 (sheep) 1:100, Biomol, CR3345; presumably cross-reacting with CYP3A7 according to information by the manufacturer
    CYP3A4 (rabbit) 1:200, Cypex, PAP011; presumably cross-reacting with CYP3A7
Used Secondary Antibodies:
    donkey anti-rabbit-Alexa488, 1:1000, Molecular Probes, #A-21206
    donkey anti-sheep-Alexa488, 1:1000, #A-11015
Immunostaining Protocol:
    15 min fixation in 4% PFA, 2×PBS wash, 30 min 5% FBS in 0.1% PBT, primary antibodies incubated in 1% FBS in PBS overnight at 4° C., secondary antibodies in PBS for 3 hr at RT, all washes in PBS, DAPI at 0.05 mg/ml for 5 min at RT, mounted in DAKOCytomation mounting medium.
Drug Transporters
    DE-Hep cells show immunoreactivity for the transporter MRP2 (FIG. 14 B). MRP2 is expressed both in hepatocyte-like cell cultures and in DE-Hep cell cultures.
Used Primary Antibodies:
    MRP2 (rabbit) 1:50, Santa Cruz, sc-20766
Used Secondary Antibodies:
    donkey anti-rabbit-Alexa488, 1:1000, Molecular Probes, #A-21206
Immunostaining Protocol:
    15 min fixation in 4% PFA, 2×PBS wash, 30 min 5% FBS in 0.1% PBT, primary antibodies incubated in 1% FBS in PBS overnight at 4° C., secondary antibodies in PBS for 1 hr at RT, all washes in PBS, DAPI at 0.05 mg/ml for 5 min at RT, mounted in DAKOCytomation mounting medium.

Example 19

Urea Excretion in DE-Hep Cells at Stage III

The determination of urea is the most widely used test for the evaluation of kidney function. Urea is the final degradation product of protein and amino acid metabolism. The ammonia formed in this process is synthesized to urea in the liver and constitute the most important catabolic pathway for eliminating excess nitrogen in the human body. The Roche UREA/BUN assay is based on Talke and Schubert's method using a totally enzymatic procedure for the determination of urea using the coupled urease/glutamate dehydrogenase (GLDH) enzyme system. Shortly, urea is hydrolyzed by urease to from $CO_2$ and ammonia. The ammonia formed then reacts with α-ketoglutarate and NADH in the presence of GLDH to yield glutamate and $NAD^+$. The decrease in absorbance due to consumption of NADH is measured kinetically. Normal values in serum/plasma are 10-50 mg/dL (1.7-8.3 mmol/L). Urea secretion was analyzed using a kit for kinetic UV assay for urea/urea nitrogen (Roche/Hitachi) at Klinisk Kemi, C-lab, Sahlgrenska University Hospital, Gothenburg. Both DE-Hep cells, control hepatocyte-like cells, HepG2 and human primary hepatocytes were found to produce urea (see Table 3).

Example 20

Quantification of the Specific CYP Activity Per Cell by Calculating the Number of CYP Immuno-Positive Cells or Cell Nuclei Per Culture Since DE-Hep cultures contain other cell types besides DE-Hep cells, it is desirable to determine the number of CYP expressing cells in order to be able to calculate the specific CYP activity per cell/cell nuclei. One possibility is to count those human nuclei (co-labelled with a nuclear stain like DAPI and an anti-human nuclei antibody) which are immunopositive for a specific CYP using automated cell analysing systems (e.g. In Cell analyser).

Using such a system, we have determined that DE-Hep cultures derived with protocol 2 contain about 19% CYP3A4 immuno-positive cell nuclei (whereof about 6% were highly immunopositive; see Table 8) while control cultures with hepatocyte-like cells contained about 2% CYP3A4 immunopositive cell nuclei (whereof 0.3% were highly immunopositive; see Table 8). From the absolute numbers of human CYP3A4 positive and highly positive nuclei it is possible to calculate the concentration of metabolite per 1000 CYP3A4 positive nuclei or per 1000 highly CYP3A4 positive nuclei. The same analysis can be performed on control cell types like human primary hepatocytes and HepG2 cells and then a direct comparison between these cell types is possible. In such an experiment, human primary hepatocytes from 3 different donors (cultured for 120 hr) contained on average 8.8% CYP3A4 positive nuclei. Compared to this, DE-Hep cultures contained with 19.4% more than double as many CYP3A4 positive nuclei.

TABLE 8

Calculation of human CYP3A4 positive nuclei in DE-Hep cultures

| Protocol | Number Human nuclei | Number Human CYP3A4 positive nuclei | % Human CYP3A4 positive nuclei | Number Human high CYP3A4 positive nuclei | % Human high CYP3A4 positive nuclei | nM 1OH-Midazolam (CYP3A4 metabolite) | nM 1OH Midazolam/ 1000 Human CYP3A4 positive nuclei | nM 1OH-Midazolam/ 1000 Human high CYP3A4 positive nuclei |
|---|---|---|---|---|---|---|---|---|
| DE-Hep cells, Protocol 2 | 40323 | 7830 | 19.4 | 2309 | 5.8 | 26 | 3.3 | 11.3 |
| intrinsically differentiated cells | 48675 | 1111 | 2.3 | 143 | 0.3 | 1 | 0.9 | 6.9 | per protocol the average from 2 identically treated wells was calculated.
Since a certain percentage of both DE-Hep cells and hepatocyte-like cells are found to be bi-nucleated (like human hepatocytes), the number of nuclei is not equal with the number of cells.

Example 21

Activin Treatment of hBS Cells as Single Cells and Clusters Of Cells

Before initiating a differentiation protocol, hBS cells were dissociated with Collagenase into single cells and clusters of cells. Thereafter, the single cells and clusters of cells were plated onto mouse embryonic fibroblasts (MEFs) or other matrixes and cultured according to either a DE-Hep differentiation strategy or according to the intrinsic differentiation strategy. In the following, 4 examples of such experiments are described and denoted as protocols A-D. These protocols all have a length of 5-7 days in culture. Thereafter, culturing of the cells is continued according to protocols 1-4 (see FIG. 1B).

Protocol A involves dissociation of hBS cells with Collagenase in order to obtain single cells and/or small cluster of cells. Those are then cultured in stage I medium on MEFs or other matrixes for 3-7 days and afterwards cultured according to the protocols 1-4 (see FIG. 1B and example 2), starting with stage II medium.

In protocol B the first three days are exactly as described for protocol A. Thereafter the medium is changed to VitroHES™ medium supplemented with 4 ng/ml FGF2 with or without 10% FBS and cultured for 2 additional days. The cells are thereafter cultured according to the protocols 1-4 (see FIG. 1B and example 2), starting with stage II medium.

Protocol C involves passage of hBS cells with Collagenase as described in Protocol A after which the hBS cells are plated in VitroHES™ supplemented with 4 ng/ml FGF2 and allowed to grow to 70% confluence before the cells are cultured according to the protocols 1-4 (see FIG. 1B and example 2), starting with stage I medium.

Protocol D involves passage of hBS cells with Collagenase or TrypleSelect onto MEFs and culturing in VitroHES™ medium as described above. They intrinsically differentiated into hepatocyte-like cells (see FIG. 11C).

Example 22

Sorting and Refinement of the DE-Hep Cells

Since DE-Hep cultures are a mixed population, it may be necessary to purify the desired cell population, as for example DE-Hep progenitors or DE-Hep cells. Purification can be performed with antibody-based methods like magnetic activated cell sorting (MACS) or fluorescence activated cell sorting (FACS) or methods based on gradient centrifugation like FICOLL or PERCOLL. For antibody-based methods (like FACS and MACS), antibodies directed against extracellular epitopes are required, e.g. asialoglycoprotein receptor (AS-GPR1) or drug transporters. For FACS an alternative to antibodies is to use fluorescent substrates for drug transporters, e.g. Fluo-3 for OATP-8, or for CYPs, e.g. 7-benzyloxy-4-trifluoromethyl-coumarin (BTC). These non-toxic fluorescent substrates transiently label the desired cell population and thus allow cell sorting without permanent changes or damages of the cells.

Example 23

Transfer to Collagen/Matrigel after Activin Induction

In stage I at day 5 the DE cells derived from hBS cells on MEF were dissociated with TripleSelect and transferred to a Matrigel and/or Collagen coated plates. The seeding density was 250 000 cells/cm$^2$. In the presence of stage II medium (see FIG. 1B and Example 2) the cells differentiated rapidly towards hepatic progenitor cells and proliferated as well (for morphology see FIG. 17). On day 16 in stage II many cells were EpCAM, CK7, CK19 and CD54 immunopositive (data not shown, compare Table 2 for markers expressed in DE-Hep progenitors).

Example 24

Derivation of Other Endodermal Cell Types

Besides DE-Hep cells, other endodermal cell types like enterocytes or other intestinal cells can be derived from hBS cells. Suitable markers for detection of such cell types are caudal-related homeobox 2 (Cdx2) and Intestinal Fatty Acid Binding Protein (IFABP). Cdx2 is highly expressed in intestinal epithelium and in the colon cancer cell line Caco-2 (data not shown). IFABP is expressed in small-intestinal enterocytes (data not shown). Neither Cdx2 nor IFABP could be detected on liver sections by immunohistochemistry (data not shown) and are therefore suitable to discriminate between enterocytes and hepatocytes in DE-Hep cultures.

Example 25

3D Systems Improve the Functionality of DE-Hep Cells

Primary human hepatocytes are known to show improved functionality in 2D cell cultures when simple 3D systems are applied e.g. a so called sandwich configuration, which means that a Matrigel or Collagen overlay is placed over the cells. Therefore, we tested such a Sandwich configuration also on DE-Hep cells and placed a Matrigel overlay over the cultures during the last 1-2 weeks. As shown in Table 9, this increased CYP1A2 and CYP3A4 activity and thus had a positive effect on functionality of the DE-Hep cells. Other 3D systems like beads, gels or matrices are contemplated to improve functionality as well.

TABLE 9

Improved Cytochrome P450 activity of DE-Hep cells in Sandwich configuration. Values are nM metabolite, see example 15.

| | Sample | CYP1A2 | CYP3A4 |
|---|---|---|---|
| 1a | DE-Hep cells, SA348, day 29 | 5 | 14 |
| 1b | DE-Hep cells with Matrigel overlay, SA348, day 29 | 26 | 45 |
| 2a | DE-Hep cells, SA002, day 29 | 16 | 5 |
| 2b | DE-Hep cells with Matrigel overlay, SA002, day 29 | 28 | 7 |

As shown in table 10, the same cells show increased gene expression for some key hepatic genes when a Matrigel overlay are present:

TABLE 10

Improved gene expression of DE-Hep cells in Sandwich configuration. Values are fold change relative to intrinsically differentiated cells.

| | Sample | UGT2B7 | Albumin | OATP2 | TAT |
|---|---|---|---|---|---|
| 1a | DE-Hep cells, SA046, day 29 | 45 | 325 | 4 | 9 |
| 1b | DE-Hep cells with Matrigel overlay, SA046, day 29 | 90 | 1055 | 12 | 12 |

Example 26

Expression of Phase II Enzymes in DE-Hep Cultures

Xenobiotics are metabolised by two sequential systems, the phase I and phase II enzyme systems. The phase I system consists of the Cytochrome P450 enzymes (CYPs), and the phase II system consists of e.g. the uridine diphosphoglucuronosyltransferases (UGTs), the glutathione transferases (GSTs) and the sulfotransferases (SULTs).

We analysed the expression of some selected phase II enzymes in DE-Hep cultures. In DE-Hep cultures we could detect expression of UGT1A6/4/3, UGT1A8 and UGT2B7 (Table 5B; protocol 1 and 2), as well as expression of GSTA1-1 and SULT1E1 (FIG. 19; protocol 4). Both GSTA1-1 and SULT1 E1 are expressed at very low levels in undifferentiated hBS cells and strongly upregulated during the differentiation process in DE-Hep cultures.

Example 27

Improving CYP2C9 Expression in hBS Derived DE-hep Cells

Different variations of culture conditions were applied in order to improve CYP2C9 expression in the DE-hep cells.

DE-hep cells derived from two different cell lines SA002 and SA348 were kept in culture in prolonged period of time in the stage III for additional 2 weeks until day 42 and compared with DE-heps at day 28. Extending the culture period in stage III led to a dramatic increase in CYP2C9 mRNA expression (6.6 fold for SA002 and 5.0 fold for SA348).

DE-heps cells were derived from 2 different cell lines SA002 and SA348 in a feeder free system, by transferring the undifferentiated hBS cells to filters (Millipore # PICMO1250, Lot R5PN16454) and cultured on the air-liquid interfase in the absence of feeders, in the medium as described for the DE-hep protocol. These cells were compared with DE-hep cells cultured on feeders for the same period of time, 28 days. CYP2C9 mRNA expression was dramatically increased in the absence of feeders compared to the usual growth conditions on feeders (3.0 and 4.0 fold for SA002 and SA348 respectively).

mRNA expression of CYP2C9 was measured by real-time PCR using the ABI/TaqMan method. In short, RNA was isolated from the cell cultures by using Qiagen's RNeasy system. cDNA was synthesized by using the ABI high capacity cDNA synthesis kit. RT-PCR was performed in a ABI 7500 by using TaqMan probe. The expression level was normalized the CREBBP expression. See FIG. 20.

Example 28

Gene Expression of DE-hep Cells Compared to hBS Cells Differentiated According to the Protocol Published by Cai et al.

In order to compare our protocol with the protocol published by Cai et al, we applied both protocols on hBS cells and analyzed the mRNA expression of several important hepatic genes. Cells differentiated by our DE-Hep protocol were expressing higher mRNA levels of albumin, CYP1A2, CYP2C9 and CYP3A4, FIG. 21.

Method:

SCED (single cell enzymatic dissociated) cells from cell line SA002 were separated from feeder cells by enzymatic dissociation into single cells with TryLe Select, while leaving most HFFs attached to the plate. The hBS cells were transferred to hanging drops for re-aggregation for 5 days in VitroHes medium containing 30% cellulose and plated on collagen coated cell culture dishes. The hBS cells were then exposed to our DE-hep protocol as well as the protocol published by Cai et. al. The resulting cell cultures were analysed for hepatic gene expression of several hepatic markers by real time PCR.

Example 29

Flow Cytometry

Flow cytometry was performed using a CYP1A2 antibody to quantify the percentage of CYP1A2 positive cells among DE-Hep culture at stage 3 (SA002, d28) and primary hepatocytes. The DE-Hep cells were dissociated with TriPIS for 20 min at 37 C. Primary hepatocytes were freshly isolated.

The cells were fixated in 0.5% PFA for 30 min. Intracellular staining was done after cell permeabilization using 0.5% Triton/PBS for 5 min. All cells have been stained for DAPI. All centrifugation steps were performed at 60 g for 3 min. The corresponding isotype was used as a control for unspecific binding of the monoclonal antibody (FIG. 22. A). Approximately 33.5% of all counted cells (DAPI) were positive for CYP1A2 in the DE-Hep cultures (4218 cells counted) (FIG. 22. B I/II). The primary hepatocytes consisted of 52% CYP1A2 positive cells (20000 cells counted) (FIG. 22. CI/II). Interestingly the DAPI profile depicts mononuclear, binuclear and multinuclear cells in both the DE-Hep and primary hepatocytes (FIG. 22. B, C).

Example 30

Substituting Activin A with Activin B for Induction of Endoderm

Undifferentiated hESC line SA002 were exposed to either activin A (100 ng/ml) or activin B (100 ng/ml) in the presence of 5 ng/ml bFGF for 5 days and analyzed for gene expression.

The mRNA expression of the endodermal markers Foxa2, Sox17 and CXCR4 was either the same or even higher upon activin B exposure compared to activin A. Additionally, the extraembryonal (ExE) markers Sox7, CDX2 and MT was the same or lower in cells cultured with activin B compared to activin A. This shows that activin B is equally good or even better than activin A for induction of endoderm. See FIG. 23.

Method:

mRNA expression of Foxa2, Sox17, CXCR4, Sox7, CDX2, MT was measured by real-time PCR using the ABI/TaqMan method. In short, RNA was isolated from the cell cultures by using Qiagen's RNeasy system. cDNA was synthesized by using the ABI high capacity cDNA synthesis kit. RT-PCR was performed in a ABI 7500 by using TaqMan probe. The expression level was normalized to CREBBP expression.

References

Heins N, Englund M C O, Sjöblom C et al. Derivation, characterization, and differentiation of human embryonic stem cells. STEM CELLS 2004; 22:367-76.

WO03055992, A method for the establishment of a pluripotent human blastocyst-derived stem cell line, Cellartis AB WO2004098285, Cryopreservation of human blastocyst stem cells by use of a closed straws vitrification method WO2004099394, A method for the efficient transfer of human blastocyst-derived stem cells from a feeder-supported to a feeder-free culture system Noaksson K, Zoric N, Zeng X, Rao M S, Hyllner J, Semb H, Kubista M, Sartipy P, Monitoring differentiation of human embryonic stem cells using real-time PCR. Stem Cells. 2005 November-December; 23(10):1460-7. Epub 2005 Aug. 4.

Sjögren-Jansson E, Zetterströbm M, Moya K, Lindqvist J, Strehl R, Eriksson P S. Large-scale propagation of four undifferentiated human embryonic stem cell lines in a feeder-free culture system, Dev Dyn. 2005 August; 233 (4):1304-14.

D'Amour K A, Bang A G, Eliazer S, Kelly O G, Agulnick A D, Smart N G, Moorman M A, Kroon E, Carpenter M K, Baetge E E., Production of pancreatic hormone-expressing endocrine cells from human embryonic stem cells., Nat. Biotechnol. 2006 November; 24(11):1392-401

D'Amour K A, Agulnick A D, Eliazer S, Kelly O G, Kroon E, Baetge E E., Efficient differentiation of human embryonic stem cells to definitive endoderm., Nat. Biotechnol. 2005 December; 23(12):1534-41.

Cai J, Zhao Y, Liu Y, Ye F, Song Z, Qin H, Meng S, Chen Y, Zhou R, Song X, Guo Y, Ding M, Deng H., Directed differentiation of human embryonic stem cells into functional hepatic cells., Hepatology. 2007 May; 45(5):1229-39.

Söderdahl T, Kuppers-Munther B, Heins N, Edsbagge J, Bjöbrquist P, Cotgreave I, Jernström B. "Glutathione transferases in hepatocyte-like cells derived from human embryonic stem cells." Toxicol In Vitro. 2007 August; 21 (5):929-37. Epub 2007 Feb. 2.

Specific Embodiments of the Invention Are:

Stage II—DE-Hep Progenitor

1. A method for the preparation of DE-Hep progenitor cells derived from human blastocyst-derived stem (hBS) cells via definitive endoderm, the method comprising i) culturing definitive endodermal cells derived from hBS cells in a culture medium comprising a growth factor, notably FGF2, and a bone morphogenic protein, notably BMP4, for 5 days or more, ii) optionally, harvesting the thus obtained hepatoblast-like progenitor cells.

2. A method according to item 1, wherein the culture medium is RPMI advanced medium or DMEM medium.

3. A method according to item 1 and 2, wherein the culture medium is supplemented with FGF2, PEST, and/or GlutaMAX.

5. A method according to any of the preceding item, wherein the medium is changed every day or every second day.

6. A method according to any of the preceding items, wherein the medium further comprises one or more of a growth factor, notably aFGF, and a bone morphogenic protein, notably BMP2.

7. A method according to any of the preceding items, wherein the medium further comprises serum such as, e.g., FCS.

8. A method according to any of the preceding items, wherein the medium further comprises HGF.

9. A method according to any of the preceding items, wherein the cells are cultivated according to the following scheme:
Days 1 and 2: the culture medium contains FGF2, BMP4, one or more further bone morphogenetic proteins, notably BMP2, serum, notably FCS, PEST, and GlutaMAX and, optionally, one or more further growth factors, notably aFGF.

10. A method according to any of the preceding items, wherein the cells are cultivated according to the following scheme:
Day 3: the culture medium contains FGF2, BMP4, serum, notably FCS, PEST, GlutaMAX, and optionally a hepatocyte growth factor.

11. A method according to any of the preceding items, wherein the cells are cultivated according to the following scheme:
Day 4: the culture medium contains FGF2, BMP4, HGF, serum, notably FCS, PEST, GlutaMAX, and a hepatocyte growth factor, or, alternatively the culture medium contains FGF1, FGF2 and serum, notably FCS.

12. A method according to any of the preceding items, wherein the cells are cultivated according to the following scheme:
Day 5: the culture medium contains FGF2, BMP4, HGF, serum, notably FCS, PEST, GlutaMAX, or, alternatively, the culture medium contains HGF, FGF2 and serum, notably FCS.

13. A method according to any of the preceding items, wherein the cells are cultivated according to the following scheme:
Days 6-8: the culture medium contains FGF2, HGF, serum, notably FCS, PEST, GlutaMAX.

14. A method according to any of the preceding items, wherein the cells are cultivated for 8 days, the concentration of FCS is increased at day 6 and a supplement of a growth factor, notably EGF, is given at day 6 and the medium was changed every day from day 6 to day 8.

Characterisation of DE-Hep Progenitors

15. A method according to any of the preceding items, wherein the cells obtained exhibit gene expression of one or more of HNF3b, HNF4a, EpCAM, AFP, Desmin, CD133, Notch2, ICAM1, CK7, CK18 and Ck19.

16. A method according to any of the preceding items, wherein the cells obtained exhibit gene expression of one or more of HNF1, HNF3b, HNF4a, EpCAM, AFP, Desmin, CD133, ICAM1, CK8, CK18 and Ck19.

17. A method according to any of the preceding items, wherein the cell population comprises at least 25% such as e.g. at least 50% cells exhibiting the markers defined in items 15-16.

Inclusion of Stage I

18. A method according to any of the preceding items, wherein the definitive endodermal cells are obtained by culturing hBS cells in a culture medium comprising activin A and optionally one or more growth factors, Wnt3a and serum, notably FCS.

19. A method according to item 18, wherein the culture medium is RPMI advanced medium or DMEM medium.

20. A method according to item 18 or 19, wherein the culture medium is supplemented with one or more growth factors, notably FGF2.

21. A method according to any of items 18-20, wherein the hBS cells are culture according to the following scheme:
Day 1: The culture medium contains Activin, Wnt3A and a growth factor, notably FGF2.

22. A method according to any of items 18-21, wherein hBS cells are culture according to the following scheme:
Day 2: The culture medium contains Activin, serum and a growth factor, notably FGF2.

23. A method according to any of items 18-22, wherein hBS cells are culture according to the following scheme:
Days 3 and 4: The culture medium contains Activin, serum and a growth factor, notably FGF2.

24. A method according to any of the preceding items, wherein culturing of definitive endodermal cells starts after culturing hBS cells for 4 days under conditions defined in items 18-23 for obtaining definitive endodermal cells.

25. A method according to any of items 1-17 or 24, wherein the culturing starting from definitive endodermal cells is continued for 5 days of more.

Stage III

26. A method according to any of the preceding items further comprising a step of culturing the DE-hep progenitor cells obtained as defined in any of items 1-23 in a culture medium like e.g. Williams E based medium or HCM Cambrex medium optionally supplemented with
a differentiation inducer such as, e.g., dexamethazone, omeprazole, rifampicin, desoxyphenobarbital, ethanol, isoniazide, alone or in combination;
an ITS mixture;
a BMP and/or TGFβ, notably BMP4 and/or
HGF.

27. A method according to item 26, wherein the culturing is carried out for 10-25 days or more.

28. A method according to item 27, wherein the culture medium is changed every day up to day 15 and, if relevant, changed every second day for the remaining culture period.

Characterisation of DE-Hep Cells Obtained from Method 24-26

29. A method according to any of items 26-28, wherein at least 20% of the cells or the cell nuclei in a cell population obtained exhibit at least one such as e.g. at least four, at least six, at least eight, at least ten or all of the following characteristics glucose 6 phosphatase, apolipoprotein E, CYP7A1 (cholesterol 7α hydroxylase), alcohol dehydrogenase 1, cytochrome P450 reductase, HNF4a, alpha-1-antitrypsin, CK18, HNF3b, albumin or Liver-Fatty-Acid-Binding-Protein and at least two, such as e.g. at least four, at least six, at least eight, at least ten or all of the following eleven characteristics A. Drug Transporters
i) at least 1% of the cells or, when relevant, cell nuclei exhibit protein and/or gene expression of BSEP, ii) at least 1% of the cells or, when relevant, cell nuclei exhibit protein and/or gene expression of MRP2,
iii) at least 1% of the cells or, when relevant, cell nuclei exhibit protein and/or gene expression OATP-2 (=OATP-C, OATP1B1) and/or OATP-8 (OATP1B3),
iv) at least 1% of the cells or, when relevant, cell nuclei exhibit protein and/or gene expression OATP-A (=OATP1A2)
v) at least 1% of the cells or, when relevant, cell nuclei exhibit protein and/or gene expression NTCP,
vi) at least 1% of the cells or, when relevant, cell nuclei exhibit protein and/or gene expression MDR1,
vii) at least 1% of the cells or, when relevant, cell nuclei exhibit protein and/or gene expression MDR3,
viii) at least 1% of the cells or, when relevant, cell nuclei exhibit protein and/or gene expression OCT-1

B. Drug Metabolising Enzymes
ix) at least 20% of the cells or, when relevant, cell nuclei exhibit protein and/or gene expression of GST A1-1 and/or GSTM1-1,
x) at least 5% of the cells or, when relevant, cell nuclei exhibit protein and/or gene expression of at least 2 of the following CYPs-1 A1, -1A2, -1B1, -2A6, -2B6, -2C8, -2C9, -2C19, -2D6, -2E1, -3A4, -3A7 and -7A1,
xi) at least 5% of the cells or, when relevant, cell nuclei exhibit protein and/or gene expression of UGT1A6 and/or UGT2B7.

30. A method according to any of items 26-29, wherein at least 20% of the cells in a cell population obtained exhibit at least one of the following characteristics Alpha-1-antitrypsin, Ck18, HNF-3beta, Albumin or Liver-Fatty-Acid-Binding-Protein and the cell population at least two of the following six characteristics A. Drug Transporters
i) at least 1% of the cells exhibit protein and/or gene expression of BSEP,
ii) at least 1% of the cells exhibit protein and/or gene expression of MRP2,
iii) at least 1% of the cells exhibit protein and/or gene expression OATP-2 and/or OATP-8, B. Drug Metabolising Enzymes
iv) at least 20% of the cells exhibit protein and/or gene expression of GST A1-1,
v) at least 20% of the cells exhibit protein and/or gene expression of at least 2 of the following CYP450s-1A2, -2A6, -2B6, -2C8, -2C9, -2C19-2D6, -2E1, -3A4 and -3A7,
vi) at least 5% of the cells exhibit protein and/or gene expression of GST M 1-1.

31. A method according to any of items 26-30, wherein at least 20% of the cells in a cell population obtained has at least one of said drug transporter characteristics and at least one of said drug metabolism characteristics.

32. A method according to item 29-31, wherein at least 20% of the cells of a cell population obtained has at least four, such as, e.g. at least five of said characteristics.

33. A method according to any of items 29-32, wherein at least 20% of the cells of a cell population obtained has all six of said characteristics.

34. A method according to any of items 29-33, wherein characteristic i) is valid for at least 5%, such as, e.g., at least 10%, at least 15%, at least 20%, at least 30%, at least 40%, at least 50%, at least 60%, at least 70%, at least 80%, at least 90% or at least 95% of the cells.

35. A method population according to any of items 29-34, wherein characteristic ii) is valid for at least 5%, such as, e.g., at least 10%, at least 20%, at least 30%, at least 40%, at least 50%, at least 60%, at least 70%, at least 80%, at least 90% or at least 95% of the cells.

36. A method according to any of items 29-35, wherein characteristic iii) is valid for at least 5%, such as, e.g., at least 10%, at least 20%, at least 30%, at least 40%, at least 50%, at least 60%, at least 70%, at least 80%, at least 90% or at least 95% of the cells.

37. A method according to any of items 29-36, wherein characteristic iv) is valid for at least 30%, such as, e.g., at least 40%, at least 50%, at least 60%, at least 70%, at least 80%, at least 90% or at least 95% of the cells.

38. A method according to any of items 29-37, wherein characteristic v) is valid for at least 30%, such as, e.g., at least 40%, at least 50%, at least 60%, at least 70%, at least 80%, at least 90% or at least 95% of the cells.

39. A method according to any of items 29-38, wherein characteristic vi) is valid for at least 10%, such as, e.g., at least 20%, at least 30%, at least 40%, at least 50%, at least 60%, at least 70%, at least 80%, at least 90% or at least 95% of the cells.

40. A method according to any of items 29-39, wherein at least about 30%, such as, e.g., at least about 40%, at least about 50%, at least about 60%, at least about 70%, at least about 80%, at least about 90%, or at least about 95% of the cells in the cell population express at least one of the following characteristics Alpha-1-antitrypsin, Cytokeratin 18, HNF-3beta, Albumin or Liver-Fatty-Acid-Binding-Protein.

41. A method according to any items 29-40, wherein at least about 5% of the cells obtained co-express Cytokeratin 18 and CYP3A4 and/or CYP3A7.

42. A method according to any of items 29-41, wherein at least 20% of the cells obtained expresses at least one of the CYP450 proteins is inducible upon addition of an inducer.

43. A method according to any of items 29-42, wherein at least 20% of the cells obtained expresses GST A1-1 and/or GST M1-1 proteins are inducible upon addition of an inducer.

44. A method according to any of items 29-43, wherein the expression of UGT protein is inducible upon addition of an inducer.

45. A method according to any of items 29-44, wherein at least 25% of the cells obtained exhibits enzymatic activity of at least one of the CYP450 proteins of characteristic v).

46. A method according to any of items 29-45, wherein at least 25% of the cells obtained exhibits GST enzymatic activity.

47. A method according to item 46, wherein the GST enzymatic activity is at least 0.4 μmol/min/mg, such as, e.g., at least 0.6 μmol/min/mg, at least 0.8 μmol/min/mg, at least 1.0 μmol/min/mg, at least 1.2 μmol/min/mg, at least 1.4 μmol/min/mg, or at least 1.6 μmol/min/mg of protein in a lysate of the cell population.

48. A method according to any of items 29-47, wherein the cell population exhibits UGT enzymatic activity.

49. A method according to any of items 29-48, wherein the cells obtained are cultured in vitro for at least 24 hours such as, e.g. at least 72 hours with maintained characteristics.

50. A method according to any of items 29-49, wherein at least 25% of the cells obtained further expresses alpha-1-antitrypsin, L-FABP and CK-18.

51. A method according to any of items 29-50, further comprising the use of feeder cells such as human or mouse feeder cells.

52. A method according to any of items 29-50, which do not include any use of feeder cells.

53. A method according to any of items 29-50, which, if relevant, include use of autologous feeder cells.

54. A method according to any of items 29-53, wherein the culture of the cells involves the use of a plastic cell culture vessel that is coated on the inside with one or more proteins, alone or in combination.

55. A method according to item 54, wherein the one or more proteins are selected from the group consisting of collagen, laminin and combinations thereof.

56. A method according to any of items 54 or 55, wherein said cell population is obtained using a 3D environment, such as a porous filter.

57. DE-hep progenitor cells obtainable by a method defined in any of items 1-15.

58. DE-hep progenitor cells characterized as defined in item 15-17.

59. DE-hep cells obtainable by a method defined in any of items 26-56.

60. DE-hep cells having characteristics as defined in any of items 29-56

61. Use of a cell population as defined in any of items 58-68, for use in a drug discovery process.

70. Use of a cell population as defined in any of items 57-61, in in vitro models for studying drug transporters.

71. Use of a cell population as defined in any of items 57-61, in in vitro models for studying drug metabolizing enzymes.

72. Use of a cell population as defined in any of items 57-61, in in vitro models for studying hepatogenesis, such as, e.g., early hepatogenesis.

73. Use of a cell population as defined in any of items 57-61, in in vitro models for studying human hepatoregenerative disorders.

74. Use of a cell population as defined in any of items 57-61, for in vitro hepatotoxicity testing.

75. Use of a cell population as defined in any of items 57-61, in a medicament.

76. Use of a cell population as defined in any of items 57-61, for the manufacture of a medicinal product for the prevention and/or treatment of pathologies and/or diseases caused by tissue degeneration, such as, e.g., the degeneration of liver tissue.

77. Use of a cell population as defined in any of items 57-61, for the manufacture of a medicinal product for the treatment of liver disorders.

78. Use of a cell population as defined in any of items 57-61, for the manufacture of a medicinal product for the prevention and/or treatment of liver disorders selected from the group consisting of auto immune disorders including primary biliary cirrhosis; metabolic disorders including dyslipidemia; liver disorders caused by e.g. alcohol abuse; diseases caused by viruses such as, e.g., hepatitis B, hepatitis C, and hepatitis A; liver necrosis caused by acute toxic reactions to e.g. pharmaceutical drugs; and tumor removal in patients suffering from e.g. hepatocellular carcinoma.

79. Use of a cell population as defined in any of items 57-61, for the manufacture of a medicinal product for the treatment and/or prevention of metabolic pathologies and/or diseases.

80. Use of one or more cells from a cell population as defined in any of items 57-61, for obtaining metabolically improved hepatocyte-like cells.

81. Use of one or more cells from a cell population as defined in any of items 57-61, for studying maturation towards hepatocyte-like cells.

82. A method for screening a compound for hepatocellular toxicity, comprising exposing cells from a cell population as defined in any of items 57-61, to the compound, and determine whether the compound is toxic to the cell.

83. A method for screening a compound for its ability to modulate hepatocellular function, comprising exposing cells from a cell population as defined in any of items 57-61, to the compound, determining any phenotypic or metabolic changes in the cells that result from contact with the compound, and correlating the change with an ability to modulate hepatocellular function.

The invention claimed is:

1. A method of making hepatocyte progenitor cells comprising:
   i) culturing human embryonic stem (ES) cells for 1-2 days in a culture medium comprising activin and no serum, followed by
   ii) culturing the cells obtained from step i) in a culture medium comprising activin, a fibroblast growth factor, and serum such that definitive endodermal cells expressing Sox17, HNF3b, and CXCR4 are obtained; wherein the total culture period in steps i) and ii) is 3-5 days, and,
   iii) culturing the definitive endodermal cells resulting from step ii) in culture medium comprising a fibroblast growth factor, a bone morphogenic protein, and no activin such that a cell population expressing EpCAM, HNF1, HNF3b, HNF4a, Desmin, CD133, c-kit, ICAM1, CK8, CK18, and CK19 is obtained, wherein said cell population comprises human hepatocyte progenitor cells.

2. The method according to claim 1, wherein the culture medium used in step i) and/or ii) comprises RPMI advanced medium or DMEM medium.

3. The method according to claim 1, wherein the culture medium used in step iii) comprises RPMI advanced medium or DMEM medium.

4. The method according to claim 1, wherein the fibroblast growth factor in the culture medium used in step iii) is selected from Fibroblast Growth Factor 1 (FGF1), Fibroblast Growth Factor 2 (FGF2), and Fibroblast Growth Factor 4 (FGF4).

5. The method according to claim 1, wherein the culture medium used in step iii) is changed every day or every second day.

6. The method according to claim 1, wherein the bone morphogenic protein in the culture medium used in step iii) is selected from Bone Morphogenic Protein 2 (BMP2) and Bone Morphogenic Protein 4 (BMP4).

7. The method according to claim 1, wherein the culture medium used in step iii) further comprises serum.

8. The method according to claim 1, wherein the Fibroblast Growth Factor in the culture medium used in step ii) is selected from Fibroblast Growth Factor I (FGF 1), Fibroblast Growth Factor 2 (FGF2), and Fibroblast Growth Factor 4 (FGF 4).

9. A method of making hepatocyte cells comprising:
   i) culturing human embryonic stem (ES) cells for 1-2 days in a culture medium comprising activin and no serum, followed by
   ii) culturing the cells obtained from step i) in a culture medium comprising activin, a fibroblast growth factor and serum such that definitive endodermal cells expressing Sox17, HNF3b, and CXCR4 are obtained, wherein the total culture period in steps i) and ii) is 3-5 days,
   iii) culturing the definitive endodermal cells resulting from step ii) in culture medium comprising a fibroblast growth factor, a bone morphogenic protein and no activin such that a cell population expressing EpCAM, HNF1, HNF3b, HNF4a, Desmin, CD133, c-kit, ICAM1, CK8, CK18 and CK19 is obtained, wherein said cell population comprises human hepatocyte progenitor cells, and iv) culturing the human hepatocyte progenitor cells resulting from step iii) in culture medium comprising Hepatocyte Growth Factor (HGF) such that a cell population comprising cells having hepatocyte structure and function is obtained.

10. The method according to claim 9, wherein the culturing in step iv) is carried out for at least 10 days.

11. The method according to claim 9, wherein the culture medium used in step iv) is changed every second to third day up to day 15.

12. The method according to claim 9, further comprising the use of feeder cells.

13. The method according to claim 9, which does not include any use of feeder cells.

14. The method according to claim 9, which includes use of autologous feeder cells.

15. The method according to claim 9, wherein the culture medium used in step iv) further comprises a differentiation inducer selected from the group consisting of dexamethazone, omeprazole, OSM, rifampicin, desoxyphenobarbital, ethanol, and isoniazide, alone or in combination.

16. The method of claim 9, wherein the cell population obtained in step iv) expresses the following immunocytochemical markers: $\alpha_1$-antitrypsin, $\alpha$FP, albumin, CK7, CK8, CK18, CK19, CYP1A2, CYP3A4, glycogen, HNF3b, ICG, LFABP, and MRP2.

17. The method of claim 9, wherein the cell population obtained in step iv) exhibits the following functions: Indocyanine green uptake and excretion; glycogen storage;

albumin secretion; LDL uptake; metabolism of the drugs Phenacetin, Diclofenac, and Midazolam; and ammonia metabolism.

18. The method of claim 9, wherein the cell population obtained in step iv) exhibits glycogen secretion.

* * * * *